United States Patent
Rubin et al.

(10) Patent No.: US 11,847,601 B2
(45) Date of Patent: Dec. 19, 2023

(54) PAYER QUALITY OF ACCESS TOOL

(71) Applicant: THE DEDHAM GROUP LLC, New York, NY (US)

(72) Inventors: Darin T. Rubin, New York, NY (US); Robert Hung, New York, NY (US); Bedrick Gadea, New York, NY (US)

(73) Assignee: THE DEDHAM GROUP LLC, New York, NY (US)

( * ) Notice: Subject to any disclaimer, the term of this patent is extended or adjusted under 35 U.S.C. 154(b) by 660 days.

(21) Appl. No.: 16/857,533

(22) Filed: Apr. 24, 2020

(65) Prior Publication Data

US 2020/0342375 A1 Oct. 29, 2020

Related U.S. Application Data

(60) Provisional application No. 62/839,208, filed on Apr. 26, 2019, provisional application No. 62/839,193,
(Continued)

(51) Int. Cl.
*G06Q 10/0637* (2023.01)
*G06Q 10/10* (2023.01)
(Continued)

(52) U.S. Cl.
CPC ....... *G06Q 10/0637* (2013.01); *G06F 16/245* (2019.01); *G06Q 10/10* (2013.01); *G06Q 30/0185* (2013.01); *G06Q 30/0205* (2013.01); *G06Q 30/0607* (2013.01); *G06Q 30/0623* (2013.01); *G06Q 30/0629* (2013.01); *G06Q 50/26* (2013.01); *G16H 10/60* (2018.01); *G16H 20/10* (2018.01); *G16H 40/20* (2018.01); *G16H 70/20* (2018.01); *G16H 70/40* (2018.01)

(58) Field of Classification Search
CPC .............. G06Q 10/0637; G06Q 10/10; G06Q 30/0185; G06Q 30/0205; G06Q 30/0607; G06Q 30/0623; G06Q 30/0629; G06Q 50/26; G16H 40/20; G16H 10/60; G16H 70/40; G16H 20/10; G16H 70/20; G06F 16/245

See application file for complete search history.

(56) References Cited

U.S. PATENT DOCUMENTS

| 8,380,540 B1* | 2/2013 | Smith | G06Q 10/10 705/3 |
| 9,378,531 B2* | 6/2016 | Pecora | G06Q 10/10 |

(Continued)

*Primary Examiner* — Aryan E Weisenfeld
(74) *Attorney, Agent, or Firm* — K&L Gates LLP

(57) ABSTRACT

A strategic decision support system is disclosed. The system can filter content received from a remote database coupled to a network to provide a graphical user interface to enable strategic decision making to expand utilization of a product. The system can include a local client computer to generate access to content stored in the remote database, at least one filtering scheme, a set of selectable filters configured to filter the content stored in the remote database according to the at least one filtering scheme, and a remote server coupled to the local client computer via the network to analyze access restrictions to the product based on a selected filter and the at least one filtering scheme to generate a graphical user interface displayed on the local client computer.

15 Claims, 47 Drawing Sheets

Related U.S. Application Data filed on Apr. 26, 2019, provisional application No. 62/839,197, filed on Apr. 26, 2019.

(51) Int. Cl.
*G16H 70/40* (2018.01)
*G06Q 50/26* (2012.01)
*G06F 16/245* (2019.01)
*G06Q 30/0601* (2023.01)
*G06Q 30/018* (2023.01)
*G06Q 30/0204* (2023.01)
*G16H 70/20* (2018.01)
*G16H 40/20* (2018.01)
*G16H 20/10* (2018.01)
*G16H 10/60* (2018.01)

(56) References Cited

U.S. PATENT DOCUMENTS

| | | | | |
|---|---|---|---|---|
| 2006/0178915 A1* | 8/2006 | Chao | ............ | G16H 20/10 |
| | | | | 705/14.1 |
| 2008/0183492 A1* | 7/2008 | Warren | ............ | G16H 20/10 |
| | | | | 705/2 |
| 2012/0303382 A1* | 11/2012 | Paul | ............ | G16H 20/10 |
| | | | | 705/2 |
| 2015/0039331 A1* | 2/2015 | Longman | ............ | G16H 70/40 |
| | | | | 705/2 |
| 2017/0004274 A1* | 1/2017 | Mehta | ............ | G06N 7/005 |

* cited by examiner

| Data Source | Payer Quality of Access | Provider Key Accounts | Third Party Programs |
|---|---|---|---|
| *Secondary Data* | ↘ 178a | ↘ 178d | ↘ 178g |
| *Analog Data Set / Panel Discussions* | ↘ 178b | ↘ 178e | ↘ 178h |
| *3rd Party Data* | ↘ 178c | ↘ 178f | ↘ 178i |

DATA SOURCES / INPUTS

Filter Table By: All Criteria   Restrictive Criteria   Less Restrictive Criteria   |▲ Restrictive Criteria   ○ Less Restrictive Criteria

| | Criteria Category | Criteria | # Accounts | % Commercial Pharmacy Coverage |
|---|---|---|---|---|
| ○ | Exclusion Criteria | Patient cannot tolerate more aggressive regimens | 6 | 24.2% |
| ○ | Specialty Pharmacy Mandate | — | 22 | 21.9% |
| ○ | Quantity Limit | 4 tablets per day | 8 | 16.4% |
| ○ | Quantity Limit | Not specified | 8 | 11.7% |
| ○ | Reauthorization Requirement | No evidence of progressive disease | 2 | 8.0% |
| ○ | Reauthorization Requirement | No drug-induced hepatitis | 1 | 4.8% |
| ○ | Counseling Requirement | Pregnancy and contraceptive counseling | 1 | 4.8% |
| ○ | Reauthorization Requirement | Member is clinically benefitting | 1 | 4.8% |

Review Timing

Indication: NSCLC ▼

Commercial Medical | Medicare Medical

| Product | Line of Therapy | MONTHS Expansion | MONTHS Launch |
|---|---|---|---|
| Product 1 | 1L | 0 | — |
| Product 2 | 2L+ | 2 | — |
| Product 3 | 1L+ | 0 | — |
| Product 4 | 1L+ | 2 | — |
| Product 5 | 1L+ | 0 | — |
| Product 6 | 2L+ | 0 | — |
| Product 7 | Stage III | 0 | — |
| Average Review Timing | | 0.6 | — |

Default Coverage Pre-Review

- Pharmacy Director Review via Exceptions
- Not Covered Until Formal Review

Default NCCN Policy
Defer to NCCN Default Guidelines
Recognized Level of Recommendation  NO  2B

Exceptions Requirements to Obtain Coverage

Launch    Expansion    Off-Label Use

- Attestation of failed alternatives
- Documentation providing rationale for use of therapy (e.g. FDA-approved)
- Physician Must Provide Supporting Literature
- Pharmacy Department must approve therapy use

FIG. 21

Payer Quality Of Access: Indication

| Product 1 | PA to Label; Additional Criteria |
| Product 2 | PA to NCCN; Additional Criteria |
| Product 3 | Not Launched |
| Product 4 | PA to Label; Additional Criteria |
| Product 5 | PA to Label; Additional Criteria |

Product 1 | Dominant Quality of Access
◉ View Policy
- o PA to Label; Additional Criteria
- Formulary Tier
- Non-Preferred Specialty

Policy Criteria
- o Testing Requirement: FDA-Approved Test Required
- o Specialty Pharmacy Mandate
- o Age Requirement: 18+
- o Dosage Requirement: Use as monotherapy
- o Clinical Testing: Monitoring for QTc interval elongation & Guillan-Barre Syndrome
- o Reauthorization Requirement: No evidence of progressive disease
- o Clinical Testing: Monitoring for symptoms of differentiation syndrome
- o Quantity Limit: 2 tablets per day

Participating Value-Based Models Positioning
Pathways   Alternative Payment Model

| Organization | PHARMACY Lives Exposure | FDA, 2L Product 1 | Relative Access to FDA Line | Alignment to Aetna Policy |
|---|---|---|---|---|
| Pathway 1 | 360,586 | No Pathways | No Pathways | NOT ALIGNED |
| Pathway 2 | 346,379 | 2L+ | Parity | ALIGNED |
| Pathway 3 | 268,454 | No Pathways | No Pathways | NOT ALIGNED |

FIG. 22

Clinical Capabilities & Organizational Progressiveness (Y-Axis; Max Score: 20)

Payment Model Sophistication (Max score: 7)

OCM Participation — Whether or not accounts are participating in OCM, given the significant infrastructure requirements
- No = 0; Yes = 2

Other APM Participation — Other APM participation & impact on TCC perceptions across anchor tumors
- No = 0; 1 APM = 1; ≥2 APM / PPS-Exempt = 2

APM / OCM as IO Focus Area — Based on survey responses
- Very Low (1) = 0; Low (2) = 0.5; Medium (3) =1; High (4-5) 2

APM Impact on Product Use — Whether APM participation is having an impact on product utilization (may obtain multiple points)
- No = 0; Impact on Combination Therapy or IO Utilization = 0.5 point each

Personalized Medicine Investment (Max score: 4; Normalize to 6)

Biomarker Testing Capabilities — Accts invested in PD-L1 / NGS capabilities recognize the importance of pers. med. on future prescribing
- Low (0-1) Internal Capabilities = 1; High (≥2) Internal Capabilities = 2

Physician Buy-In — Physician support for pers. med. across the organization demonstrates consensus around IO therapeutic value as well as future pers. med. approaches
- Low = 0; Medium = 1; High = 2

Standard of Care Development & Adoption (Max score: 7)

IO Clinical Trial Volume — Accounts with greater IO clinical trial volume have higher perception of IO therapies
- No trials = 0; Low (1-3) = 1; Medium (4-6) = 2; High (≥7) = 3

Quality Memberships / Certifications — Member institutions create consensus on new SoC based on available data (may obtain multiple points)
- None = 0; NCI, NCCN, or QOPI = 1 point each

Early Adopter Mentality — Accounts that have rapidly adopted newer IO therapies represent progressiveness
- Combined Imfinzi & Bavencio MS <3% National Average = 0; If ≥3% = 1

Centralized Operations & Restrictiveness (X-Axis; Max Score: 20 (multiply summed score x 2))

| External Pathways / Internal Protocols Use (Max score: 6, Normalize to 8) |
|---|

| Existence & Structure | Whether or not accounts have formally-developed pathways beyond aligning to national guidelines<br>○ None = 0; In development = 0.5; Via, COME HOME, Value Pathways, or Internal = 1 |
|---|---|
| Adherence Level | Compliance rate informs on provider-pathways deviation; low adherence rate = high physician autonomy<br>○ Actual Adherence <80% = 0; Actual Adherence ≥80% =1 |
| EMR-Order Set Integration | Integrated pathways / protocols are easier to enforce than pathways housed in an external portal<br>○ Not Linked = 0; Pathways / Protocols Linked to EMR = 1 |
| Order Set Communications | Preferences / order sets communicated through multiple modalities have higher likelihood of compliance<br>○ Weak (single modality) = 0; Strong (multiple modalities) = 1 |
| Incentive / Penalties Structure | Pathways adherence enforced through financial means demonstrates a higher level of top-down control<br>○ No incentives / penalties = 0; Incentives / Penalties In Development = 1; Incentives / Penalties = 2 |

576

| Contracting / Product Preferences Pull-Through (Max score: 1, Normalize to 2) |
|---|

| Contracting Partnerships | Contracting partnerships lead to product preferencing<br>○ No = 0; Preference defined as ≥10% Increase over National Average Market Share = 1 |
|---|---|

FIG. 27

| Oncologists Exposure: North Carolina | | |
|---|---|---|
| Pathways | PARTICIPATING Provider | PARTICIPATING Oncologists |
| Pathway 1 | Provider 1 | 207 |
| Pathway 1 | Provider 2 | 135 |
| Pathway 2 | Provider 3 | 99 |
| Pathway 1 | Provider 3 | 99 |
| Pathway 3 | Provider 4 | 83 |

Positioning: Indication 2
Recommended pathways positioning compared to the FDA-approved line of therapy ○ Advantaged ○ Parity ○ Some Restrictions ● Off Pathways
○ Not Reviewed ◐ No Pathways Coverage ○ Not Managed

| Brand | FDA Line | Positioning |
|---|---|---|
| Product 1 | 2L+ | 2L+ |
| Product 2 | 2L+ | 2L+ |
| Product 3 | 1L+ | OFF |
| Product 4 | Maintenance & 1L+ | Maintenance & 1L+ |
| Product 5 | 1L+ | 1L+ |
| Product 6 | 1L | X 1L X |
| Product 7 | 1L+ | OFF |
| Product 8 | 1L | OFF |
| Product 9 | 1L+ | 2L+ |

Indication 1  NOT COVERED

Indication 2  COVERED

FIG. 49

PAYER QUALITY OF ACCESS TOOL

CROSS-REFERENCE TO RELATED APPLICATIONS

The present application claims priority under 35 U.S.C. § 119(e) to U.S. Provisional Patent Application No. 62/839,193, entitled PAYER QUALITY OF ACCESS TOOL, filed Apr. 26, 2019, to U.S. Provisional Patent Application No. 62/839,197, entitled PROVIDER KEY ACCOUNTS TOOL, filed Apr. 26, 2019, and to U.S. Provisional Patent Application No. 62/839,208, entitled THIRD PARTY PROGRAM TRANSPARENCY TOOL, filed Apr. 26, 2019, the disclosure of each of which is herein incorporated by reference in its entirety.

BACKGROUND

A patient's access to a product or treatment can be at least partially controlled by payers, providers, and/or third parties intermediaries to the payer and the provider. Payers include commercial insurers like Aetna, Humana, and Cigna, as well as other payers like Medicare, Medicare Advantage, Medicaid, Tricare, and Veterans Administration (VA), for example. Providers include independent physicians, community practices, hospitals, medical centers, and health systems, for example. Third parties include pathway organizations and alternative payment model (APM) stakeholders, for example.

In certain instances, though a product or treatment may be approved by the U.S. Food & Drug Administration (FDA), a patient's access to the product may be restricted by the payers, providers, and/or third parties. For example, a payer may make coverage of the product too restrictive, too burdensome, or too expensive; a provider may not want to employ and/or prescribe the product due to unfamiliarity or lack of training; and/or third parties may not facilitate or encourage use of the product. These barriers to utilization of an FDA-approved product or treatment can prevent patients from accessing certain products that may be helpful and/or necessary for their health. Such barriers are often most acute in the fields of oncology and specialty therapeutics in which new pharmaceutical products and treatments are constantly entering the market and/or being evaluated for new indications and/or uses. Additionally, the stakes in the fields of oncology and specialty therapeutics can be very high with respect to both costs and the patient's health.

SUMMARY

In one aspect, a strategic decision support system for filtering content received from a remote database coupled to a network is configured to provide a graphical user interface to enable strategic decision making to expand utilization of a product, wherein the strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network to analyze access restrictions to the product based on a selected filter and the at least one filtering scheme to generate a graphical user interface displayed on the local client computer.

In a further aspect of the strategic decision support system, the remote server is configured to analyze payer restrictions to the product, wherein a payer restriction is a restriction that originates at a payer level.

In a further aspect of the strategic decision support system, the set of selectable filters comprise at least one of an indication filter, a line of therapy filter, a patient sub-type filter, a product filter, a coverage filter, or any combination thereof.

In a further aspect of the strategic decision support system, the remote server is configured to select payers and compare quality of access of the product for each of the selected payers for the selected filters.

In a further aspect of the strategic decision support system, the remote server is further configured to extract policy criteria from a first payer policy, extract policy criteria from a second payer policy, and compare the extracted policy criteria to determine a value for each comparable criteria of the first payer policy relative to the second payer policy.

In a further aspect of the strategic decision support system, the remote server is further configured to calculate a relative quality of access score by weighing the values for each comparable criteria of the first and second payer policies and displaying the quality of access score on the graphical user interface of the local client computer.

In one aspect, a strategic decision support system for filtering content received from a remote database coupled to a network is configured to provide a graphical user interface to enable strategic decision making to expand utilization of a product, wherein the strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network to analyze access restrictions to the product based on a selected filter and the at least one filtering scheme to generate a graphical user interface displayed on the local client computer, wherein the remote server is configured to analyze provider restrictions to the product, and wherein a provider restriction is a restriction that originates at a provider level.

In a further aspect of the strategic decision support system, wherein the set of selectable filters comprise at least one of an indication filter, a line of therapy filter, a patient sub-type filter, a product filter, a coverage filter, or any combination thereof.

In a further aspect of the strategic decision support system, the remote server is configured to select providers and compare quality of access of the product for each of the selected providers for the selected filters.

In a further aspect of the strategic decision support system, the remote server is configured to determine a centralized operations and restrictiveness score and a clinical capabilities and progressiveness score for each of the selected providers, segment the selected providers into segmentation categories based on the centralized operations and restrictiveness score and the clinical capabilities and progressiveness score, and display the segmentation categories for each of the selected providers on the graphical user interface of the local client computer.

In one aspect, a strategic decision support system for filtering content received from a remote database coupled to a network is configured to provide a graphical user interface to enable strategic decision making to expand utilization of a product, wherein the strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network to analyze access restrictions to the product based on a selected filter and the at least one filtering scheme to generate a graphical user interface displayed on the local client computer, wherein the remote server is configured to analyze third party restrictions to the product, wherein a third party restriction is a restriction that originates at a third party level, and wherein a third party is intermediate to the payer and the provider.

In a further aspect of the strategic decision support system, the set of selectable filters comprise at least one of an indication filter, a line of therapy filter, a patient sub-type filter, a product filter, a coverage filter, or any combination thereof.

In a further aspect of the strategic decision support system, the remote server is configured to select third parties and compare quality of access of the product for each of the selected third parties for the selected filters.

In a further aspect of the strategic decision support system, the remote server is configured to determine regulatory approved use of the product, compare the regulatory approved use to a third party recommended use of the product, categorize a restrictiveness of the regulatory approved use relative to the third party recommended use of the product, and display the restrictiveness on the graphical user interface of the local client computer.

In a further aspect of the strategic decision support system, the remote server is configured to compare the regulatory approved use to another third party recommended use of the product, categorize another restrictiveness of the regulatory approved use relative to the other third party recommended use of the product, and display the other restrictiveness on the graphical user interface of the local client computer.

FIGURES

The novel features of the various aspects are set forth with particularity in the appended claims. The described aspects, however, both as to organization and methods of operation, may be best understood by reference to the following description, taken in conjunction with the accompanying drawings.

FIG. 4 is a table depicting data sources for various tools, according to at least one aspect of the present disclosure.

FIG. 10 is a graphical representation depicting policy criteria that is utilized in determining a restrictiveness classification for the quality of access analyses of FIGS. 8 and 9, according to at least one aspect of the present disclosure.

FIG. 13 is a graphical representation depicting relative quality of access analyses for a product (e.g. "Product 1") in comparison to an analog product (e.g. "Analog 1") via the Payer Quality of Access Tool of FIG. 5, according to at least one aspect of the present disclosure.

FIG. 21 is a graphical representation depicting a portion of a review process summary for the payer of FIG. 19, according to at least one aspect of the present disclosure.

FIG. 22 is a graphical representation depicting a portion of a product coverage summary for the payer of FIG. 19, according to at least one aspect of the present disclosure.

FIG. 26 is a graphical representation showing a scoring algorithm for the clinical capability score of FIG. 25, according to at least one aspect of the present disclosure.

FIG. 27 is a graphical representation showing a scoring algorithm for the centralized operations and decision-making score of FIG. 25, according to at least one aspect of the present disclosure.

Figure 5:
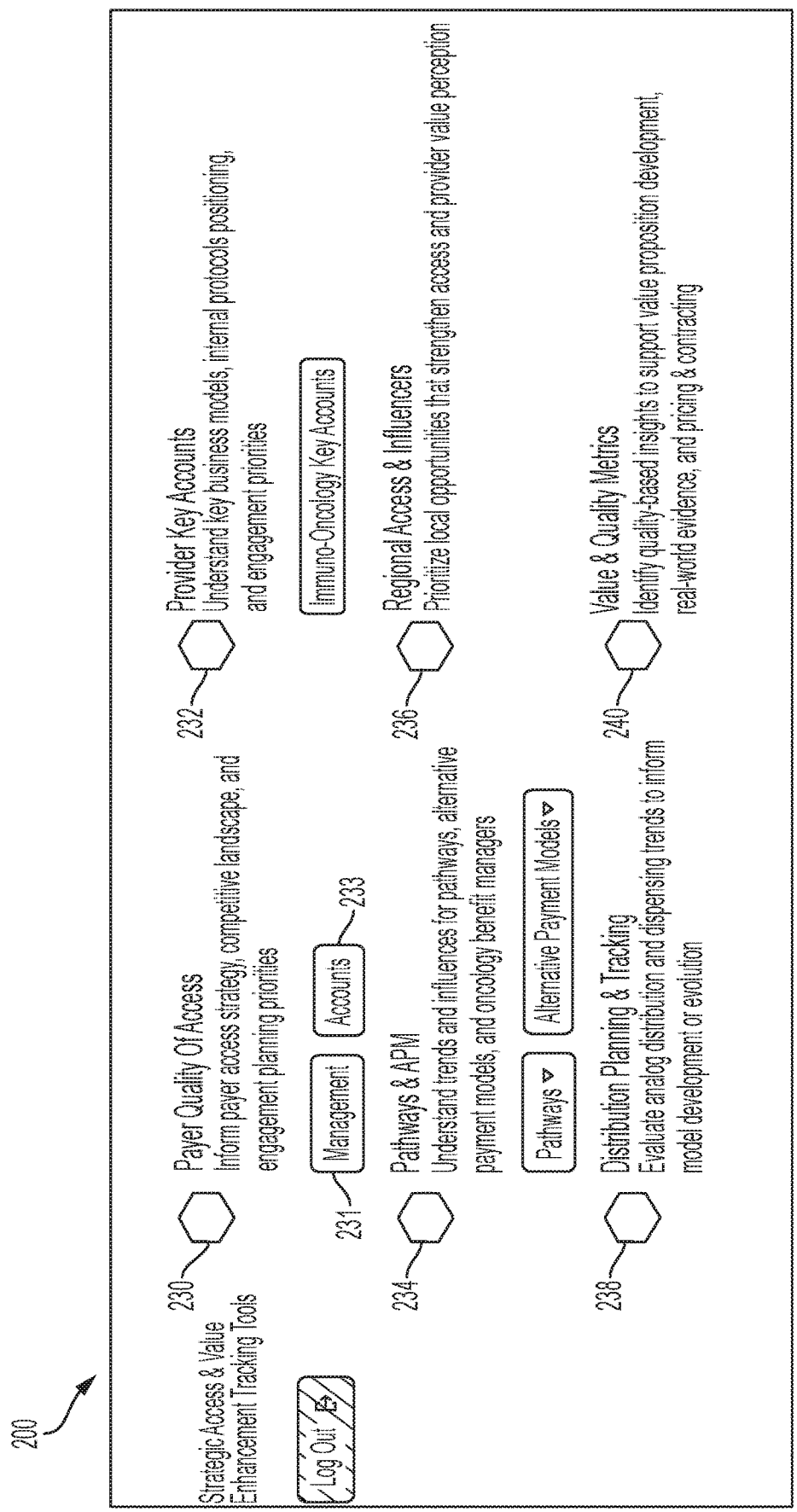
FIG. 5 is a graphical representation of a user interface display of an integrated decision-support portal including a Payer Quality of Access Tool, Provider Key Accounts Tool, Pathways & APM Tool, Regional Access & Influencers Tool, Distribution Planning & Tracking Tool, and Value & Quality Metrics Tool, according to at least one aspect of the present disclosure.
Figure 37:
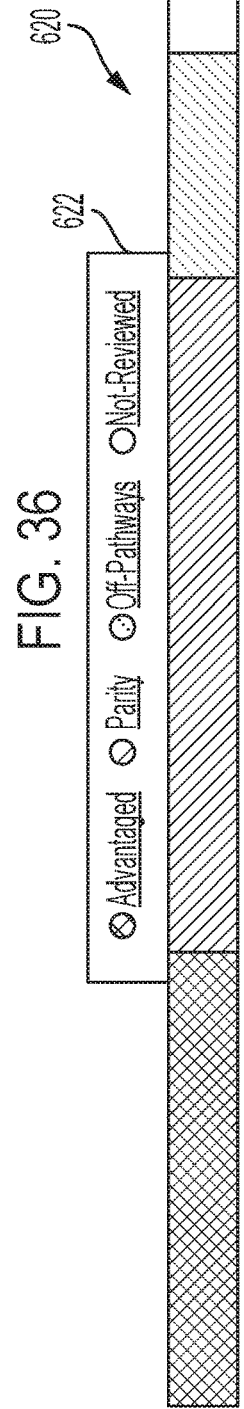

FIG. 37 is a graphical representation depicting relative pathways versus the FDA label for a particular product and summarizing the number of accounts advantaged relative to the FDA label, at parity with the FDA label, recommended with some restrictions beyond the FDA label, off-pathways, and/or not reviewed, and further listing the pathways in each category for the Pathways & APM Tool of FIG. 5, according to at least one aspect of the present disclosure.

Figure 37A:
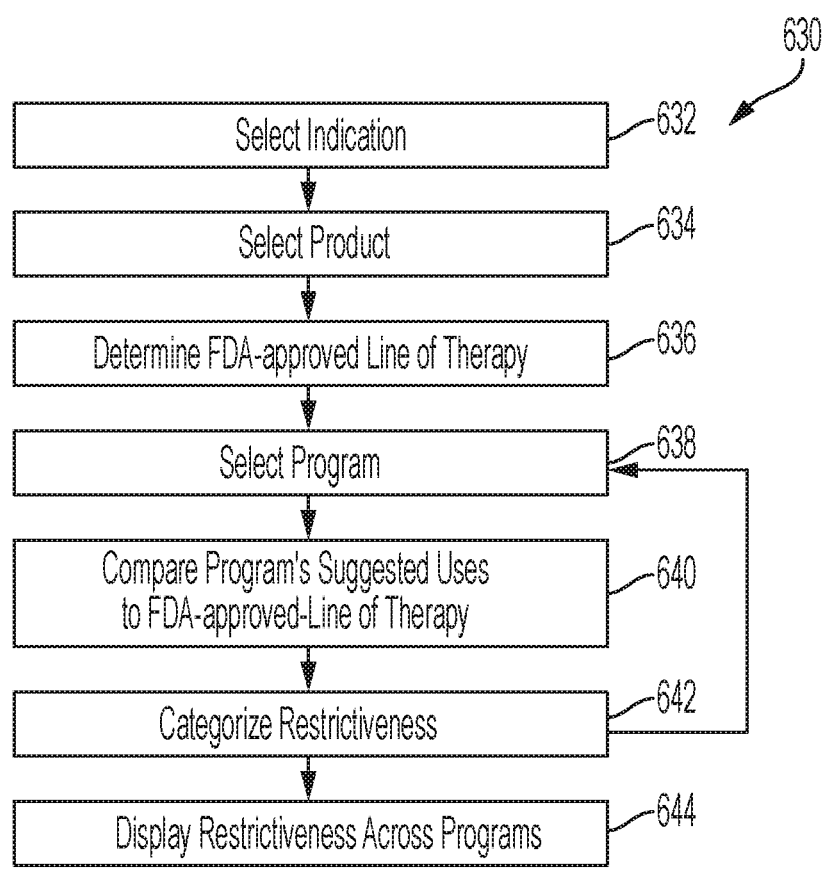

FIG. 37A is a logic diagram depicting steps to display restrictiveness of a product relative to the FDA label's approved line(s) of therapy across multiple programs for the relative pathways analysis of FIG. 37, according to at least one aspect of the present disclosure.

Figure 38:
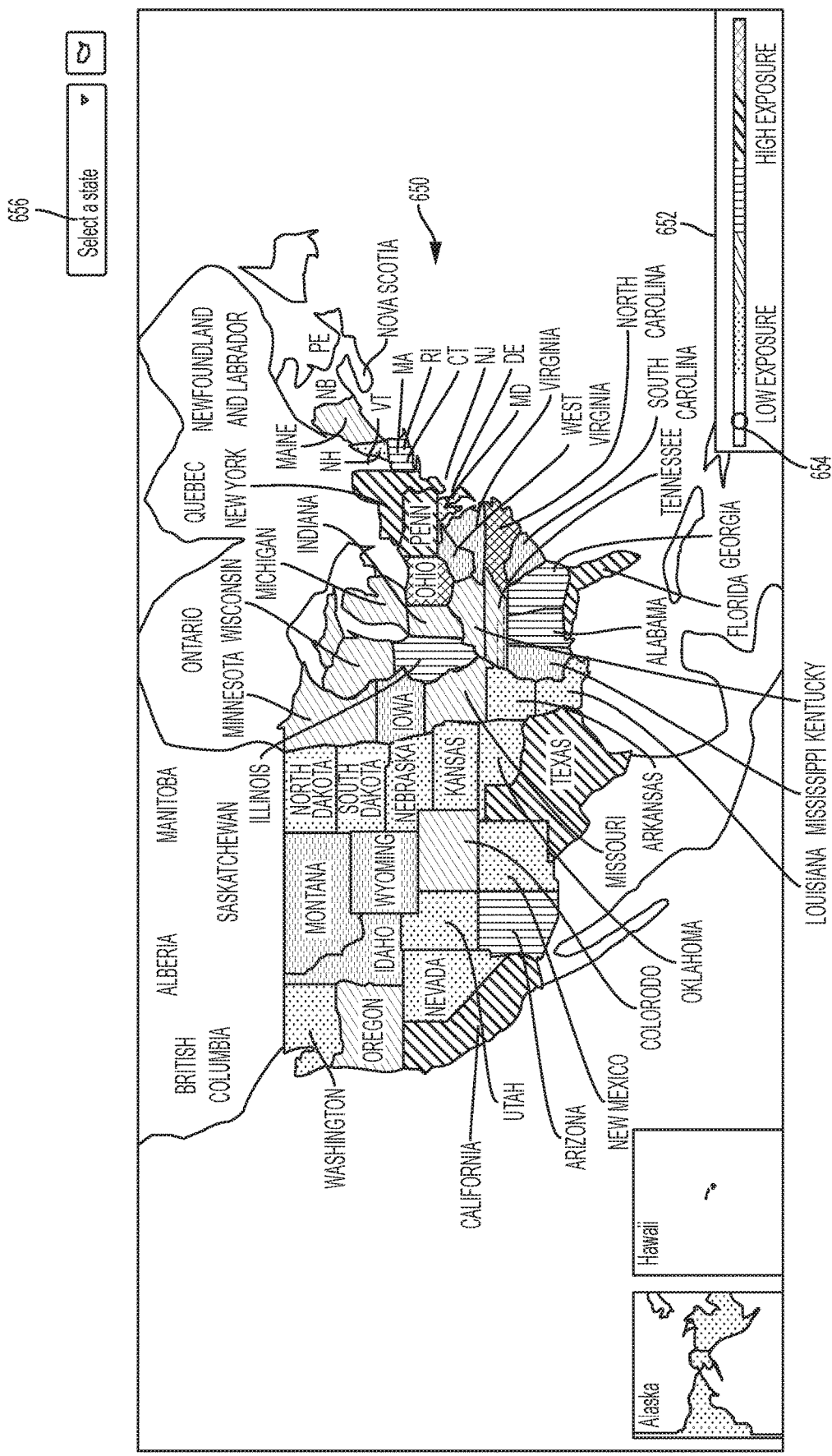

FIG. 38 is a graphical representation of a map depicting regional exposure of oncologists participating in pathways for the Pathways & APM Tool of FIG. 5, according to at least one aspect of the present disclosure.

Figure 39:

FIG. 39 is a graphical representation of oncologist exposure by pathway and provider for a selected jurisdiction—North Carolina—for the Pathways & APM Tool of FIG. 5, according to at least one aspect of the present disclosure.

Figure 40:
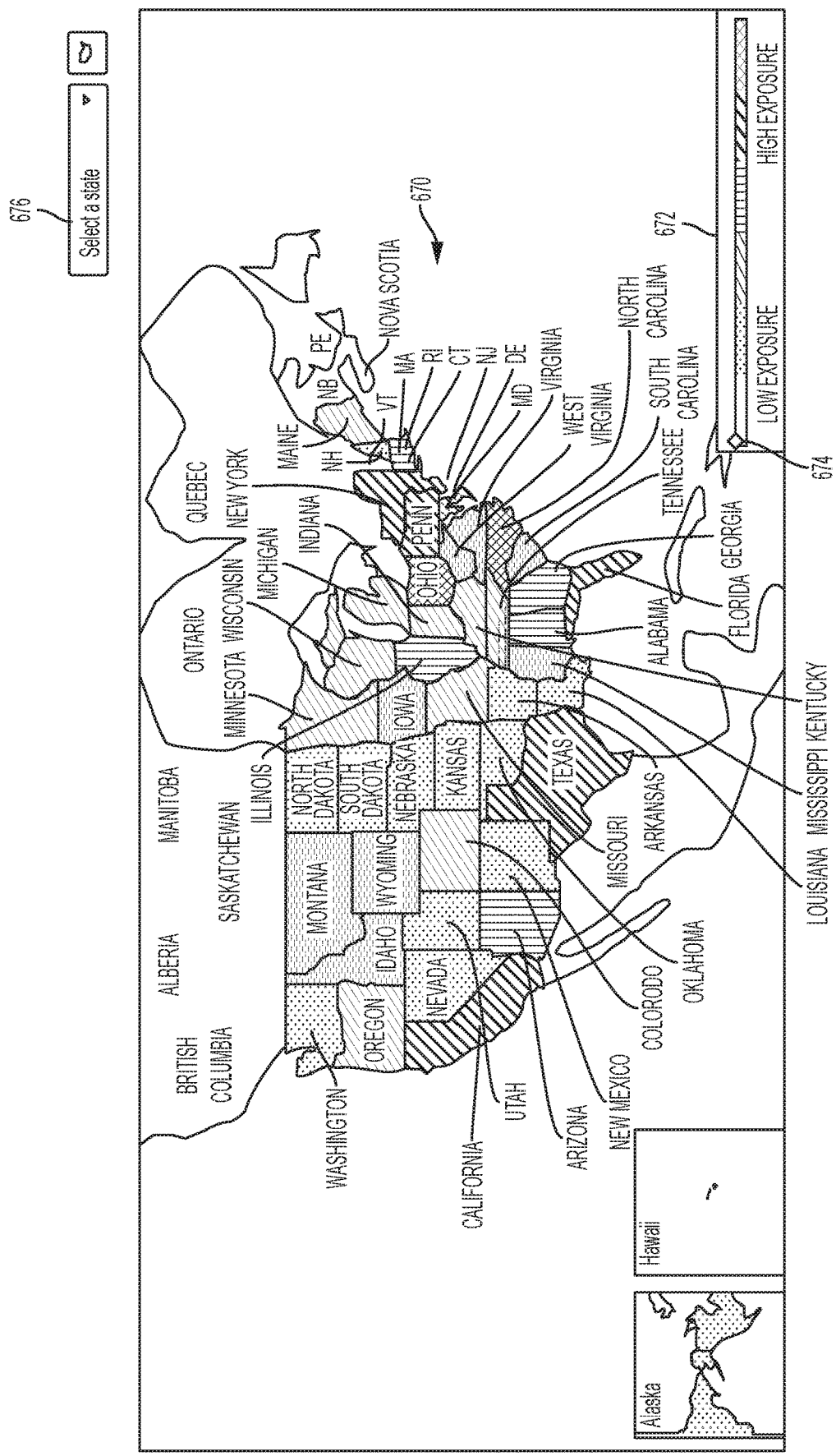

FIG. 40 is a graphical representation of a map depicting regional exposure of payer medical lives exposed to pathways for the Pathways & APM Tool of FIG. 5, according to at least one aspect of the present disclosure.

Figure 41:

FIG. 41 is a graphical representation of payer lives exposure by pathway and provider for a selected jurisdiction—North Carolina—for the Pathways & APM Tool of FIG. 5, according to at least one aspect of the present disclosure.

Figure 42:
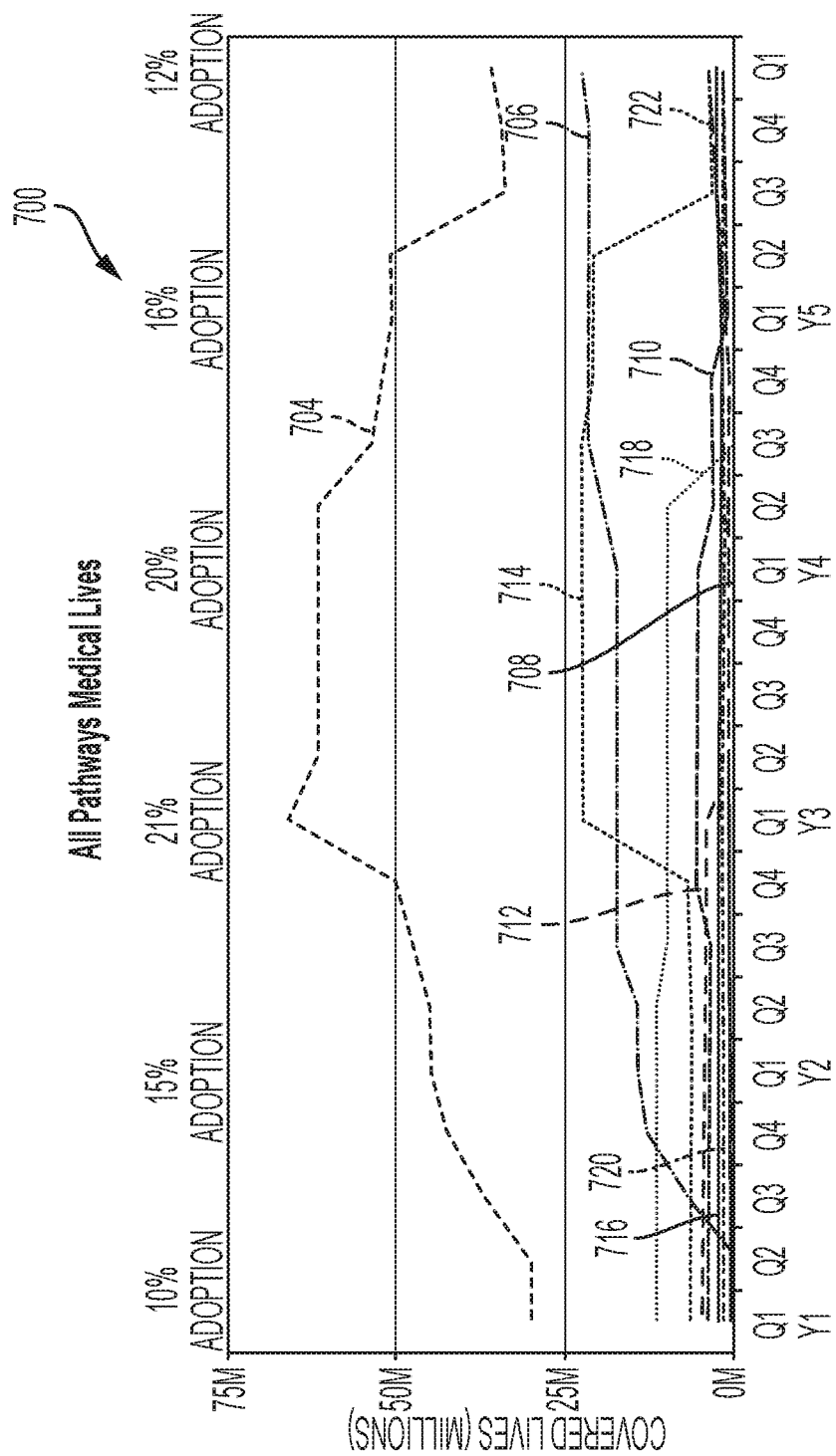

FIG. 42 is a graphical representation of a timeline depicting payer adoption based on covered medical lives over time by pathway and for all pathways combined for the Pathways & APM Tool of FIG. 5, according to at least one aspect of the present disclosure.

Figure 43:
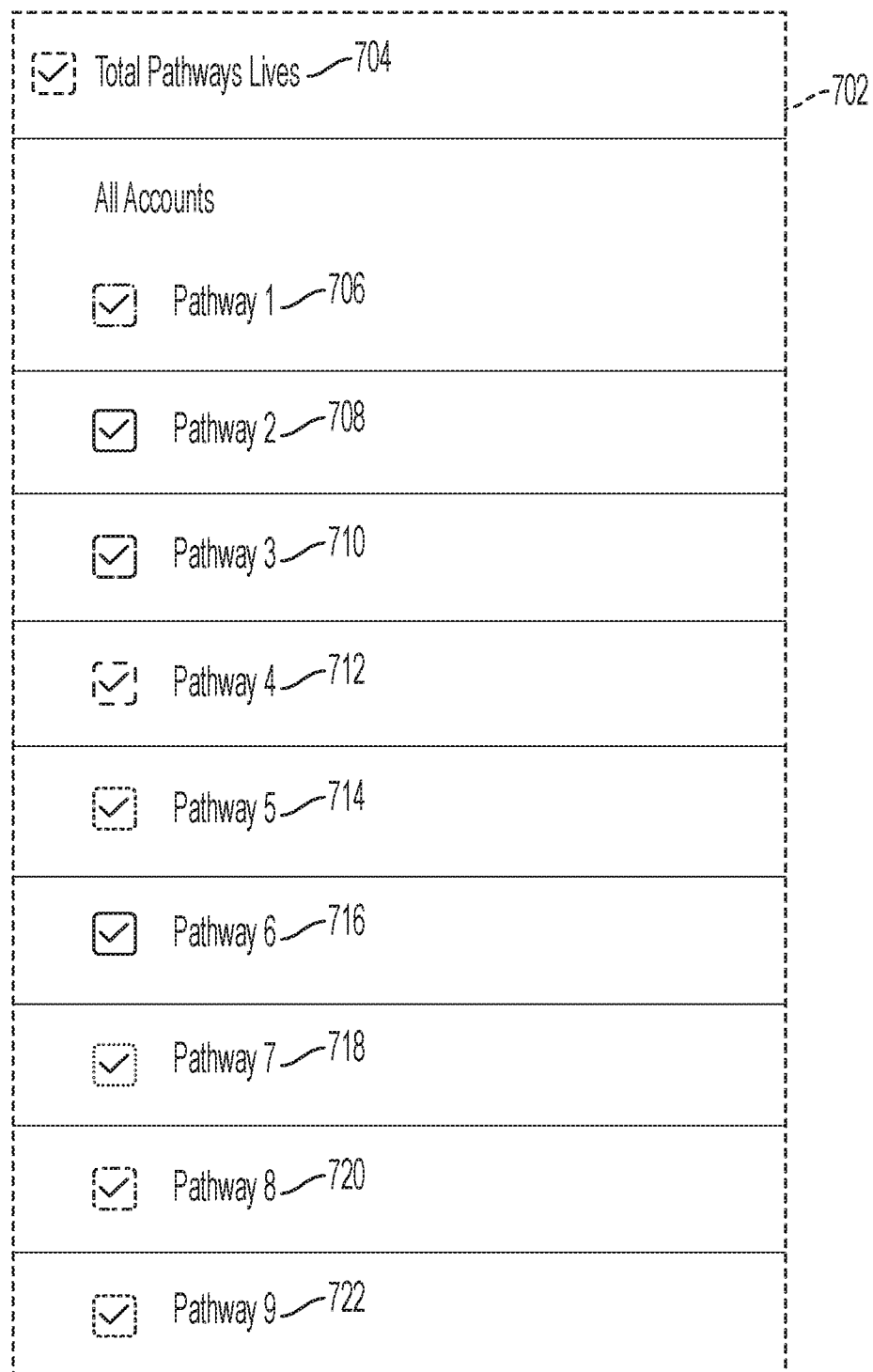

FIG. 43 is a graphical representation of a key for the pathways shown in the timeline of FIG. 42, according to at least one aspect of the present disclosure.

Figure 44:
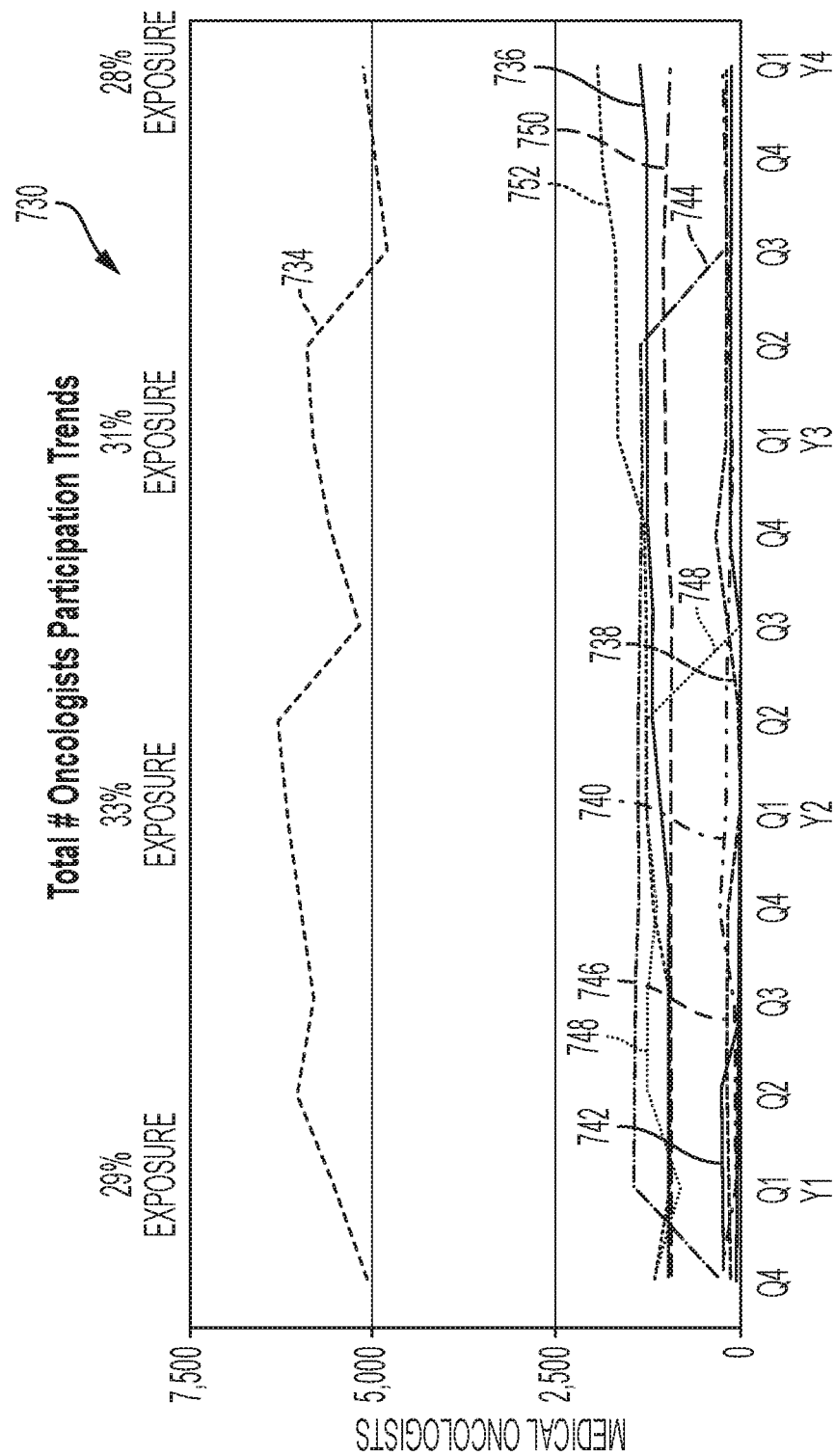

FIG. 44 is a graphical representation of a timeline depicting provider utilization based on number of oncologists participating in pathways over time by pathway and for all pathways combined for the Pathways & APM Tool of FIG. 5, according to at least one aspect of the present disclosure.

Figure 45:
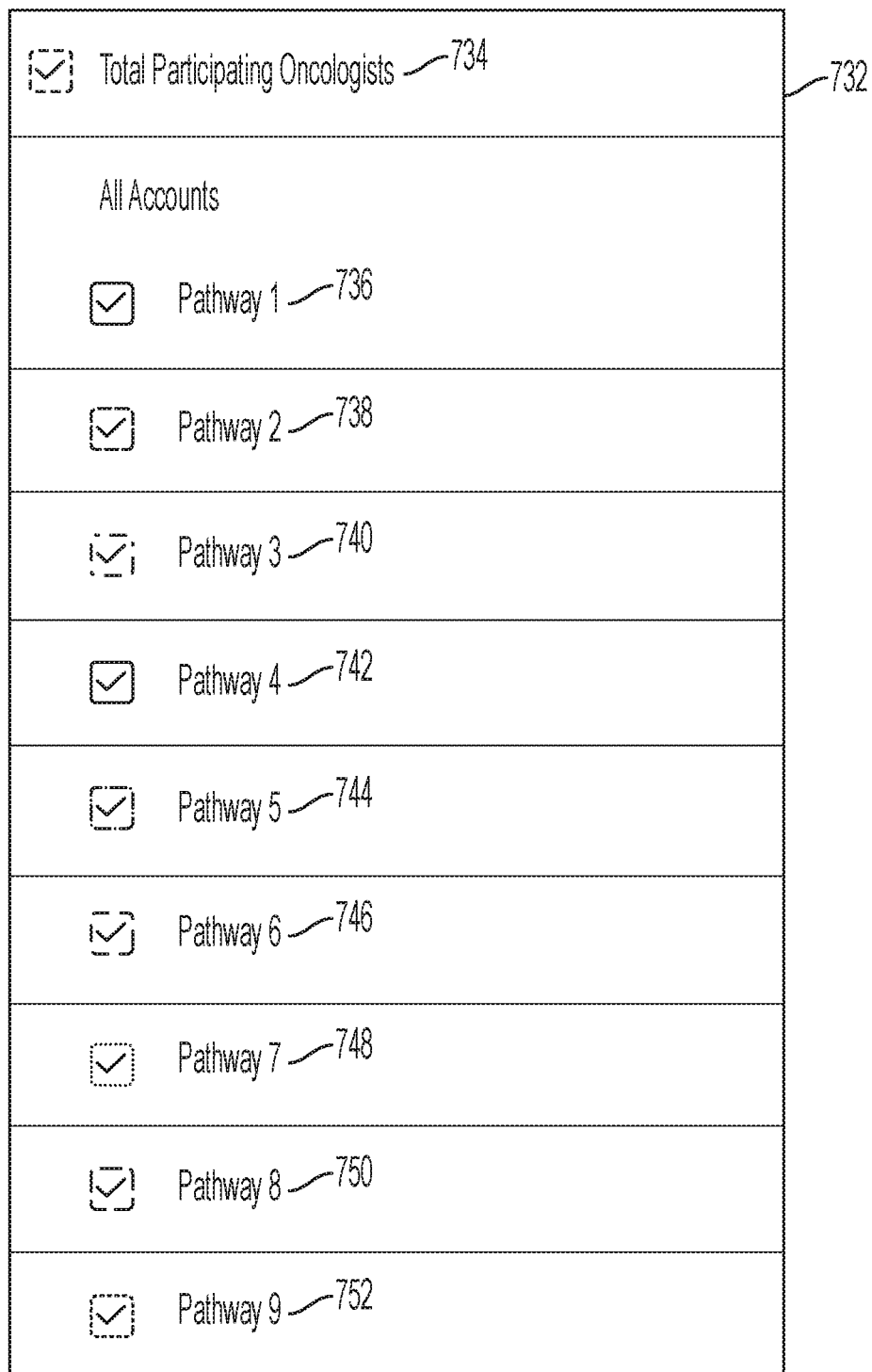

FIG. 45 is a graphical representation of a key for the pathways shown in the timeline of FIG. 44, according to at least one aspect of the present disclosure.

Figure 46:
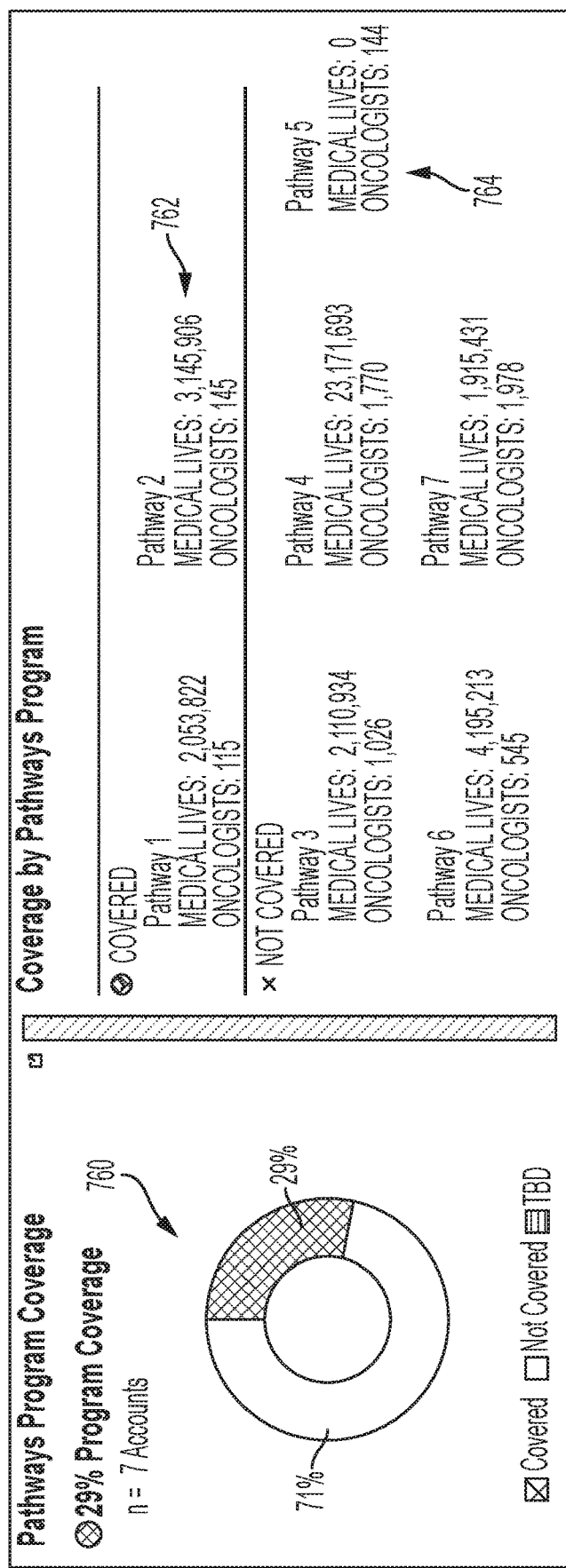

FIG. 46 is a graphical representation depicting pathway program coverage for a selected indication and listing the medical lives and oncologists for the pathway(s) by category—covered and not covered—for the Pathways & APM Tool of FIG. 5, according to at least one aspect of the present disclosure.

Figure 47:
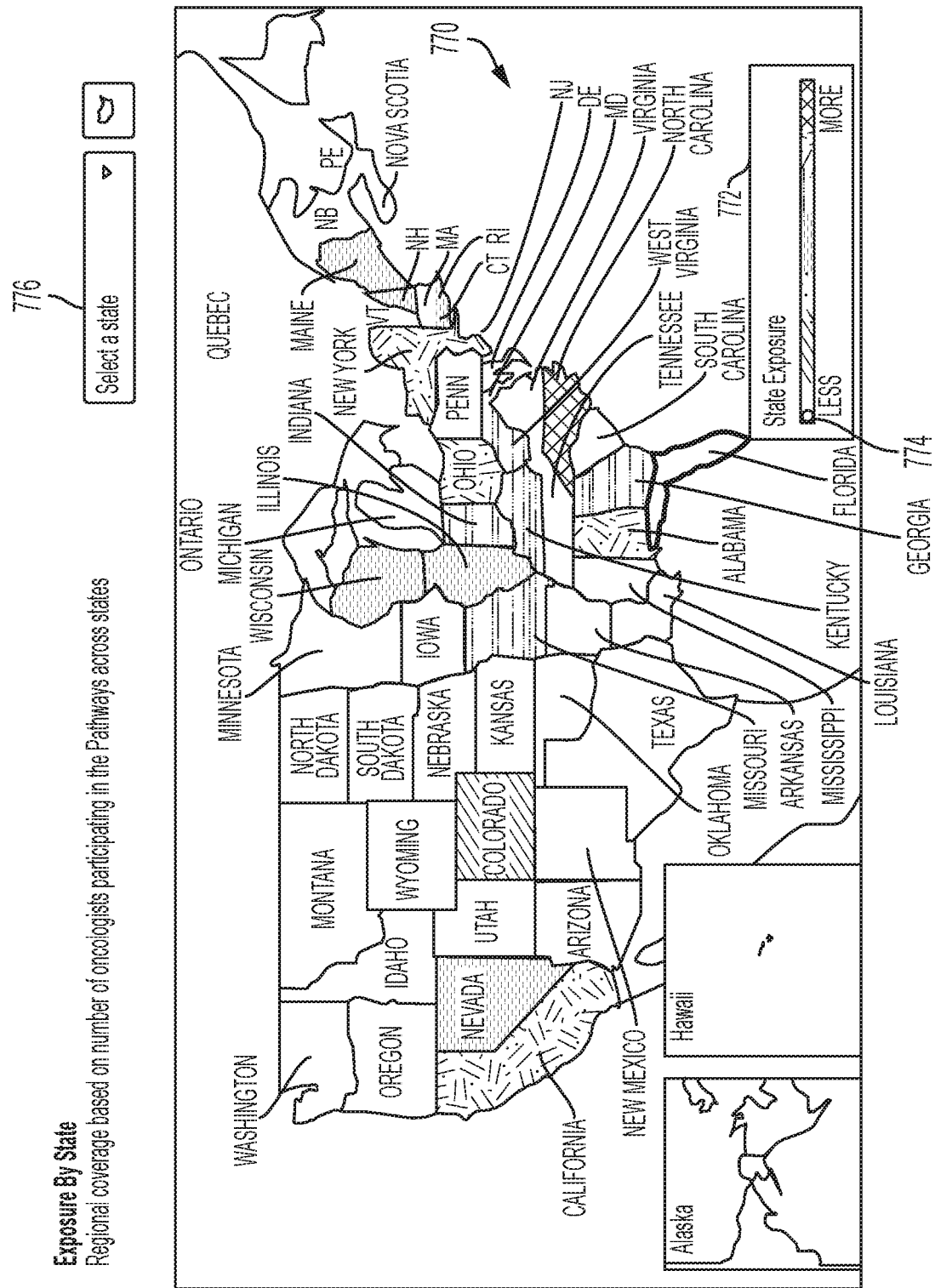

FIG. 47 is a graphical representation of a map depicting regional exposure of oncologists participating in a selected pathway for the Pathways & APM Tool of FIG. 5, according to at least one aspect of the present disclosure.

Figure 48:
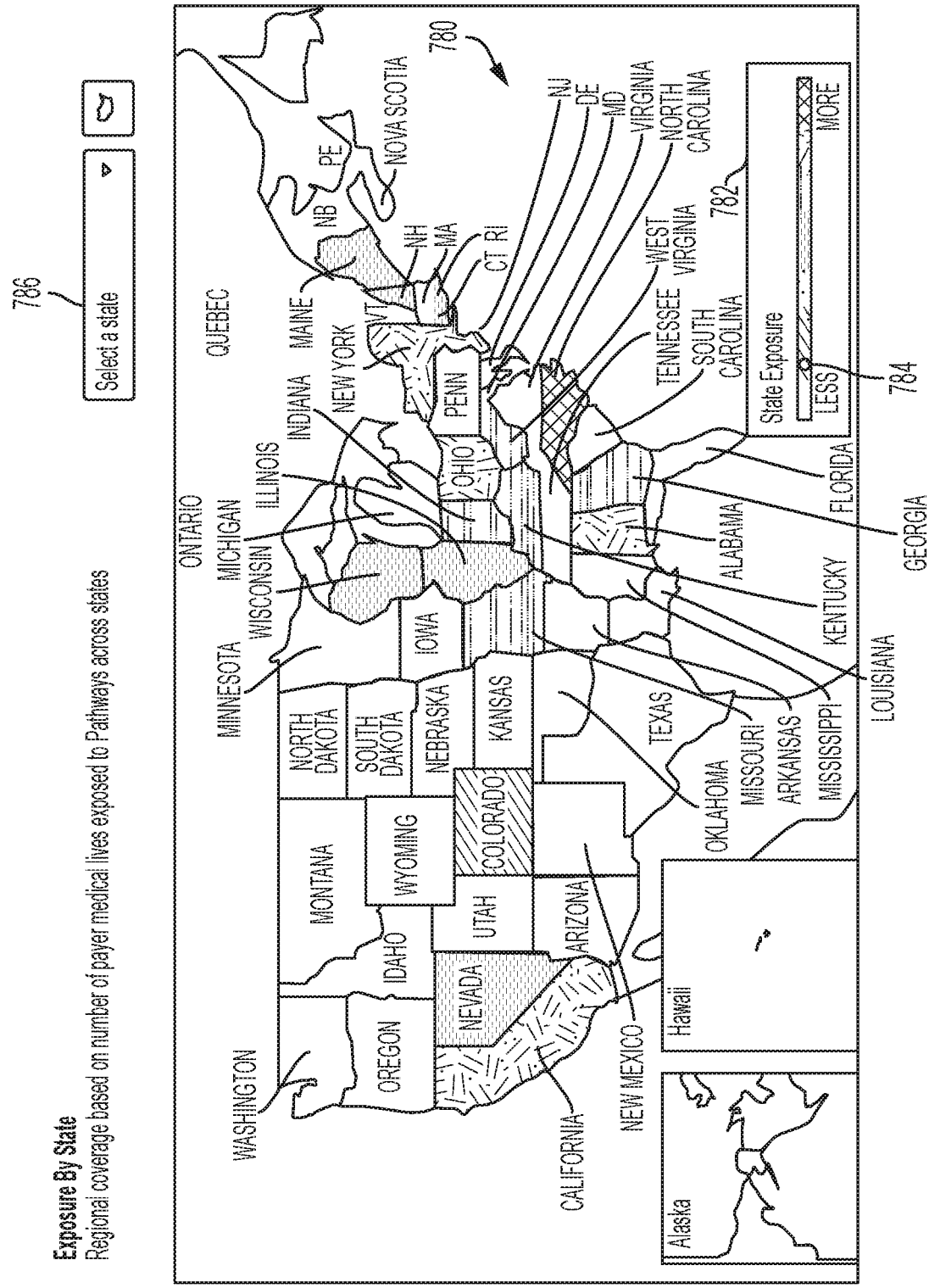

FIG. 48 is a graphical representation of a map depicting regional exposure of payer medical lives exposed to a selected pathway for the Pathways & APM Tool of FIG. 5, according to at least one aspect of the present disclosure.

FIG. 49 is a graphical representation depicting brand positioning for various products relative to FDA labels for a select pathway and indication for the Pathways & APM Tool of FIG. 5, according to at least one aspect of the present disclosure.

DETAILED DESCRIPTION

The Applicant of the present application owns the following U.S. Provisional Patent Applications that were filed on Apr. 26, 2019 and which are each herein incorporated by reference in their respective entireties:
U.S. Provisional Patent Application No. 62/839,193, entitled PAYER QUALITY OF ACCESS TOOL; and
U.S. Provisional Patent Application No. 62/839,197, entitled PROVIDER KEY ACCOUNTS TOOL; and
U.S. Provisional Patent Application No. 62/839,208, entitled THIRD PARTY PROGRAM TRANSPARENCY TOOL.

The Applicant of the present application owns the following U.S. Design patent applications that were filed on Apr. 26, 2019 and which are each herein incorporated by reference in their respective entireties:
U.S. Design patent application No. 29/689,064, entitled GRAPHICAL USER INTERFACE FOR A DISPLAY DEPICTING REGIONAL PERFORMANCE OF PROVIDERS;
U.S. Design patent application No. 29/689,065, entitled GRAPHICAL USER INTERFACE FOR A DISPLAY DEPICTING PRODUCT RESTRICTIVENESS ACROSS PROGRAMS;
U.S. Design patent application No. 29/689,076, entitled GRAPHICAL USER INTERFACE FOR A DISPLAY DEPICTING PRODUCT RESTRICTIVENESS ACROSS PAYERS; and
U.S. Design patent application No. 29/689,077, entitled GRAPHICAL USER INTERFACE FOR A DISPLAY DEPICTING SELECTION FILTERS.

The Applicant of the present application owns the following U.S. Patent Applications that were filed on Apr. 24, 2020 and which are each herein incorporated by reference in their respective entireties:
U.S. patent application Ser. No. 16/857,537, entitled PROVIDER KEY ACCOUNTS TOOL; and
U.S. patent application Ser. No. 16/857,540, entitled THIRD PARTY PROGRAM TRANSPARENCY TOOL.

Before explaining aspects of various decision-support tools in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Decision-Support Tools

Decision-support tools that provide evaluation metrics and increased transparency to payer, provider, and/or third party restrictions can improve a patient's access to helpful and/or necessary pharmaceutical products. A decision-maker may identify a source or sources of the restrictions as a payer-originating restriction, a provider-originating restriction, and/or a third party-originating restriction. Upon identifying the restrictive source(s), a decision-maker can further analyze and target the underlying concerns or origins of the restriction. For example, by determining a payer's relative quality of access by region and/or over time for a product and/or analog products, a decision-maker can target resources to the appropriate payers in an effort to reduce restrictions and increase access. Additionally, by identifying and categorizing/segmenting key providers for particular specialties, a decision-maker can target the appropriate providers in an effort to reduce restrictions and increase access. Furthermore, by determining pathway-participating providers for a particular specialty by region and/or over time, a decision-maker can target the appropriate pathways and/or APMs in an effort to reduce restrictions and increase access. These and other decision-support tools are further described herein. The comparisons, evaluation metrics, data, and/or graphical displays from the various tools described herein can improve decision-making processes and ultimately improve access of products to patients in need.

In various instances, the tools described herein can be utilized with a web-based graphical user interface in which the data can be filtered or otherwise customized to reflect the user's desired goal. For example, data can be customized to specific populations (e.g. same line of therapy, patient subtype, and/or mutation status) and/or filtered or redistributed by customizable geographical regions.

In various instances, a Payer Quality of Access (QoA) Tool can analyze the quality of access of payers. Sometimes, in efforts to save costs, payers can be unduly restrictive and limit access of an appropriate product for a patient in need. In certain instances, such as the oncology space, for example, limitations can be life threatening. The QoA Tool can provide transparency into the nuances of a payer's policy. With knowledge of the payer's policy and the restrictive aspects thereof, a decision-maker can engage the appropriate target. In other words, the Payer QoA Tool can inform payer access strategy and engagement planning priorities. For example, the decision-maker can target the payer directly to contract, educate, or provide additional data to encourage a payer to expand coverage of the product for a population to a broader level. Additionally or alternatively, the decision-maker can provide support at a provider level or for patients to address affordability and/or clinical language or eligibility concerns.

For example, the QoA Tool can compare access between payers for the same population (e.g. same indication, same line of therapy, same patient subtype, same product, and same payer type). The comparisons can improve transparency regarding which payer(s) sufficiently cover the product for each population and which payer(s) unduly restrict access to the product within each population. Restrictiveness can be evaluated by determining a payer's restrictiveness with respect to Prior Authorization (PA) and the FDA label by the payer for the population. For example, restrictiveness can be classified along a scale from less restrictive to most restrictive in the following categories: (1) the product is allowed without PA, (2) PA is less restrictive than the FDA label, (3) PA corresponds to the FDA label, (4) PA is required along with additional criteria, which may be specified or unspecified, (5) PA is more restrictive than the FDA label, and (6) the product is covered by exceptions only, i.e. the physician has to appeal the payer and fill out additional paperwork. Access changes with respect to the restrictiveness categories can be tracked to identify historical trends. Upon comparing payers and products, a Relative QoA Score can be determined, which may be disadvantaged, parity, or advantaged, for example. Additionally, geographic territories can be classified by the percentage of state lives subjected to high restrictiveness categories for the population.

Other information including review timing, treatment centers, and value-based models can also be organized and presented according to the restrictiveness categories and percentage of restricted lives. Additional features and functionalities of the Payer QoA Tool are further described herein.

In certain instances, a Provider Key Accounts (PKA) Tool can provide transparency at a local or provider level. Often, providers are subjected to their own access restriction mechanisms, such as internal protocols or pathways requirements, internal formularies, different kinds of practices, and/or different kinds of preferences. In different regions, the providers may be afforded different training opportunities and/or may have different understandings of the disease state. By understanding the roots of the provider's restrictions by way of the PKA Tool, the decision-maker can appropriately direct resources to expand utilization of the product. In other words, the PKA Tool can identify provider protocols access and field team engagement priorities. For example, if a product is not provided to certain patients due to provider restrictions, the decision-maker can implement strategies to increase utilization such as providing co-pay support, rebates, free samples, education to the provider, and/or contracting with the provider to enhance appropriate access to patients that need the product.

For example, the PKA tool can categorize key accounts (e.g. the top 100 providers of a product or treatment) into categories, such as clinical champions, restrictive integrated clinicians, streamlined operators, and decentralized physicians, for example. The key accounts can be geographically overlaid with sales data for the product or treatment. Moreover, the key accounts can be compared to each other, category averages, and/or national averages, for example. Comparisons can include market share, physician autonomy scores, and immunotherapy strength scores. Each key account can be profiled to include partnerships, key decision makers and their comparative level of influence, and operational infrastructure including internal operations, accreditations, and Centers of Excellence credentials, for example. Additional features and functionalities of the PKA Tool are further described herein.

In various instances, a Third Party Program (TPP) Tool, or Pathways and APM Tool, provides transparency to third party intermediaries between the payers and the providers. A third party intermediary (e.g. a pathway organization or APM stakeholder) can engage providers and payers to participate in a program (e.g. a pathway program and/or APM) of certain products for certain populations. For example, the third party intermediary can contract with the payers and providers and agree to reduced administrative burdens (e.g. prior authorizations) and/or to provide financial incentives (e.g. a payment to the provider for each patient that participates in the program). Such programs can be designed to treat certain populations more efficiently and, thus, save costs; however, the programs can narrow the availability of certain products and be restrictive to standardized care in certain instances. Improved transparency at the third party level with the TPP Tool can identify the appropriate targets for expanding utilization of a product. For example, the TPP Tool can facilitate understanding of sequencing and emerging value drivers on emerging APMs.

Brand positioning across various programs (e.g. pathways and APMs) can be compared according to relative access with respect to the FDA label by way of the TPP Tool. For example, relative access can be classified along a scale from less restrictive to most restrictive in the following categories: (1) advantaged, (2) parity, (3) some restrictions, and (4) off programs/pathways. The TPP Tool can also project a number of participating physicians by geographic regions and/or providers over time. Additionally, the TPP Tool can compare the medical lives and/or pharmacy lives of different programs/pathways with respect to all medical lives and/or pharmacy lives on programs/pathways over time to identify historical trends of program adoption. Each program/pathway can be profiled to include exposure by geographic region, tumor coverage, and positioning compared to the FDA-approved line of therapy, for example. Additional features and functionalities of the TPP Tool are further described herein.

In certain instances, a Regional Access and Influencers Tool can be utilized to conduct regional analyses across different groups, such as the payers, providers, and third party intermediaries. Additional features and functionalities of the Regional Access and Influencers Tool are further described herein.

In various instances, a Distribution Planning and Tracking Tool compares product manufacturers in terms of their patient and provider support programs. For example, if a first manufacturer offers copay support and programs to ease the administrative burden, a second manufacturer may be limited in distributing their products because, comparatively, the burden is higher. By identifying such differences between manufacturers, relative access concerns can be addressed. In other words, the Distribution Planning and Tracking Tool can evaluate analog trends and inform model development and/or evolution. Additional features and functionalities of the Distribution Planning and Tracking Tool are further described herein.

Finally, in certain instances, a Value and Quality Metrics Tool can map a product label to quality measures that drive reimbursement for both payers and providers. The Value and Quality Metrics Tool can benchmark attributes in comparison to competitors and quality metrics to inform value propositions and real-world evidence. For example, a United States Product Insert (USPI) can be approved by the FDA for certain indications (e.g. diagnosis and tumor-type), patient types, particular circumstances, and so on. This data can be mapped to the background information, such as clinical trial information, for example. By mapping the USPI product label to quality measures, a manufacturer can identify types of data that will enhance access to the product because, for example, it is something that has historically been covered and reimbursed by the payers. As a result, analysis with the Value & Quality Metrics Tool can improve accessibility of new products. Additional features and functionalities of the Value and Quality Metrics Tool are further described herein.

Computing Environment

The reader will readily appreciate that the various tools described herein—e.g. the Payer QoA Tool, the PKA Tool, the TPP Tool, the Regional Access and Influencers Tool, the Distribution Planning and Tracking Tool, and the Value and Quality Metric Tool—can be integrated into a central computing environment and/or can be utilized separately. Additionally, in certain instances, an integrated computing environment may utilize a selection of the tools described herein (e.g. two or more). In still other instances, additional tools can be incorporated into the computing environment for one or more of these tools.

Figure 1:
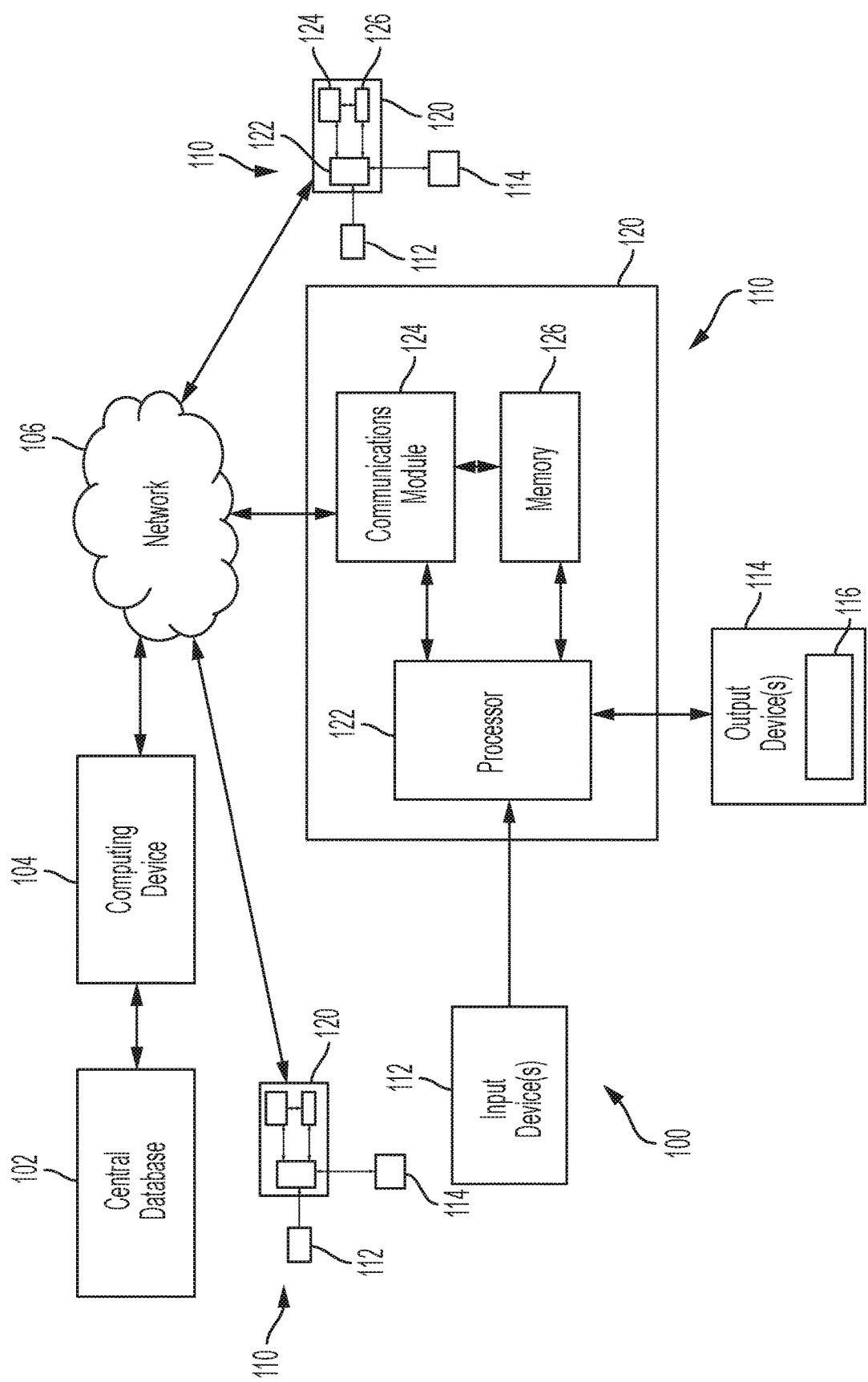
FIG. 1 is a control circuit depicting a computing environment in which data from a central database is distributed over a network, processed by way of user input devices, and conveyed to user output devices, according to at least one aspect of the present disclosure.

Referring to FIG. 1, a computing environment 100 is shown. In the computing environment 100, data from a central database 102 is distributed to user systems 110, at which the data can be processed by way of user input devices 112 and conveyed to user output devices 114. For example, data can be graphically displayed on a screen 116 of one of the output devices 114. The various graphical representations and screenshots described herein can be displayed on the screen 116, for example. The data can be provided to a computing device 104 from the central database 102 and the computing device 104 can be communicatively coupled to a network 106. The network 106 is configured to distribute the appropriate data to a designated user system 110 in accordance with subscription plans and/or access (e.g. login) credentials. In one aspect, the computing device 104 is a server and more specifically, in one aspect, the computing device 104 is a remote server. In one aspect, the network 106 is the Internet.

The user systems 110 include a computing device 120 including a processing unit 122, a communications module 124, and a memory 126. Depending on the exact configuration and type of computing device 120, the memory 126 may be volatile (such as RAM, for example), non-volatile (such as ROM, flash memory, etc., for example) or some combination thereof. The communications module 124 is configured to receive data from the network 106 and convey the data to the processing unit 122 and/or the memory 126. The processing unit 122 is configured to access data obtained over the network 106 and/or stored in the memory 126. For example, the contents of the database 102 can be accessed by the computing device 104 and the computing device 120. In one aspect, the database 102 stores the formulation data set that is used to generate the graphical data described herein and shown in various accompanying Figures. The data can be processed by the processor 122 based on inputs at the input device(s) 112 such as input to filter, sort, and/or otherwise manipulate the data. The processed data can be conveyed at the output device(s) 114 as lists, reports, tables, and/or graphical displays on the screens 116, for example. Additional inputs and outputs are further described herein. In one aspect, the computing device 120 is a client computer and more specifically, in one aspect, the computing device 120 is a local client computer coupled to the server via the network 106.

The various graphical representations described herein can be provided to the output device 114 and the screen 116 thereof. For example, the graphical representations depicted in the accompanying Figures can be screenshots of graphical representations displayed on the screen 116. The graphical representations can include tables, charts, graphs, maps, and text to convey the output analyses from the various tools in a concise and explanatory format. In certain instances, the graphical representations and/or various components thereof can be interactive, as further described herein.

In other aspects, the computing device 120 may include additional features and/or functionality. For example, the computing device 120 may include additional storage (e.g., removable and/or non-removable) including, but not limited to, magnetic storage, optical storage, and the like. In one aspect, computer readable instructions to implement one or more aspects provided herein may be stored in the additional storage. The additional storage may also store other computer readable instructions to implement an operating system, an application program, and the like. Computer readable instructions may be loaded in the memory 126 for execution by the processor 122, for example.

The term "computer readable media" as used herein includes computer storage media. Computer storage media includes volatile and nonvolatile, removable and non-removable media implemented in any method or technology for storage of information such as computer readable instructions or other data. The memory 126 and the additional storage described herein are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by the computing device 120. Computer storage media does not, however, include propagated signals. Rather, computer storage media excludes propagated signals. Any such computer storage media may be part of the computing device 120.

The communications module 124 can include one or more communication connection(s) that allows the computing device 120 to communicate with other devices such as the computing device 104. The communication connection(s) may include, but are not limited to, a modem, a Network Interface Card (NIC), an integrated network interface, a radio frequency transmitter/receiver, an infrared port, a USB connection, or other interfaces for connecting the computing device 120 to other computing devices. The communication connection(s) may include a wired connection or a wireless connection. The communication connection(s) may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

The input device(s) 112 can encompass keyboards, mice, pens, voice input devices, touch input devices, infrared cameras, video input devices, and/or any other input device. Output device(s) 114 can encompass displays, speakers, printers, and/or any other output device. The one or more input device(s) 112 and one or more output device(s) 114 can be connected to the computing device 120 via a wired connection, wireless connection, or any combination thereof. In one aspect, an input device or an output device from another computing device may be used as the input device(s) 112 or the output device(s) 114 for the computing device 120.

Components of the computing device 120 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another aspect, components of the computing device 120 may be interconnected by a device network. For example, the memory 126 may be comprised of multiple physical memory units located in different physical locations interconnected by a device network.

Storage devices utilized to store computer readable instructions may be distributed across the network 106. For example, the computing device 104 accessible via the network 106 can store computer readable instructions to implement one or more aspects provided herein. The computing device 120 may access the computing device 104 and download a part or all of the computer readable instructions for execution. Alternatively, the computing device 120 can download pieces of the computer readable instructions, as needed, or some instructions may be executed at the computing device 120 and some at the computing device 104.

The computing device 104 may include all or some of the components of the computing device 120. For example, in one aspect, the computing device 104 includes at least one processing unit and a memory, e.g., a volatile memory (such as RAM, for example), a non-volatile memory (such as ROM, flash memory, etc., for example) or some combination of the two. In other aspects, the computing device 104 may include additional storage (e.g., removable and/or non-removable) including, but not limited to, magnetic storage, optical storage, and the like. In one aspect, computer readable instructions to implement one or more aspects provided herein may be stored in the storage. The storage also may store other computer readable instructions to implement an operating system, an application program, and the like. Computer readable instructions may be loaded in the memory for execution by the computing device 104, for example.

The computing device 104 can also include one or more communication connection(s) that allows the computing device 104 to communicate with other devices such as the computing device 120. The communication connection(s) may include, but are not limited to, a modem, a Network Interface Card (NIC), an integrated network interface, a radio frequency transmitter/receiver, an infrared port, a USB connection, or other interfaces for connecting the computing device 104 to other computing devices. The communication connection(s) may include a wired connection or a wireless connection. The communication connection(s) may transmit and/or receive communication media.

The computing device 104 may include one or more input device(s) such as a keyboard, mouse, pen, voice input device, touch input device, infrared cameras, video input devices, and/or any other input device. Output input device(s) such as one or more displays, speakers, printers, and/or any other output device may also be included in the computing device 104. The one or more input device(s) and one or more output device(s) may be connected to the computing device 104 via a wired connection, wireless connection, or any combination thereof. In one aspect, an input device or an output device from another computing device may be used as the input device(s) or the output device(s) for the computing device 104.

Components of the computing device 104 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another aspect, components of the computing device 104 may be interconnected by a device network. For example, the memory may be comprised of multiple physical memory units located in different physical locations interconnected by a device network.

Figure 2:
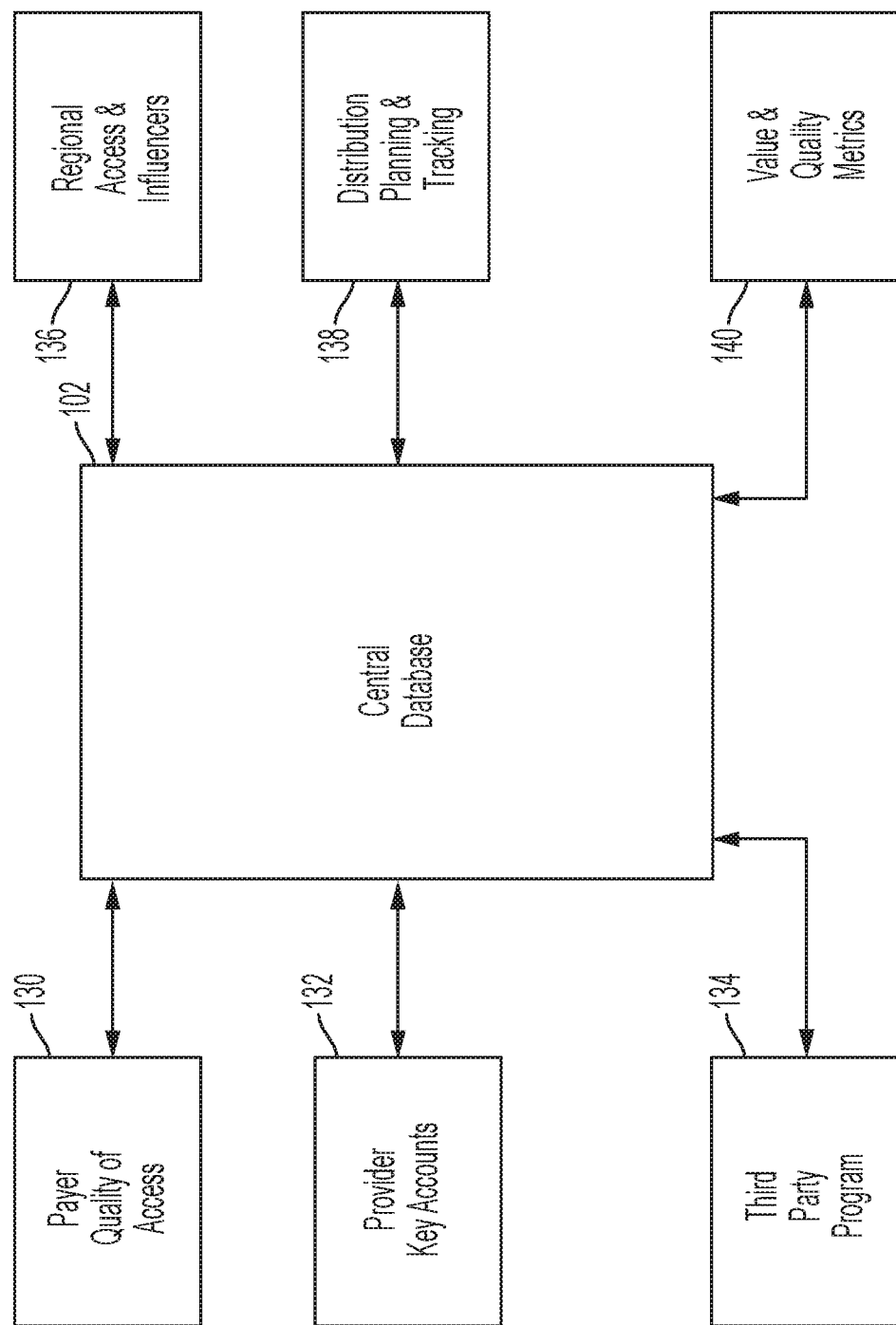
FIG. 2 is a diagram depicting the flow of information between multiple tools by way of the central database of FIG. 1, according to at least one aspect of the present disclosure.

Referring now to FIG. 2, the central database 102 is shown communicatively coupled to multiple tools, including a Payer QoA Tool 130, a PKA Tool 132, a TPP Tool 134, a Regional Access & Influencers Tool 136, a Distribution Planning & Tracking Tool 138, and a Value & Quality Metric Tool 140. In various instances, data can flow from multiple tools to and from the central database 102. In such instances, data can be shared between the tools and utilized as necessary for the functionality thereof. In certain instances, the tools can include tool-specific databases, as well. Additionally or alternatively, the tools can be communicatively coupled to each other and, in essence, the communication therebetween can form a central database for communicating with the computing device 104 and/or the network 106 (FIG. 1), for example.

Figure 3:
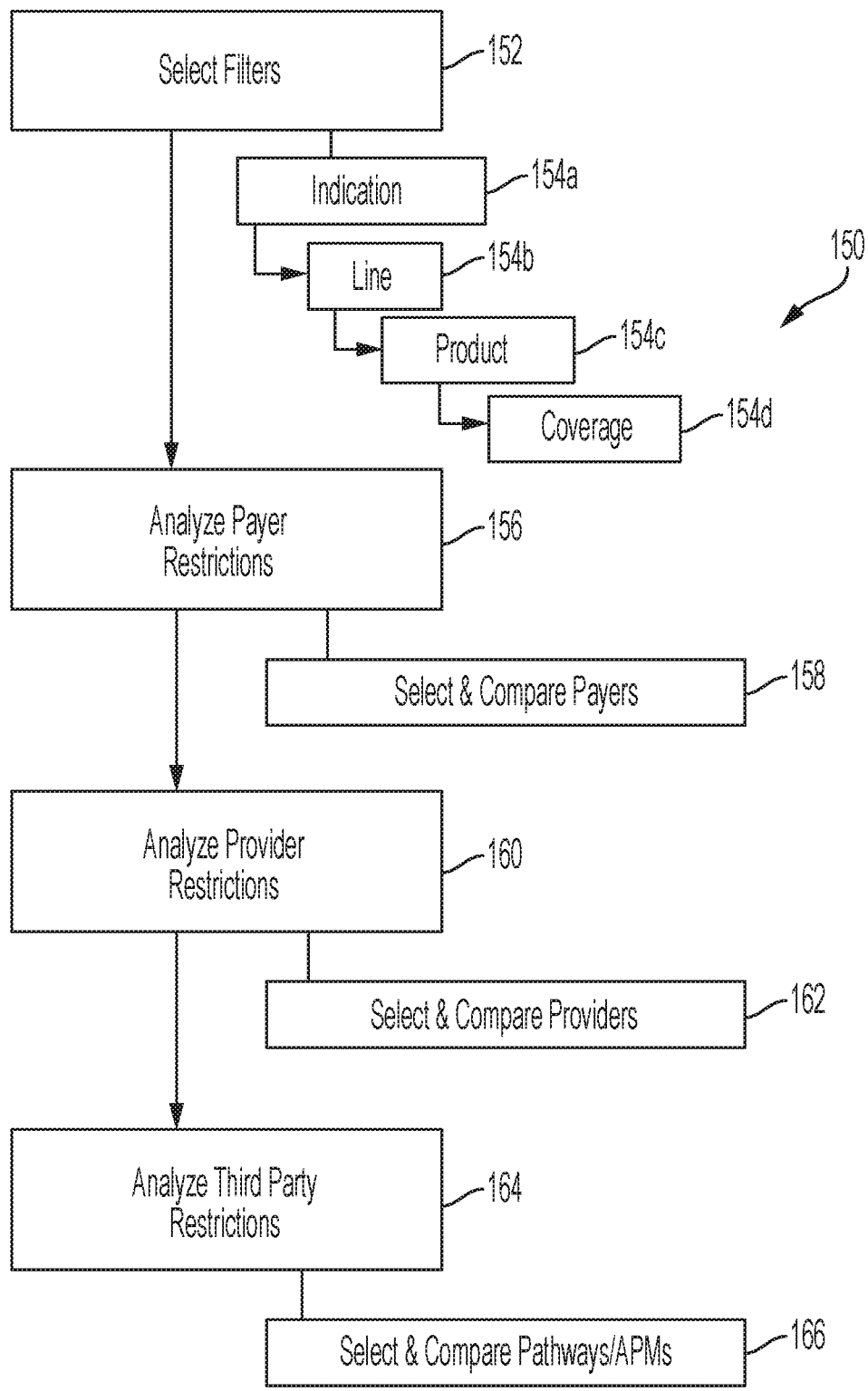
FIG. 3 is a logic diagram depicting steps to aid a decision-maker in the allocation of resources to improve access to products and/or expand utilization of products, according to at least one aspect of the present disclosure.

A logic diagram 150 is shown in FIG. 3. In various instances, the computing environment 100 can be utilized for the logic diagram 150. At block 152, filters can be selected. Filters can define a population and can include an indication 154a, a line of therapy 154b, a product 154c, and coverage type 154d, for example. Other filters include coverage filter and/or patient sub-type filter, for example. Thereafter, payer restrictions can be analyzed at block 156 with the Payer QoA Tool 130 (FIG. 2), for example, provider restrictions can be analyzed at block 160 with the PKA Tool 132 (FIG. 2), for example, and/or third party restrictions can be analyzed at block 164 with the TPP Tool 134 (FIG. 2), for example. The blocks 156, 160, and 164 can be completed in a different order and, in certain instances, analyses may only be completed at one or two of the blocks 156, 160, and 164. In other instances, additional analyses can be incorporated into the logic diagram 150. To analyze payer restrictions at block 156, payers can be selected and compared at block 158, for example. To analyze provider restrictions at block 160, providers can be selected and compared at block 162. To analyze third party restrictions at block 164, pathways and/or APMs can be selected and compared at block 166. The logic diagram 150 is configured to aid a decision-maker in the allocation of resources (e.g. time and money), to improve access to products, and/or utilization of products based on restrictions imposed by the payers, providers, and/or third party intermediaries, for example. Filtering schemes can be employed to filter the content based on the selections elected at blocks 156, 160, and 164, for example.

Referring now to FIG. 4, a table 170 is shown that depicts exemplary data sources or inputs for the Payer QoA Tool 130, the PKA Tool 132, and the TPP Tool 134. The data sources can be classified as secondary data 172 in a first row, analog data 174 in a second row, or third party data 176 in a third row.

Secondary data 172 for the Payer QoA Tool 130 can include, for example, published medical percentages for pharmacy payer policies, including Medicare Administrative Contract (MAC) National Coverage Determinations (NCD) and Local Coverage Determinations (LCD) policies Part B, payer prior authorization forms and formularies, payer published new-to-market coverage policies, payer provider billing and coding manuals, payer provider bulletins and manuals, payer and Centers for Medicare & Medicaid (CMS) Part D, payer published networks of Specialty Pharmacy Providers (SPPs), payer press releases, 10-Ks, 10Qs, and investor presentations.

Analog data 174 for the Payer QoA Tool 130 can include, for example, payer enrollment surveys and discussions, payer contracting discussions, provider/payer discussions on restrictive utilization management profiling, provider/practice manager/specialty pharmacy hub discussions, analog claims data (such as industry data sources), SPPs RFIs of letters of agreement (medical and pharmacy), and Pathways and APM Tracker™.

Third party data 176 for the Payer QoA Tool 130 can include, for example, industry payer lives reconciliation/validation via industry data sources and manufacturer regions sales/account executive alignment.

Secondary data 172 for the PKA Tool 132 can include, for example, provider websites and press releases, provider annual reports, information from clinical trials (e.g. clinicaltrials.gov), GPO/practice management society membership, society memberships (e.g. National Comprehensive Cancer Network [NCCN], National Cancer Institute [NCI], American Society of Clinical Oncology [ASCO], and Hematology/Oncology Pharmacy Association [HOPA]), CMS EMR meaningful use data, CMS physician claims/remittance forms, and Healthcare Cost and Utilization Project (HCUP) payer mix claims data.

Analog data 174 for the PKA Tool 132 can include, for example, provider/pharmacy/nursing/pathology discussions, GPO discussions (e.g. ION, Onmark, and Vitalsource), Integrated Delivery Network (IDN) provider/dispensing network discussions, EMR and value-based care vendor discussions (e.g. Excelera and Acentrus), EMR and value-based care vendor discussions, provider/pathologist/MDx vendor discussions (e.g. LabCorp and Foundation Medicine), Pathways and APM Tracker™, and GPO & Contracting Tracker™.

Third party data 176 for the PKA Tool 132 can include, for example, manufacturer account-level sales data (e.g. industry data sources), manufacturer clinical trials/Key Opinion Leader (KOL) sites, and manufacturer regional sales/account executive alignment.

Secondary data 172 for the TPP Tool 134 can include, for example, published pathways positions, press releases on provider/payer partnerships, peer-reviewed literature on In cost-savings impact/results, pathways/value-based model published review processes, data submission options and meeting dates, and American Medical Associate (AMA) provider datasets.

Analog data 174 for the TPP Tool 134 can include, for example, participating provider pathways/APM positioning discussions, Pathways & APM Tracker™, pathways and value-based care vendor RFI capabilities and presentations.

Third party data 176 for the TPP Tool 134 can include, for example, manufacturer regional sales/account executive alignment, for example.

In various instances, data from one source can be utilized across multiple tools, such as the Pathways & APM Tracker™ data source, which can be utilized by the Payer QoA Tool 130, the PKA Tool 132, and the TPP Tool 134. Manufacturing regional sales/account executive alignment data sources are also shared between these three tools 130, 132, and 134. The reader will readily appreciate that additional data can be shared between one or more of the various tools described herein. For example, one or more outputs from the various tools can be shared between tools. For example, a quality of access classification from the Payer QoA Tool 130 can be shared with one or more other tools and/or a provider account segmentation/category classification from the PKA Tool 132 can be shared with one or more other tools.

FIG. 5 depicts a graphical user interface for an integrated decision-support portal 200, such as a portal that provides access to one or more of the tools 130, 132, 134, 136, 138, and/or 140 of FIG. 2. The graphical user interface can be provided to one or more of the output devices 114 of FIG. 1 by the processor 122 of the corresponding computing device 120, which can be communicatively coupled to the central database 102 via the computing device 104 and/or the network 106, as further described herein. In various instances, the portal 200 can be utilized in the logical diagram 150 of FIG. 3. The portal 200 provides access to the following tools: a Payer QoA Tool 230, which can correspond to the Payer QoA Tool 130, for example; a PKA Tool 232, which can correspond to the PKA Tool 132, for example; a Pathways and APM or TPP Tool 234, which can correspond to the TPP Tool 134, for example; a Regional Access and Influencers Tool 236, which can correspond to the Regional Access and Influencers Tool 136, for example; a Distribution Planning & Tracking Tool 238, which can correspond to the Distribution Planning & Tracking Tool 138, for example; and a Value and Quality Metric Tool 240, which can correspond to the Value and Quality Metric Tool 140, for example. A user can select the desired tool 230, 232, 234, 236, 238, and/or 240, which can be linked through the portal 200, to filter the content accessible via the portal 200.

The Regional Access and Influencers Tool 236 can prioritize local opportunities that strengthen access and provider value perception, for example. The Distribution Planning & Tracking Tool 238 can evaluate analog distribution and dispensing trends to inform model development or evolution, for example. The Value and Quality Metrics Tool 240 can identify quality-based insights to support value proposition development, real-world evidence, and pricing and contracting, for example. Additional strategic access and value enhancement metrics, data, and analysis with respect to the tools 230, 232, 234, 236, 238, and 240 accessible via the portal 200 are further described herein.

Payer Quality of Access Tool

Payers, providers, and third parties intermediaries can present a complex web of interested parties with different motivations and/or interests leading to complex relationships therebetween. The involvement and degree of interplay between these groups can vary depending on the field. With respect to oncology and other specialty therapeutics, the payers, providers, and third parties intermediaries can be especially involved due to the high stakes from a cost and patient health perspective. In such circumstances, an increased level of sophistication and management can be required of the payers, for example, because traditional PA processes and/or step edits may be less effective. For example, it can be challenging to understand which PA processes are actually burdensome or stringent in practice in view of the complex relationships governing accessibility to a product. The various restrictions can be specific to a particular product and/or indication. Restrictions can narrow the potential patient population having access to the product.

The Payer QoA Tool 230 is structured to provide transparency into payer-specific restrictions for particular products and/or indications and insight into the reach of such restrictions, as well as the underlying causes. The Payer QoA Tool 230 can inform payer access strategies, competitive landscape analysis, and engagement planning priorities, for example.

The Payer QoA Tool 230 can enable conversion of qualitative data to quantitative data for purposes of comparison and graphical/visual analyses to facilitate payer quality of access analysis of at least one pharmaceutical product. Quantitative metrics can allow comparison across payers and populations, for example. In certain instances, the comparisons can be based on a filtering scheme and at least one filter selected by an end user. Restrictiveness and the corresponding restriction category can be a quantitative metric. In one example, the restrictiveness can be determined by comparing a payers preauthorization requirement(s) with a regulatory label, such as Food and Drug Association label, for example.

In one instance, the Payer QoA Tool 230 can be a strategic decision support tool for analyzing payer quality of access for at least one pharmaceutical product and can include a remote database storing content related to payer policies and comparative metrics for the at least one pharmaceutical product, a remote server configured to access content stored in the remote database, and a local device coupled to the remote server by a network, wherein the local device comprises an input tool and a display. In certain aspects of the Payer QoA Tool 230, in response to a filter selected with the input tool and communicated to the remote server across the network, the remote server is configured to extract policy criteria from a first payer policy based on the filter selected with the input tool, extract comparative metrics based on the filter selected with the input tool, compare the extracted policy criteria to the extracted comparative metrics, assign, based on the comparison, a restrictiveness score, generate a graphical representation of the restrictiveness score, display the graphical representation via a graphical user interface on the display to facilitate payer quality of access analysis of the at least one pharmaceutical product.

To further facilitate the analysis of the at least one pharmaceutical product, the Payer QoA Tool 230 can repeat the comparative analysis for multiple pharmaceutical products and multiple payer policies. Filtering of the products and/or payers can occur according to pharmaceutical product, indication, line of therapy, patient sub-type, type of payer, coverage, geographic territory, and various combinations thereof. Various features and functions of the Payer QoA Tool 230 are further described herein.

Figure 6:
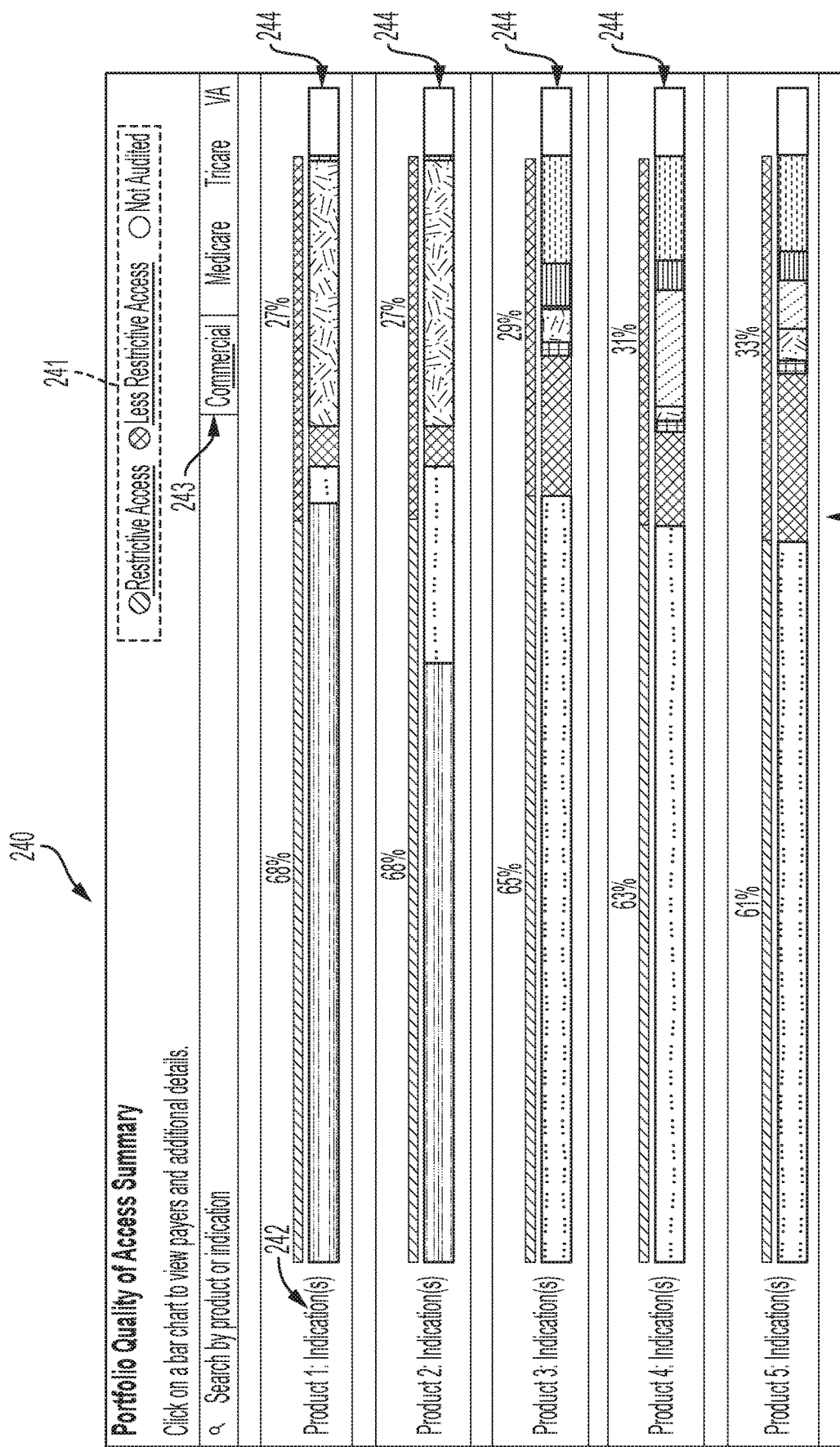
FIG. 6 is a graphical representation depicting a portfolio quality of access summary for the Payer Quality of Access Tool of FIG. 5 to compare product accessibility for selected payer types (e.g. across commercial payers per the "Commercial" selection indicated in FIG. 6), according to at least one aspect of the present disclosure.

Referring to FIG. 6, a graphical representation of a portfolio quality of access summary 240 for the Payer QoA Tool 230 is shown. The portfolio quality of access summary 240 provides a snapshot comparison of product accessibility for a payer type selected by a type of payer filter 243 (e.g. commercial insurance, Medicare, Tricare, and VA). For example, commercial insurers are selected in FIG. 6. The content can be filtered based on the selection(s), such as product, indication, and coverage type, for example. A list 242 of products and indications is also provided. Each product in the list 242 has a corresponding graph 244, which presents the breakdown of lives subjected to a general restriction category—"restrictive access", "less restrictive access", or "not audited". A key 241 indicates the general restriction categories depicted in the graphs 244.

Figure 7:
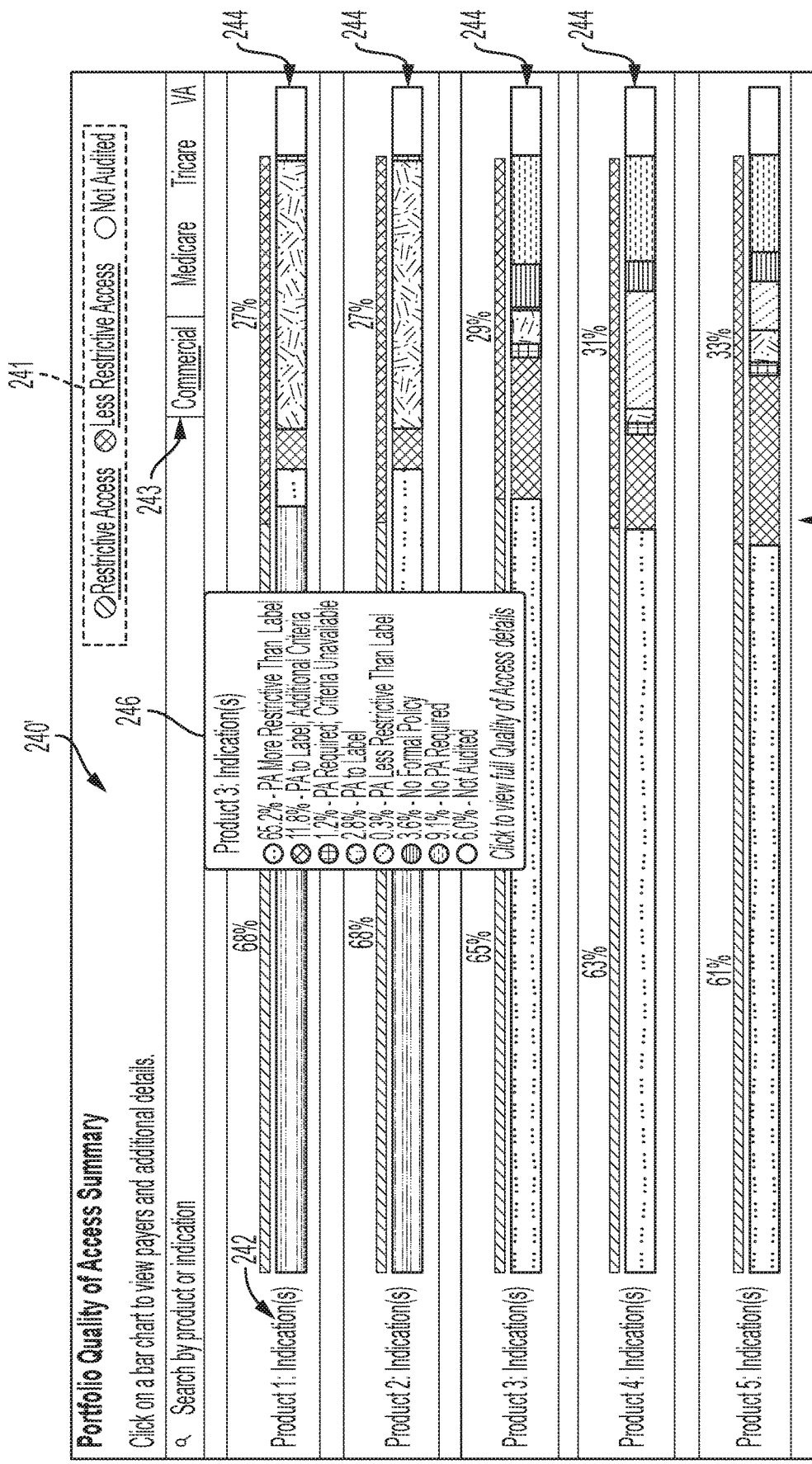
FIG. 7 is a graphical representation depicting the portfolio quality of access summary of FIG. 6 and including a pop-up display of additional accessibility data for a selected product and indication, according to at least one aspect of the present disclosure.

Exemplary general restriction categories and subcategories thereof are graphically depicted along parallel bars for each graph 244. By hovering a cursor over one of the graphs 244, additional details 246 can be provided regarding the accessibility data for the selected product and indication. For example, referring to FIG. 7, the quality of access summary 240' includes additional details regarding the relevant subcategories for the selected graph 244, which corresponds to Product 3 in the list 242. In this particular example for Product 3 in FIG. 7, the quality of access summary 240' presents the percentage of lives subjected to the following subcategory for "restrictive access": PA more restrictive than the FDA label. The quality of access summary 240' in FIG. 7 also presents the percentage of lives subjected to the following subcategories of "less restrictive access": PA to FDA label and additional criteria, PA required and criteria unavailable, PA to FDA label, PA less restrictive than the FDA label, no formal policy, and no PA required. In other words, policy criteria can be compared to comparative metrics, such as the metrics set forth by a regulatory authority like the FDA, for example. Based on the comparison with the comparative metrics, the restrictiveness score can be determined.

From the quality of access summaries 240 and 240', the user can determine the quality of coverage for a particular disease area in conjunction with the manufacturer of a product. In other words, the summaries 240 and 240' can convey insights into a payer policy in terms of restrictiveness. Additionally, the information presented in the summaries 240 and 240' is linked and structured on the backend, based on the different filters such as the type of payer, payer name/identity, product, indication, patient sub-type, and line of therapy. In various instances, additional filters can include mutation status and/or patient subtype, for example. Such filters allow the Payer QoA Tool 230 to dynamically compare products for the same population and the same line of therapy, for example. An exemplary graphical user interface for depicting selection filters is further shown in U.S. Design patent application No. 29/689,077, entitled GRAPHICAL USER INTERFACE FOR A DISPLAY DEPICTING SELECTION FILTERS, which was filed Apr. 26, 2019.

Classification of a product and indication into the categories and subcategories in the summaries 240 and 240' can be determined by a number of factors including provider network input on the type of criteria that is stringent, restrictions extracted from the policy document, and historical denial data. The foregoing data can be obtained from a number of sources, including different kinds of providers, distributors and/or dispensers, especially pharmacies, for example, for oral pharmaceuticals. Data sources are further described with respect to FIG. 4, for example.

Figure 8:
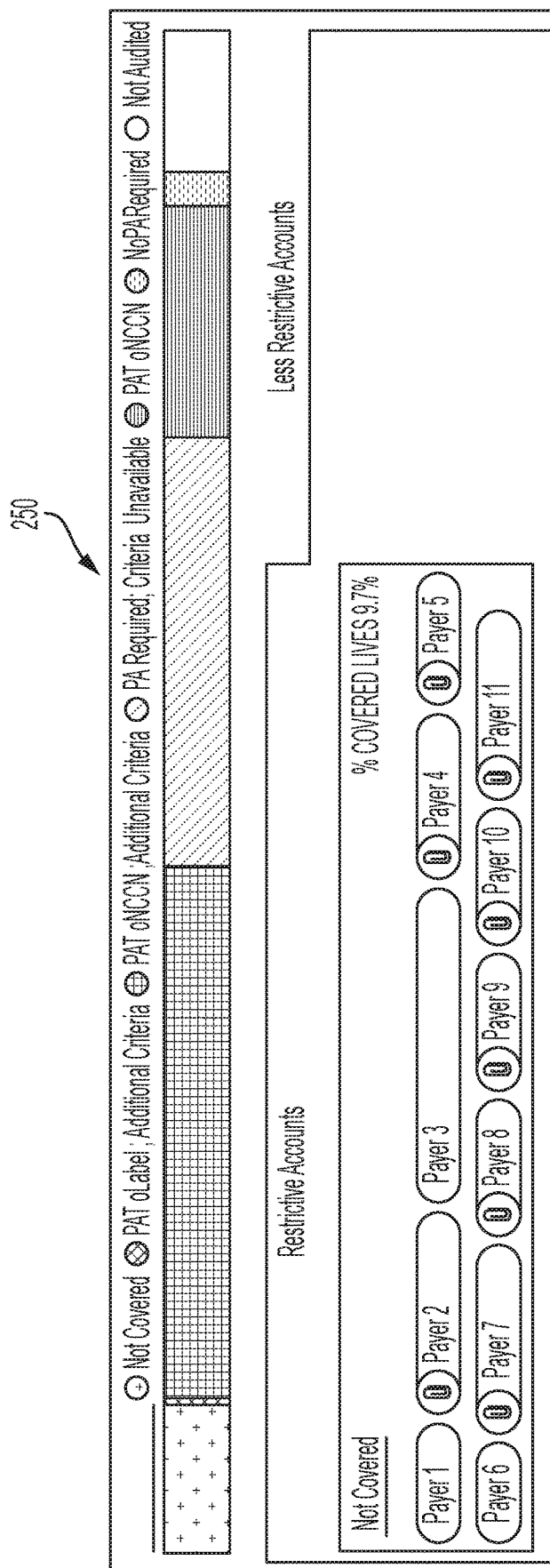
FIG. 8 is a graphical representation depicting a quality of access analysis for the Payer Quality of Access Tool of FIG. 5 and highlighting restrictive accounts for a population, according to at least one aspect of the present disclosure.
Figure 9:
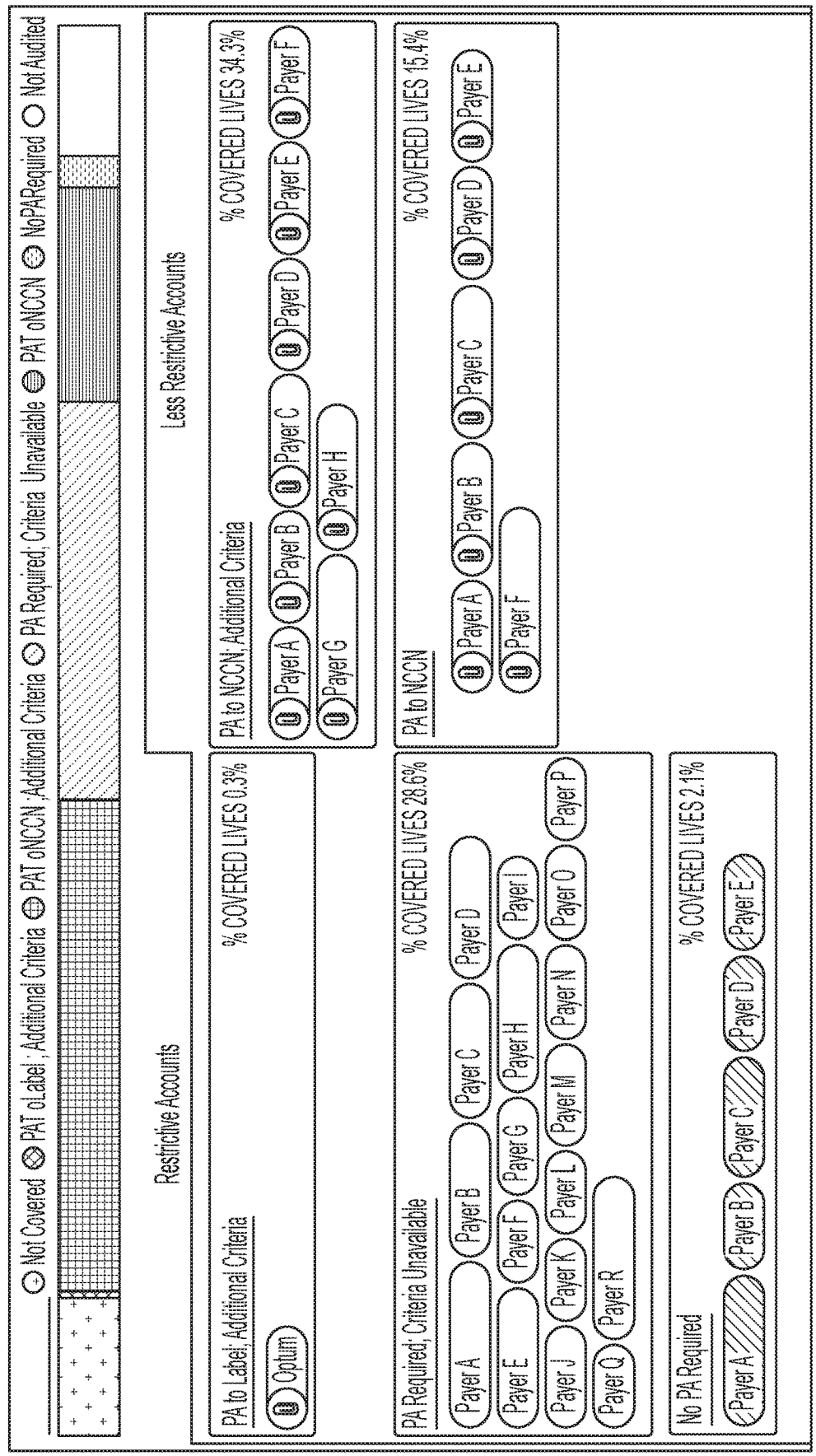
FIG. 9 is a graphical representation depicting the quality of access analysis of FIG. 8 and highlighting less restrictive accounts for the population, according to at least one aspect of the present disclosure.

Referring now to FIGS. 8 and 9, for each product and indication for a type of payer, a quality of access analysis 250 (FIG. 8), 250' (FIG. 9) can be provided by the Payer QoA Tool 230. For example, the analysis 250 can apply to a specific product and indication in the summaries 240, 240'. The quality of access analysis 250 highlights restrictive accounts for a population and the quality of access analysis 250' highlights less restrictive accounts for the population. Payer accounts can be linked in the quality of access analyses 250, 250' such that the user can access the payer policies and summaries of the policy criteria that are restrictive and non-restrictive. For example, requiring the submission of medical records and documentation of a mutation status can be considered more stringent or restrictive criteria because other payers may only require documentation of diagnosis in these circumstances. Moreover, the summary can highlight non-restrictive criteria, such as the age and counseling requirements that are consistent with the standard of care for the population. A link to download or send (e.g. email) the payer policy and/or policy criteria can also be provided in the quality of access analyses 250, 250'.

In various instances, the policy criteria can be developed in connection with proactive surveillance of the payer policies. For example, upon updating and/or revising of a payer policy, an alert can be provided to a team of analysts. The alert can also highlight the sections or portions (e.g. by page number and/or line) of the document policy that have been revised. The team of analysts can then analyze the document, especially the revised portions thereof, to determine the extent of the revisions and update the policy criteria in the Payer QoA Tool 230 accordingly.

Referring now to FIG. 10, policy criteria 262 for determining the quality of payer access can be sorted according to prevalence (e.g. percentage of pharmacy coverage) and filtered by restrictiveness (e.g. restrictive criteria or less restrictive criteria) in a table 260. For example, the policy criteria 262 related to quantity limits, age requirements, approval duration, and others, can be listed in the table 260. Additionally, the payer accounts with a particular policy criteria can be accessible by links 264 in the table 260, which can provide access to the corresponding payer policy and/or policy criteria summaries described herein.

Figure 11:
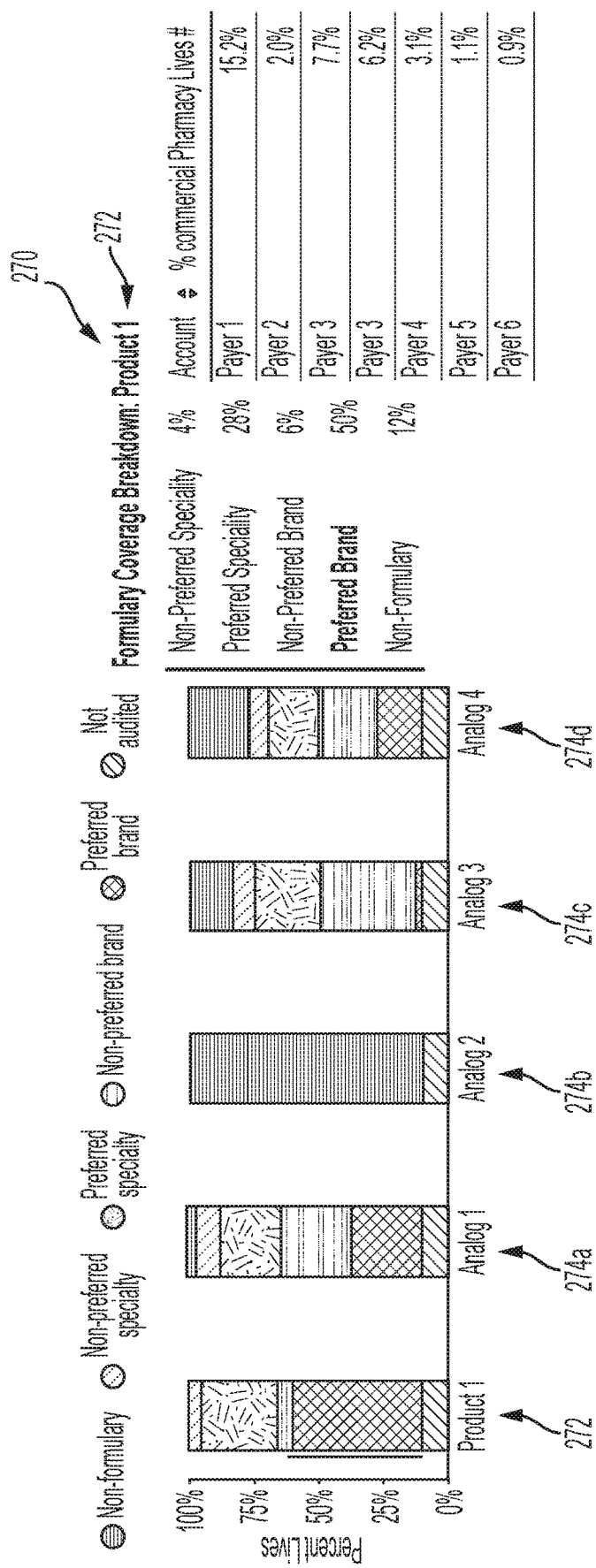
FIG. 11 is a graphical representation depicting comparative formulary coverage information for various products and payers for the Payer Quality of Access Tool of FIG. 5, according to at least one aspect of the present disclosure.

A comparative formulary coverage analysis 270 for the Payer QoA Tool 230 is shown in FIG. 11. The analysis 270 compares a product 272 to analog products 274a, 274b, 274c, and 274d with respect to pharmacy lives for which the products are designated as a non-formulary product, non-preferred specialty product, preferred specialty product, non-preferred brand product, preferred brand product, or non-audited. Moreover, for each product 272, the payer accounts and percentage of pharmacy lives can be sorted by prevalence, for example.

Figure 12:
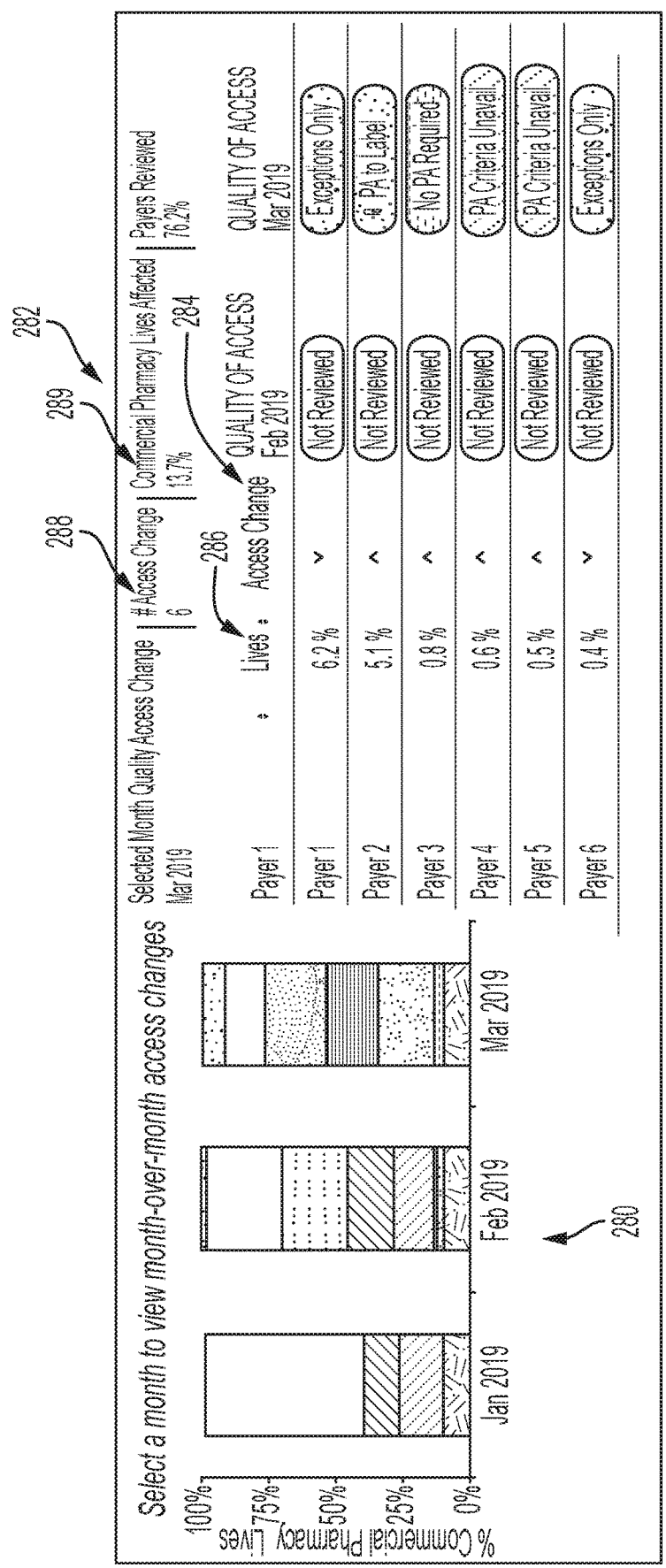
FIG. 12 is a graphical representation depicting historical trends with respect to quality of access for the Payer Quality of Access Tool of FIG. 5, according to at least one aspect of the present disclosure.

Referring now to FIG. 12, the Payer QoA Tool 230 can also provide historical trending information with respect to payer's quality of access for a population. For example, for a selected population (e.g. indication, line of therapy, product, and payer type), the percentage of commercial pharmacy lives in each restrictiveness classification (such as (1) the product is allowed without PA, (2) PA is less restrictive than the FDA label, (3) PA corresponds to the FDA label, (4) PA is required along with additional criteria, which may be specified or unspecified, (5) PA is more restrictive than the FDA label, (6) the product is covered by exceptions only, and (7) not reviewed) can be graphically presented for multiple time periods (e.g. monthly, quarterly, annually and so on) in a plot 280. By hovering and/or clicking on the bar graph in the plot 280 for each time period, additional data can be displayed, such as a classification key and the various percentages allocated to each classification.

FIG. 12 also includes a table 282 that summarizes the access changes for the entire population and each payer over time. For example, an access change indicator is listed in a first column 284 in which an indication is provided for each payer in the table 282. Indications can include a positive change, negative change, or neutral/no change, for example. The list of payers can be arranged in decreasing order based on the number of pharmacy lives affected by the change. The percentage of affected pharmacy lives is listed in a second column 286. The table 282 also indicates the current quality of access for each payer in a third column 285. With respect to the entire population, the table 282 indicates the number of access changes 288 and percentage of pharmacy lives affected 289, among other things.

In various instances, the Payer QoA Tool 230 is also configured to provide relative quality of access comparisons between products (e.g. analog products). In various instances, restrictiveness is informed by historical analog restrictions and supported by significantly lower utilization of analog products with similar types of restrictions. If an analog product having similar types of restrictions has a greater utilization within a population or other filter, the relative quality of access score can indicate a reduced quality of access for the product in comparison to the analog(s). Such an analysis can inform a decision-makers strategies and/or targets to increase utilization of the product.

For a product and an analog product, the Payer QoA Tool 230 can determine the number of pharmacy lives that are disadvantaged, advantaged, or at parity based on the payer policies. In this instance, the policy criteria from the payer policies can be compared for each product and each policy within a set of payer policies (e.g. top payer policies for a population and/or region) can be designated as "disadvantaged", "advantaged" or at "parity", for example, with respect to another policy for the product. Furthermore, the policy criteria can be weighted such that the designations (disadvantaged, advantaged, and/or at parity) can be scaled according to the weight and a relative quality of access score can be provided for each payer upon comparing the product and the analog product.

Figure 13:
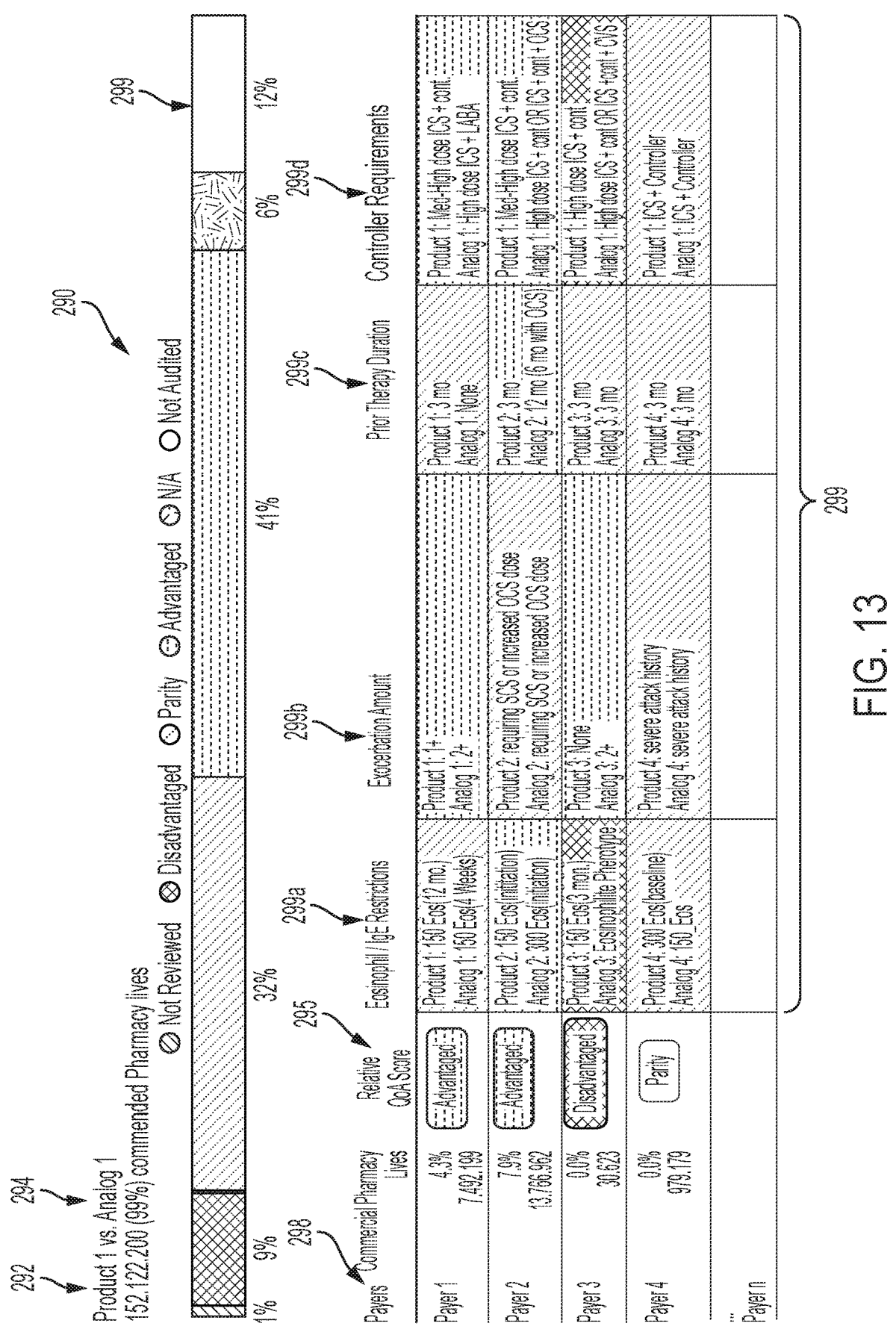

For example, referring now to FIG. 13, a relative quality of access analysis 290 is depicted. The analysis 290 compares a product 292 to an analog product 294 across a population. The percentage of pharmacy lives that are disadvantaged, advantaged, or at parity based on the payer policies are shown in the graph 296. To determine a Relative Quality of Access Score 295 of disadvantaged, advantaged, or at parity, policy criteria comparisons 299 in a table 298 are utilized. For each payer listed in the table 298, the table 298 also includes the percentage of pharmacy lives affected (e.g. the beneficiaries of each payer policy), the Relative Quality of Access Score 295, and the policy criteria comparisons 299 utilized to compute the Relative Quality of Access Score 295. The analysis 290 and the table 298 can provide a snapshot across all payers regarding whether the product is advantaged, disadvantaged, or at parity with an analog product.

For example, for Payer 1, the policy criteria comparisons 299 indicate a net positive score in favor of the Product 294. For example, the policy criteria 299*a*, 299*b*, 299*c*, and 299*d* are compared and classified as disadvantaged, advantaged, or at parity. The policy criteria 299*a*, 299*b*, 299*c*, and 299*d* can be extracted from the payer policies, as further described herein. Exemplary policy criteria 262 are shown in FIG. 10 and include, for example, restrictions with respect to quantity limits, age requirements, approval duration, and others. The classification of each policy criteria 299*a*, 299*b*, 299*c*, and 299*d* can be indicated by coding (e.g. color-coding and/or shading) of the cell in the table 298. For example, a comparison of the first policy criteria 299*a* for Payer 1 indicates parity, a comparison of the second policy criteria 299*b* for Payer 1 indicates an advantage for the product 292, a comparison of the third policy criteria 299*c* for Payer 1 indicates parity, and a comparison of the fourth policy criteria 299*d* for Payer 1 indicates an advantage for the product 292. The Relative Quality of Access Score 295 for Payer 1 is advantaged, which is computed by aggregating and, in certain instances, weighing the comparisons of each policy criteria 299*a*, 299*b*, 299*c*, and 299*d*. In certain instances, the policy criteria 299*a*, 299*b*, 299*c*, and 299*d* can be averaged to determine the Relative Quality of Access Score 295.

Figure 13A:
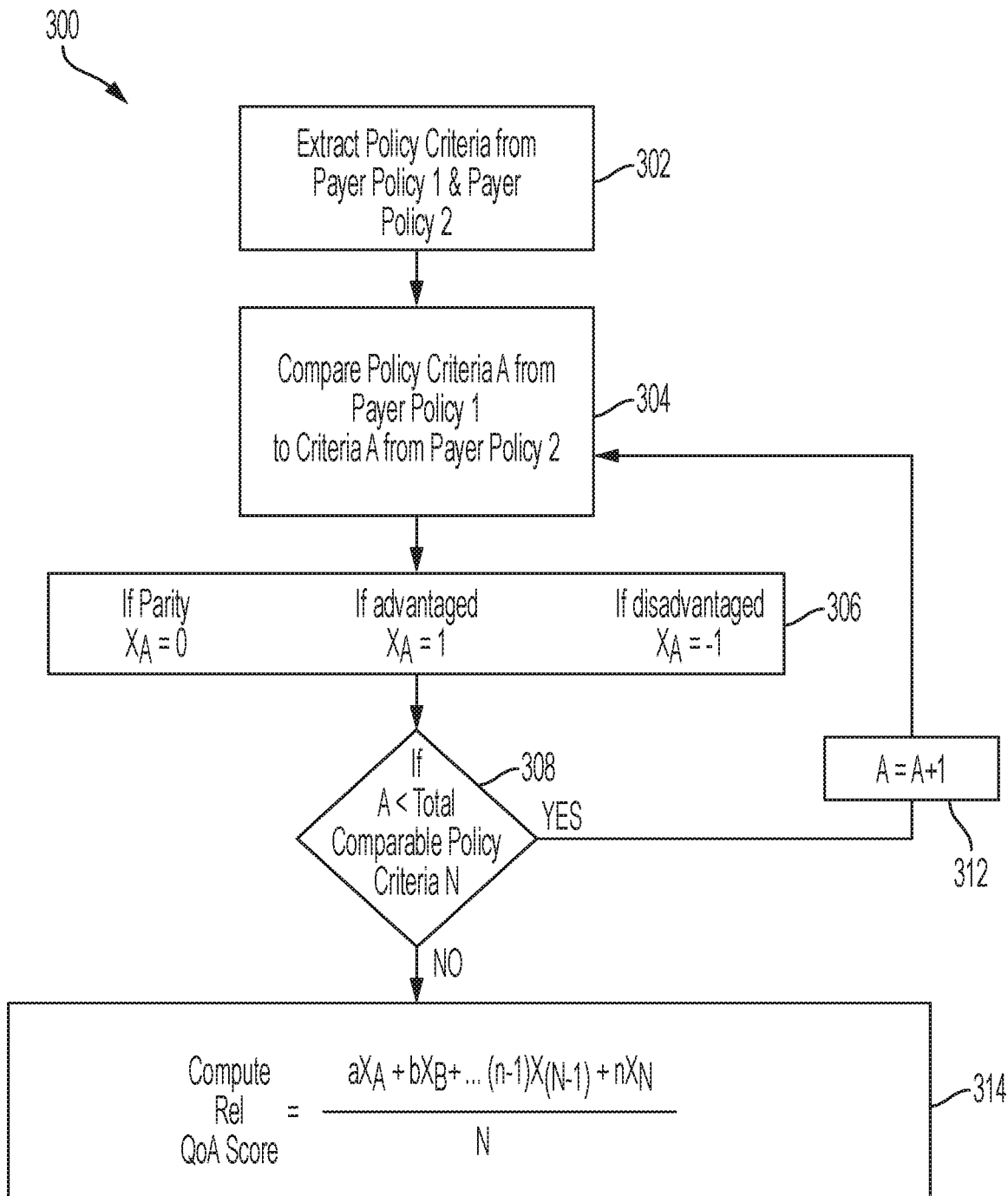
FIG. 13A is a logic diagram depicting steps to compute a relative quality of access score for the relative quality of access analyses of FIG. 13, according to at least one aspect of the present disclosure.

An exemplary logic flowchart 300 for the relative quality of analysis 290 is depicted in FIG. 13A. In various instances, the logic flowchart 300 can be utilized by the computing environment 100 (FIG. 1). At block 302, the policy criteria can be extracted from the payer policies. At block 304, the policy criteria can be compared. For example, when A=1, a first policy criteria of Payer Policy 1 (e.g. criteria 299*a* in FIG. 13) can be compared to a corresponding first policy criteria of Payer Policy 2. The policy criteria value x can be set at block 306 to 0, 1, or −1 based on the comparison. For example, if the comparison yields a neutral result (i.e. equal/parity), the first policy criteria value can be set to zero, if the comparison yields an advantaged result, the first policy criteria value can be set to 1, and if the comparison yields a disadvantaged result, the first policy criteria value can be set to −1. Thereafter, if it is determined that remaining policy criteria remain to be compared (block 308), A can be incremented at block 312 to compare another policy criteria (e.g. criteria 299*b* in FIG. 13) of Payer Policy 1 with the comparable policy criteria of Payer Policy 2 to determine the other policy criteria values. A can be incrementally increased until all of the policy criteria of Payer Policy 1 are compared with the comparable policy criteria of Payer Policy 2. Upon comparing all of the comparable policy criteria, the Relative Quality of Access Score can be computed at block 314. In at least one aspect, the Relative Quality of Access Score can be computed by scaling or weighing the policy criteria values of zero, positive one, and negative one according to predefined variables for each policy criteria. In other instances, policy criteria values can be averaged (e.g. the variables [a, b, n−1, n] can be equal).

In various instances, by determining the Relative Quality of Access Scores and percentage of pharmacy lives categorized by each Score, a decision-maker, such as a manufacturer, pharmaceutical company, and/or biotech company, for example, can determine which payers are most restrictive and in which ways, as well as determining the number of pharmacy lives and market share affected by the restrictiveness. Moreover, by determining the ways in which a payer is restrictive, the analysis can indicate to a decision-maker the root(s) of the restrictiveness—if there is a burden on providers with respect to paperwork or other administrative burdens or hurdles, for example, and/or if there is a burden on patients with respect to out-of-pocket expenses, for example, and/or if there is a burden on pharmacies with respect to dispensing a pharmaceutical and/or fulfilling compliance requirements (e.g. compliance calls) to keep patients adherent to a subscription, for example.

Figure 14:
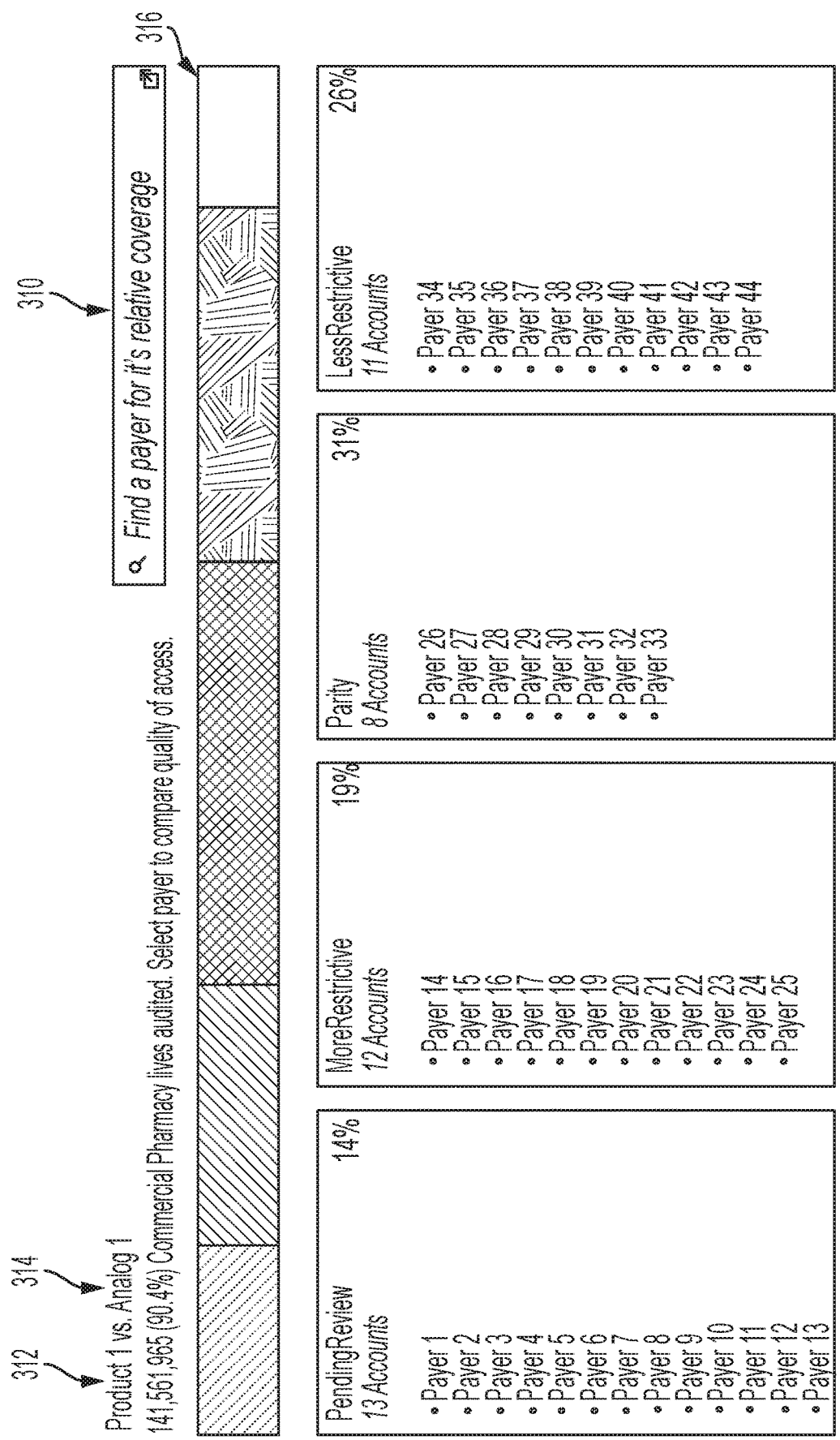
FIG. 14 is a graphical representation depicting accessibility analyses for competitive products for the Payer Quality of Access Tool of FIG. 5, according to at least one aspect of the present disclosure.

An exemplary competitive access analysis 310 for competitive products by the Payer QoA Tool 230 is shown in FIG. 14. Similar to the analysis 290 (FIG. 13), the analysis 310 compares a product 312 to an analog product 314 across a population. The percentage of pharmacy lives that are disadvantaged, advantaged, or at parity based on the payer policies are shown in the graph 316. The graphical user interface also includes search functionality tool 311 for quickly accessing additional information on a specific payer. Additionally, the payer accounts are listed in categories according to their Quality of Access Score ("More Restrictive", "Parity", "Less Restrictive", and "Pending Review"). Additional information regarding each payer can be provided by a hyperlink and/or pop-up at their name, for example.

Figure 15:
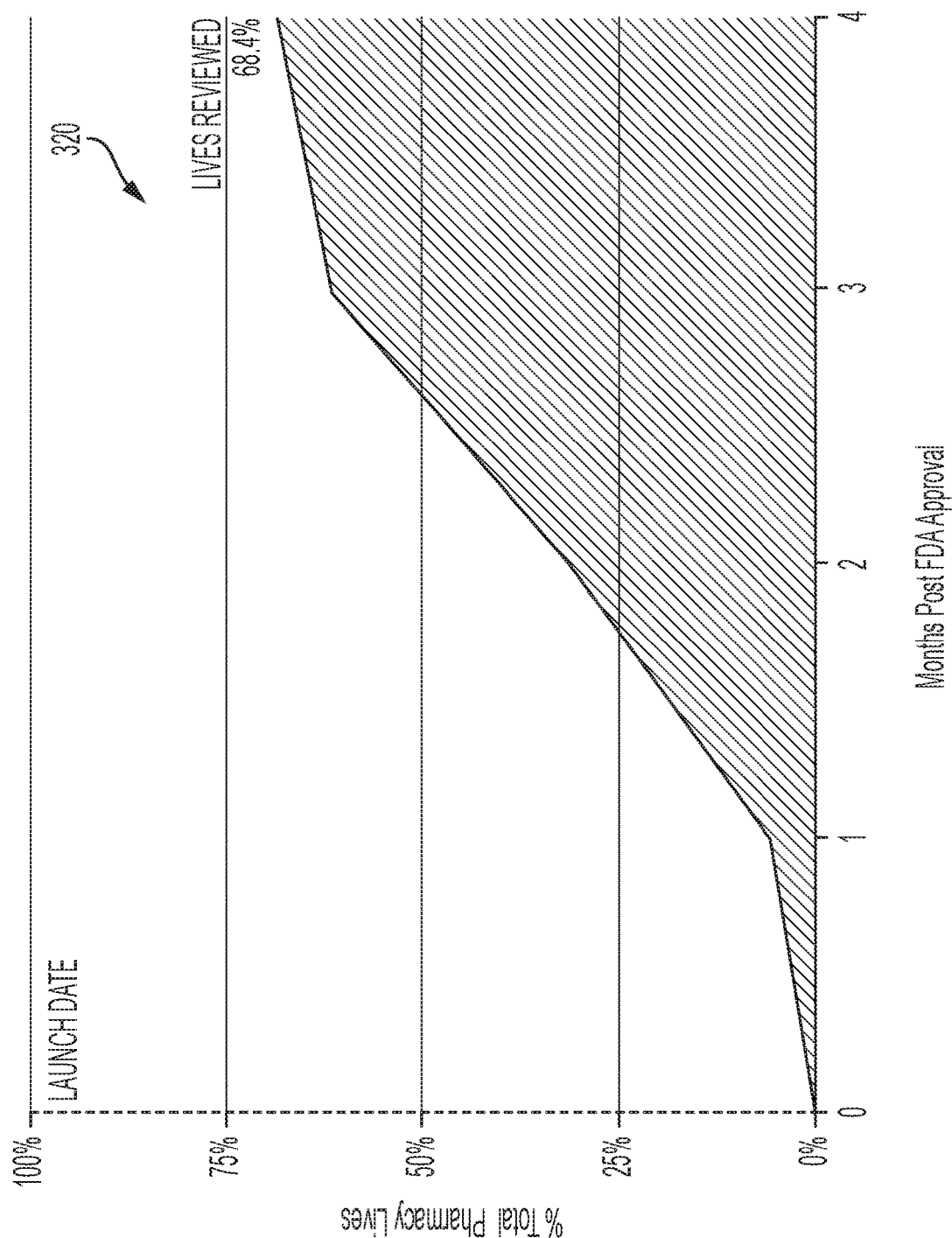
FIG. 15 is a graphical representation depicting historical trends for the Payer Quality of Access Tool of FIG. 5, according to at least one aspect of the present disclosure.

Referring now to FIG. 15, a graphical representation 320 depicting historical trends for the Payer QoA Tool 230 is shown. The graphical representation 320 shows percentage of total pharmacy lives for a population over time, i.e. months post-FDA approval. For example, at time t=0, 0% of pharmacy lives were impacted by the product. However, at time t=four months post FDA-approval, 68% of pharmacy lives were impacted by the product. A pharmacy life is impacted by the product when the payer has reviewed and developed a policy for the product. In other words, at four months post FDA-approval, the payers who developed a policy for the product covered 68% of pharmacy lives. This indicates how quickly a product can be adopted and can be utilized to better forecast or predict review and adoption timing for an analog product, for example.

Additionally, in various instances, the graphical representation 320 can be overlaid with market event timing. For example, meetings by organizations that effect implementation of a product can be overlaid with the graphical representation. As an example, meetings and/or approval dates by the NCCN can be overlaid for products targeting cancer therapies. In such instances, a decision-maker can evaluate the reach of a product as measured from different points in time. Payers often follow and/or make decisions with respect to their policies based, at least in part, on inputs from the NCCN. Additionally or alternatively, the graphical representations can be classified with respect to product attributes, such as order to market for a particular indication, for example. Such product attribute classifications can help decision-makers identify comparable products and, thus, forecast payer development (e.g. review and policy making) before a product is launched.

In various instances, the Payer QoA Tool can also analyze data regarding providers that prescribe a product. For example, the tool can automatically align coverage policies to the location of the main providers or treatment centers that prescribe a product. In other words, the tool can integrate information regarding payer policies with provider data, for example, from the PKA Tool 232 (FIG. 5), which can help a decision-maker identify if a restriction originates at a provider and/or a payer source.

Figure 16:
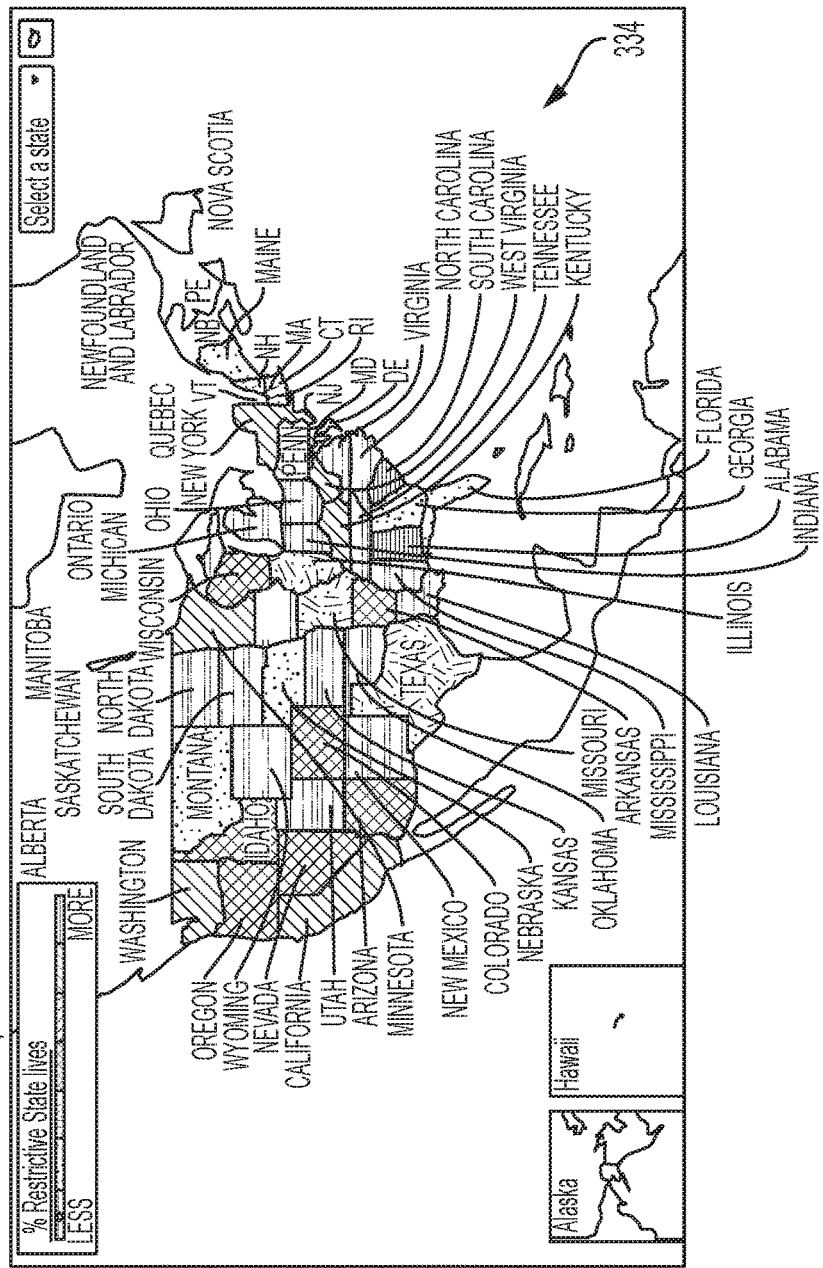
FIG. 16 is a graphical representation of regional targeting analyses for the Payer Quality of Access Tool of FIG. 5, according to at least one aspect of the present disclosure.

Referring now to FIG. 16, a graphical representation 330 of a regional targeting analysis is shown for the Payer QoA Tool 230. The graphical representation 330 provides a regional view in which parts of a map 334 (the United States of America in FIG. 16) where access is restricted are highlighted. The type and/or amount of highlighting, greyscale, shading, and/or a spectrum of color(s), for example, can depend on the degree of restrictiveness and can be indicated with a key 332. For example, for a particular jurisdiction (e.g. a state or region) an algorithm can weigh the quality of access based on the mix of payers in that jurisdiction. For example, the degree of restrictiveness of each payer can be weighed based on the percentage of pharmacy lives in that jurisdiction to provide an overall restrictiveness ranking along a restrictiveness spectrum (e.g. the spectrum indicated in the key 332). Furthermore, the jurisdictions are listed in order of decreasing restrictiveness along the restrictiveness spectrum in a table 336.

In various instances, the graphical representation 330 can be tailored based on the epidemiology of the patient population. For example, based on the patient demographic in a particular jurisdiction, the percentage of state lives can be adjusted to reflect how many potential patients reside in the jurisdiction. In such instances, the potential patients in a region—given the epidemiology and/or demographics of the region—can be overlaid with the restrictiveness based on the mix of payers in the region.

Additionally or alternatively, the regional targeting graphical representation 330 can be customized based on a sales force region. For example, jurisdictions on the map can be drawn in accordance with provided sales force region boundaries and the degree of restrictiveness for that sales force region can be determined based on the mix of payers in the region. The pharmacy lives can be redistributed based on the sales force region and the percentage of restricted pharmacy lives in that region can be recalculated. A sales force region can be defined by one or more geographic territories and/or zip codes, for example. For example, a sales force region can be defined as a West Coast region that includes Washington, California, Colorado, and the states in between.

In various instances, value-based care models can influence the accessibility of a product by a payer. A value-based care model encompasses third party intermediaries that work with providers and payers to manage the overall quality of care as well as cost. A value-based care model, such as a pathway program or APM for oncology, for example, may not be aligned with a payer's policy. By analyzing payer participation in value-based models, a decision-maker can identify a target payer and/or third party intermediary (e.g. pathway organization) to improve accessibility. Value-based care models are often non-transparent and, thus, it is especially challenging to decipher the effect of the models and the barriers they pose to appropriate access.

A pathway program, or clinical pathway, can provide a way to standardize the clinical approach to using therapeutics. Pathway programs are determined by third party intermediaries but can be sanctioned by payers and/or may start in a provider organization as a way to manage risk. If a patient has particular attributes or situations, a preferred protocol or pathway program can be suggested. In certain instances, subscribing to a pathway can preclude a provider from spending extra time on the phone with the payer, reduce administrative dollars, limit fights with the payer, and/or avoid incidences of billing through a PA. Additionally or alternatively, subscribing to a pathway may provide a provider with a payment upon completion of the pathway program. In other words, there can be a cost or revenue element attributed to adherence to a pathway program, which can provide a way for payers to manage providers by encouraging the self-policing of the providers. Particularly in areas like oncology, where explicit management by a payer is less desirable because the patients may be terminally-ill, for example, the payers may not want to have very restrictive policies; however, they can make the administrative burden very high and implement value-based care models, like pathway programs, for example, to manage risk. On the other hand, providers may also want to manage risk with respect to getting reimbursed for certain products and, thus can be motivated to stick to a pathway that ensures reimbursement without fighting a PA appeal, for example. The interconnectedness of the payers and providers, often via the third-party intermediaries, such as pathways, are often non-transparent to manufacturers who are trying to increase accessibility of a product to a larger population.

Figures 17, 18:
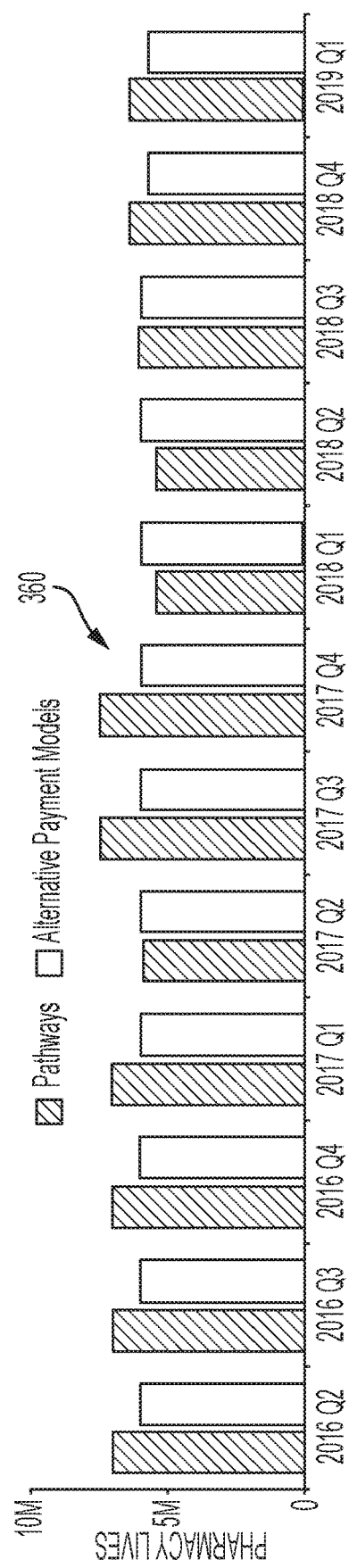
FIG. 17 is a graphical representation of value-based models utilization by pharmacy lives over time for a population for the Payer Quality of Access Tool of FIG. 5, according to at least one aspect of the present disclosure.
FIG. 18 is a graphical representation of a table depicting utilization of value-based models by pharmacy lives for a population and corresponding quality of access classifications for the payers for the Payer Quality of Access Tool of FIG. 5, according to at least one aspect of the present disclosure.

In various instances, the Payer QoA Tool 230 can be configured to track the payers that participate in pathways or APM and convey what percentage of pharmacy lives participate over time (e.g. quarterly and/or annually). For example, referring to FIG. 17, a graphical representation 360 of value-based models utilization by pharmacy lives over time for a population is shown. Moreover, referring now to FIG. 18, for the payers participating in a value-based model, the Payer QoA Tool 230 can highlight the restrictiveness of the participating-payers (e.g. relative to an FDA line) and determine whether the payer's policy is aligned with the value-based model, such as in a table 362. For example, for a particular population (e.g. indication, product, line of therapy, and coverage type), Payer 1 in the table 362 participates in one pathway, covers over 3 million pharmacy lives, and the quality of access is categorized as "not covered". Additionally, alignment of the payer policy can be determined by selecting the icon 363 for "View Alignment", which shows, in FIG. 19, pathway positioning data 364 for the population. In this example, Pathway 1, also does not utilize the product. Alternatively, if Pathway 1 suggested the product for the population consistent with the payer policy, the payer's policy and the pathway would be designated as "aligned" in the positioning data 364.

In another aspect, for a different population, the payer's quality of access may be "PA is more restrictive than label" and the payer may participate in a pathway in which additional criteria are required before the product is suggested for treatment and, thus, the criteria for the policy and the pathway are different. In one instance, the pathway can be more restrictive than the payer policy. The foregoing analyses can integrate payer quality of access with value-based models to determine whether the accessibility is aligned or not. When it is aligned, it may signify that the payer is trying multiple ways to achieve the same goal in terms of managing cost and care for a particular therapy and a particular indication area versus when the payer policy is not aligned with the value-based model, which may signal a disconnect in the goals of the payer and the value-based model stakeholder, for example.

In various instances, referring again to FIG. 5, the Payer QoA Tool 230 can also include a Payer Account Dashboard 233 that provides account information for specific accounts covered by the tool 230. For example, whereas the analyses and data of FIGS. 6-19 generally provide a top-down management perspective via a Management Dashboard 231 of the quality of access of payers across different populations, products, and/or geographic regions, for example, the Payer Account Dashboard 233 can provide a focused profile for each payer account.

Figures 19, 20:
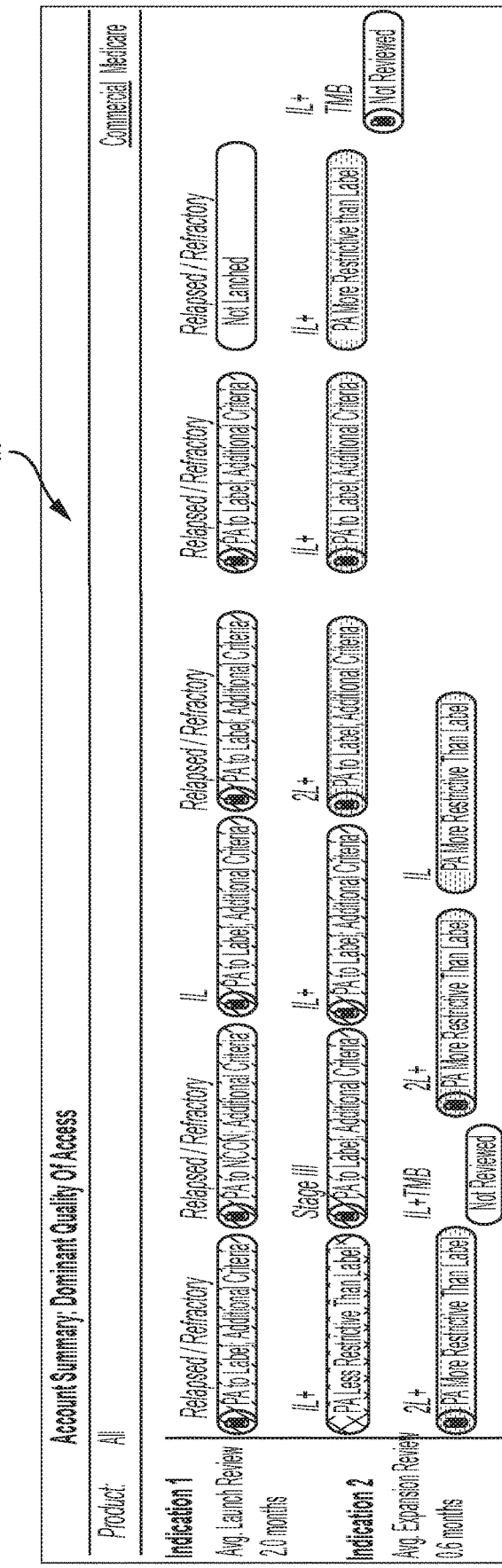
FIG. 19 is a graphical representation of a pop-up display of payer information from the table of FIG. 18, according to at least one aspect of the present disclosure.
FIG. 20 is a graphical representation depicting a portion of an account view overview for the payer of FIG. 19, according to at least one aspect of the present disclosure.

Referring now to FIG. 20, a portion of an account summary 370 for the Payer Account Dashboard 233 is shown. For the selected payer, the QoA Tool 230 filters the content such that the account summary 370 depicts dominant quality of access data for the various products and lines of therapy assigned to each indication. Additionally, for each product and line of therapy, the account summary 370 indicates a restrictiveness category (e.g. "PA to Label", "PA to NCCN", "PA More Restrictive than NCCN" and so on). The products and lines of therapy can be coded (e.g. color-coded) to quickly indicate whether the product/line of therapy is generally more restrictive or less restrictive than other payers. The account summary 370 also includes the time frame for the average launch/expansion review, as appropriate for the indication.

The Payer Account Dashboard 233 can include a summary sheet in terms of the account, the quality of access for multiple products, average review and launch times (see FIG. 21), contractual relationships with manufacturers, pharmacy affiliations and partners, the medical plan lives and pharmacy plan lives for different payer types (e.g. commercial, Medicare advantage, and managed Medicaid), a geographic distribution of total payer lives, which can be broken down by payer type, and the key influencers from a decision making perspective. The organization of this information can help decision-makers anticipate when a payer is conducting a review and, thus, when the decision-maker should engage the payer. Referring to a graphical representation 380 in FIG. 21, the Payer Account Dashboard 233 (FIG. 5) can also indicate whether the payer defaults to NCCN policy guidelines and the recognized level of recommendations. Exception requirements to obtain coverage are also provided in FIG. 21. Additionally or alternatively, the Payer Account Dashboard 233 can help the decision-maker determine how the payer views the competitors' product(s) and what is important to them in this therapeutic area and for this population (e.g. a particular indication).

The Payer Account Dashboard 233 can also indicate the management capabilities of the payer account including the management requirements that are considered to be more restrictive or less restrictive in comparison to other payers. The third party partnerships (e.g. pathways) can also be identified. Referring now to FIG. 22, a product coverage summary 390 for the Payer Account Dashboard 233 (FIG. 5) is provided in which the payer's quality of access is summarized including the dominant quality of access, the formulary tier, and the participating value-based models. For each participating model, the pharmacy lives exposure and inclusion of the product, as well as the alignment of payer policies with model guidelines for an included product can be provided. The data for the Payer Account Dashboard 233 can be extracted from multiple sources that include proactive surveillance of payer policies, provider bulletins, provider manuals from the payers, and so on. FIGS. 21 and 22 depict screenshots of the graphical representations 380, 390, respectively, which can conveyed to a user accessing the payer account dashboard 233 on a display, such as the display 116 (FIG. 5), for example.

Provider Accounts Tool

In various instances, providers may constitute restrictive mechanisms for a product. For example, a provider may not utilize a product due to lack of familiarity, training, and/or support by the payer and/or third party intermediaries, for example. In various instances, to determine links between providers and accessibility, providers can be classified into different segments and comparisons can be drawn between providers within a segment, between a provider and segment average, and/or between a provider and national average across all segments, for example.

The PKA Tool 232 is configured to provide transparency into provider-specific restrictions for particular products and/or indications and insight into the reach of such restrictions, as well as the underlying causes. The PKA Tool 232 can inform an understanding of key business models, internal protocols positioning, and engagement priorities, for example. In one aspect, the PKA tool 232 can be a strategic decision support tool for analyzing provider restrictions for at least one pharmaceutical product, and can comprise a remote database storing content related to a set of providers and sales data for the at least one pharmaceutical product, a remote server configured to access content stored in the remote database, and a local device coupled to the remote server by a network, wherein the local device comprises an input tool and a display. In various instances, in response to a filter selected with the input tool and communicated to the remote server across the network, the remote server is configured to determine a first score for each of the providers, determine a second score for each of the providers, plot the first score and the second score for each of the providers in a two-dimensional plot, wherein the two-dimensional plot comprises segmentation quadrants, wherein each segmentation quadrant corresponds to a segmentation category. In such instances, the remote service is further configured to identify the segmentation category of each provider from the plot, generate a graphical representation of the segmentation categories, and display the graphical representation via a graphical user interface on the display to facilitate analysis of provider restrictions to a first pharmaceutical product.

The first score can be indicative of clinical capabilities, as further described herein. The second score can be indicative of centralization of operations and decision-making, as further described herein.

To further facilitate the analysis of the at least one pharmaceutical product, the PKA Tool 232 can repeat the comparative analysis for multiple pharmaceutical products and/or multiple providers. Filtering of the products and/or providers can occur according to pharmaceutical product, indication, line of therapy, patient sub-type, type of payer, coverage, geographic territory, and various combinations thereof. Various features and functions of the PKA Tool 232 are further described herein.

In various instances, the PKA Tool 232 can segment providers into different segments. For example, providers can be segmented into one of the following segments: Clinical Champions, Restrictive Integrated Clinicians, Streamlined Operators, and Decentralized Physicians. Clinical Champions are defined as clinically-focused accounts that are motivated by clinical data, trial participation, and innovative approaches to medicine while placing little or no focus on economics. Restrictive Integrated Clinicians are defined as accounts with a high emphasis on value-based care and standardizing product utilization across sites when total cost of care reductions can be generated. Streamlined Operators are defined as accounts focused on standardizing operations and product use through pathways enforcement, while controlling cost using contracting and cost-cutting measures. Decentralized Physicians are defined as accounts that are eager to gain clinical recognition, but are hesitant to adopt newer therapies until proven to be a standard of care and when reimbursement risk is minimized. Segmentation of the providers is further described herein. The foregoing segment names are non-limiting and exemplary names based, in part, on the various metrics used to segment the providers. The reader will appreciate that alternative names can be employed.

Figure 23:
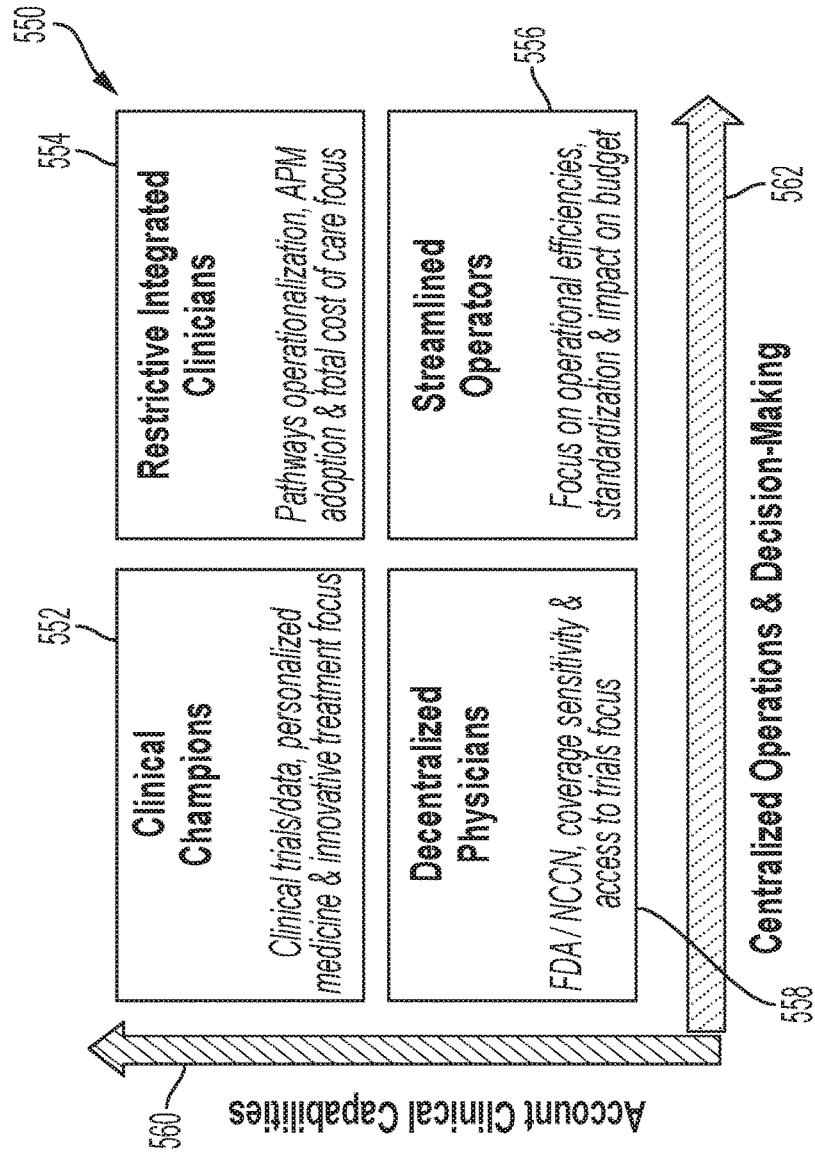
FIG. 23 is a graphical representation depicting provider account segmentation categories for the Provider Key Account Tool of FIG. 5, according to at least one aspect of the present disclosure.

Referring now to FIG. 23, metrics for determining segmentation of the providers are shown. For example, the metrics can define the axes of a four-quadrant matrix 550 and each quadrant can correspond to one of the segments. More specifically, a first quadrant 552 corresponding to the Clinical Champions segment is positioned in an upper left corner, a second quadrant 554 corresponding to the Restrictive Integrated Clinicians segment is positioned in an upper right corner, a third quadrant 556 corresponding to the Streamlined Operators segment is positioned in a lower right corner, and a fourth quadrant 558 corresponding to the Decentralized Physicians segment is positioned in the lower left corner. The vertical axis 560 corresponds to account clinical capabilities including payment model sophistication, standard of care development and adoption, and personized medicine investment. The horizontal axis corresponds to centralized operations and decision-making including pathways and protocol use and product preferences.

The first quadrant 552, designated Clinical Champions, can be characterized by clinical trials/data, personalized medicine, and innovative treatment options, for example. The second quadrant 554, designated Restrictive Integrated Clinicians, can be characterized by pathways operationalization, APM adoption, and total cost of care focus, for example. The third quadrant 556, designated Streamlined Operators, can be characterized by a focus on operational efficiencies, standardization, and impact on budget, for example. The fourth quadrant 558, designated Decentralized Physicians, can be characterized by FDA/NCCN guidelines, coverage sensitivity, and access to trials focus.

In various instances, the quadrant-defining datum or lines can be determined by distributing the providers proportionately such that a substantially even number of providers are allocated to each quadrant. For example, for 104 provider accounts in FIG. 24, the quadrants include between 33 and 21 providers, which is substantially evenly distributed around the average of 26 providers. In certain instances, the datum can be shifted to improve or substantially equalize distribution of the providers within the quadrants.

Figure 24:
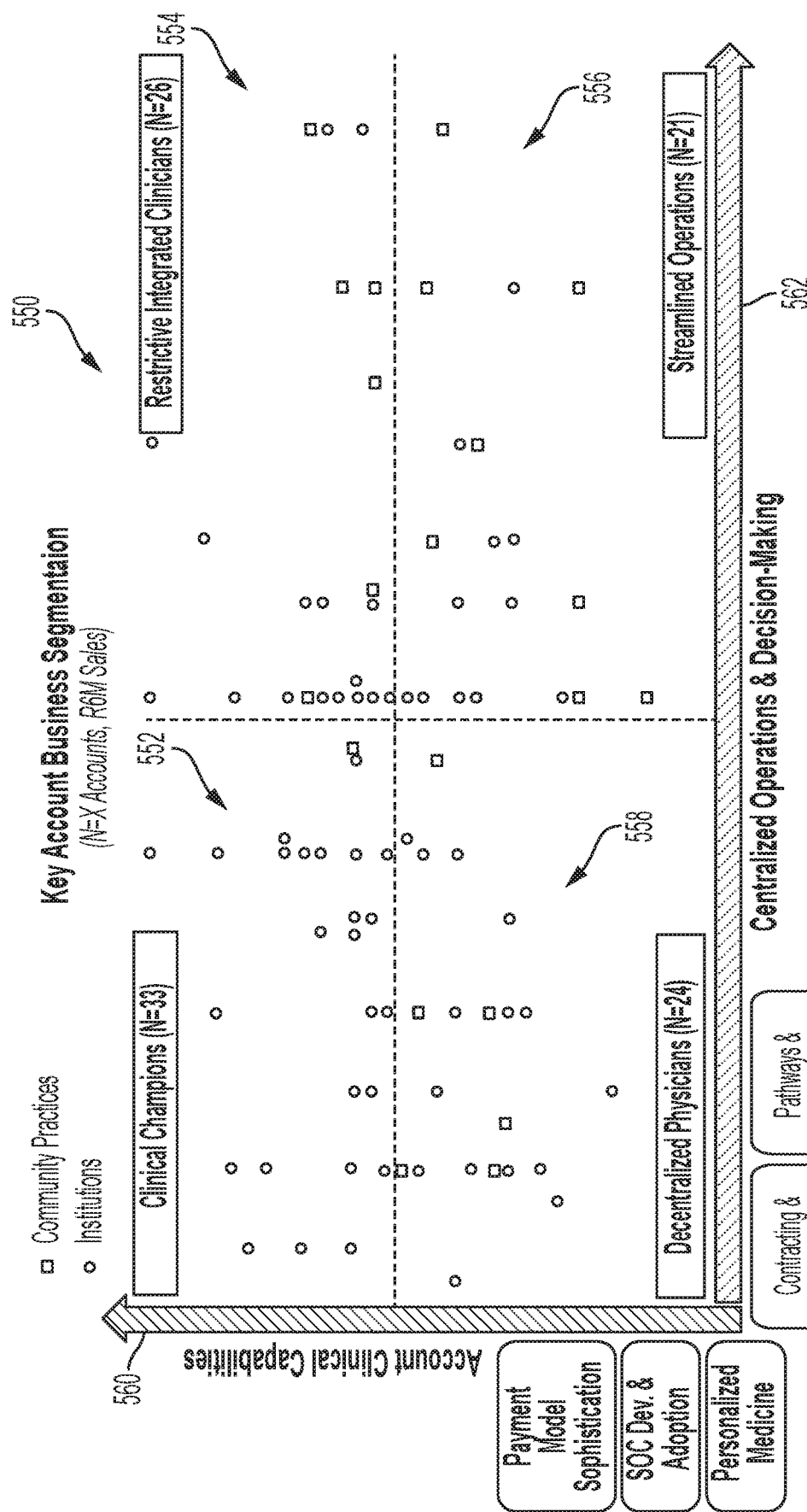
FIG. 24 is a graphical representation depicting key provider accounts segmented into the categories of FIG. 23, according to at least one aspect of the present disclosure.
Figure 24A:
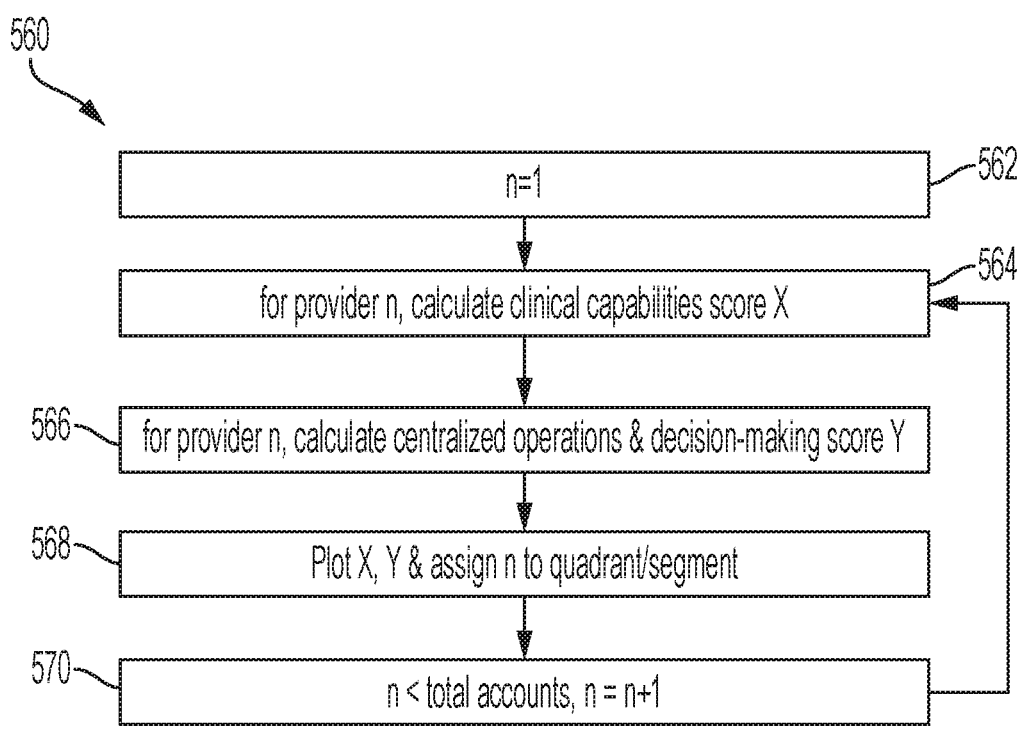
FIG. 24A is a logic diagram depicting steps to segment key provider accounts into the categories of FIG. 23 based on a clinical capability score and a centralized operations and decision-making score, according to at least one aspect of the present disclosure.

Referring now to FIG. 24, provider accounts can be plotted in the four-quadrant matrix 550 based upon the foregoing factors. Depending upon the location of the provider account in one of the four quadrants, 552, 554, 556, and 558, a segment can be assigned. An exemplary logic flowchart 560 for the segmentation of provider accounts is depicted in FIG. 24A. In various instances, the logic flowchart 560 can be utilized by the computing environment 100 (FIG. 1). At block 562, n=1.

At block 564, for the first provider, Provider 1, the clinical capabilities score x is calculated. The clinical capabilities score x is determined by weighing payment models sophistication, standards of care development and adoption, and personalized medicine investments. For example, a payment model sophistication value can be assigned from a scale based on participation in APM/pathways, a standards of care development and adoption value can be assigned from a scale based on membership, early adopter mentality, and clinical trial volume, and a personalized medicine investment value can be assigned from a scale based on biomarker testing capabilities and physician buy-in. The scales can depend on the number of categories, for example, and may be zero to one, zero to two, zero to five, and/or zero to ten, for example. The values along the scale can then be totaled (i.e. added together) for the resultant clinical capabilities score x. In certain instances, one or more of the values can be normalized prior to totaling the values.

At block 566, for Provider 1, the centralized operations and decision-making score y is calculated. The centralized operations/decision-making score y is determined by weighing pathway and protocol use and product preferences. For example, a pathway and protocol value can be assigned from a scale based on the existence and structure of external pathways/internal protocols, adherence levels, EMR-pathways integration, preferences/order set update communications, and incentive and/or penalty structures. A product preferences value can be assigned from a scale based on whether contracting partnerships lead to preferencing. The scales can depend on the number of categories, for example, and may be zero to one, zero to two, zero to five, and/or zero to ten, for example. The values along the scale can then be totaled (i.e. added together) for the resultant centralized operations/decision-making score y. In certain instances, one or more of the vales can be normalized prior to totaling the values.

The clinical capabilities score x and the centralized operations and decision-making score y for Provider 1 are plotted in two-dimensional space and assigned to a segment based on the position of the x and y coordinates relative to the quadrants at block 568. The segmentation of a subsequent provider, e.g., Provider 2, can begin at block 570 and the process can be repeated until the total key accounts (e.g. top 100 accounts for a product or treatment) are segmented.

Figure 25:
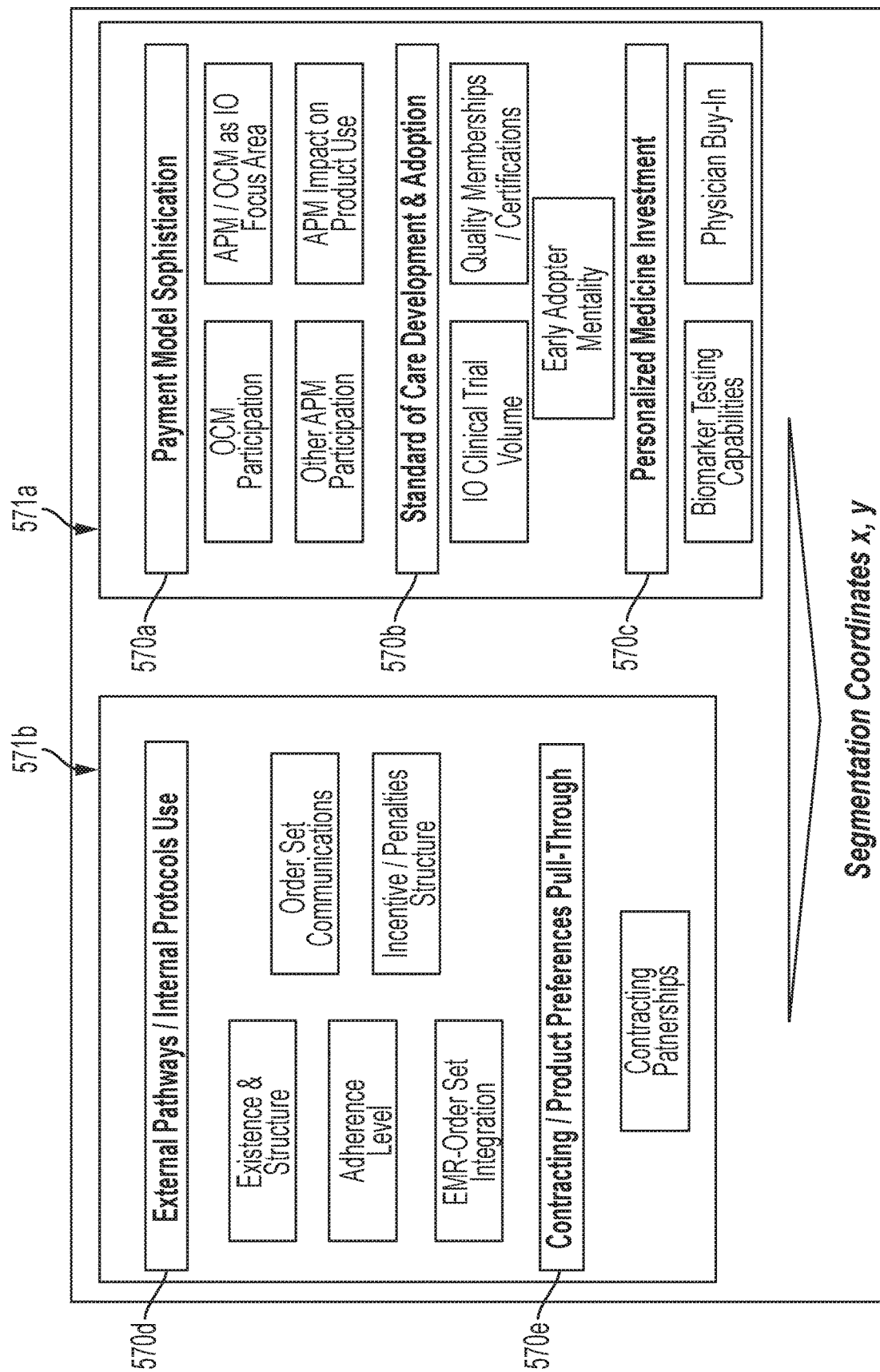
FIG. 25 is a flow chart depicting factors for calculating clinical capability scores and centralized operations and decision-making scores for the logic diagram of FIG. 24A, according to at least one aspect of the present disclosure.

The two-dimensional coordinates for each provider account with respect to clinical capabilities and centralized operations/decision-making can be determined by determining two independent scores—a clinical capabilities/progressiveness score 571a and a centralized operations/decision-making score 571b—based on the factors listed in a flowchart 570 shown in FIG. 25 for determining the segmentation coordinates, for example. First factors 570a, 570b, 570c effect the clinical capabilities/progressiveness score 571a. Second factors 570d, 570e effect the centralized operations/decision-making score 571b. The first factors 570a, 570b, 570c relate to payment model sophistication (e.g. OCM participation, APM/OCM as IO focus area, other APM participation, and APM impact on product use), standard of care development/adoption (e.g. IO clinical trial volume, quality memberships/certifications, and early adopter mentality), and personalized medicine investment (e.g. biomarker testing capabilities and physician buy-in), respectively. The second factors 570d, 570e relate to external pathways/internal protocols use (e.g. existence/structure, adherence level, order set communications, EMR-order set integration, and incentives/penalties structure) and contracting/product preferences pull-through (e.g. contracting partnerships), respectively.

In one instance, for immuno-oncology key accounts, with respect to a payment model sophistication value for the clinical capabilities score x, the following factors can be considered: account participation in Oncology Care Models (OCMs)/APMs, degree of institutional focus on OCMs/APMs, and product use changes due to APM participation. With respect to the standard of care development and adoption value for the clinical capabilities score x, the following factors can be considered: current memberships (NCCN, National Cancer Institute [NCI], etc.), adoption of Immuno-Oncology (IO) therapies in new settings, and participation in multiple IO clinical trials. With respect to personalized medicine investment value for the clinical capabilities score x, the following factors can be considered: degree of broad biomarker testing, biomarker testing operations, and level of physician buy-in for IO towards routine biomarker testing.

In one instance, for immune-oncology key accounts, with respect to pathways and protocol use value for the centralized operations and decision-making score y, the following factors can be considered: internal/external pathways use, pathways adherence rate, Electronic Medical Record (EMR) integration of pathways, and pathways incentives/penalties. With respect to product preferences value for the centralized operations and decision-making score y, the following factors can be considered: existence of preferencing and market share of preferred products.

In one implementation of the present disclosure, the providers can be plotted according to the following segmentation metrics. The horizontal, x-axis is a scale from 0-20, with an intersection point of 9.5, and the vertical y-axis is a scale from 0-18, with an intersection point of 10. Scoring can be as follows.

The clinical capabilities score x can be determined based on account clinical capabilities and organizational progressiveness for the y-axis and having a maximum score of 20 as follows:

---

Payment Model Sophistication: Max score: 7; Normalize to 7
OCM Participation: Whether or not accounts are participating in OCM, given the significant infrastructure requirements
No = 0
Yes = 2
Other APM Participation: Other APM participation and impact on total cost of care perceptions across anchor tumors
No = 0
1 APM = 1
≥2 APM/PPS-Exempt = 2
APM/OCM as IO Focus Area (based on survey responses)
None = 0
Low (1-2) = 0.5
Medium (3) = 1
High (4-5) = 2
APM Impact on Product Use: Whether or not APM participation is having an impact on product utilization across the organization (may obtain multiple points as a result of multiple certifications)
No = 0
Impact on combination therapy = 0.5
Impact on IO Utilization = 0.5
Standard of Care Development and Adoption: Max score: 7; Normalize to 7
NCI/NCCN Membership: NCI and NCCN member institutions create consensus on new standard of care based on available data (may obtain multiple points as a result of multiple certifications)
None = 0
NCI = 1
NCCN = 1
QOPI = 1
Early Adopter Mentality: Accounts that have rapidly adopted newer IO therapies represent progressive accounts. Certain analogs were also analyzed to support early adopter status.
Combined Imfinzi & Bavencio MS <18% (National Average) = 0
Combined Imfinzi & Bavencio MS ≥18% (National Average) = 1
IO Clinical Trial Volume: Accounts with greater IO clinical trial volume have a higher value perception of IO therapies and generally believe they will be standard of care across many tumors. Trials evaluated included historical and current trials.
No trials = 0
Low (1-3) = 1
Medium (4-6) = 2
High (≥7) = 3
Personalized Medicine Investment: Max score: 4; Normalize to 6
Biomarker Testing Capabilities: Accounts with PD-L1 or other NGS/

-continued genetic capabilities recognize and appreciate the role that
personalized medicine will play in the future, and have invested
in resources to support further utilization
Low (0-1) Internal Capabilities = 1
High (≥2) Internal Capabilities = 2
Physician Buy-In: Physician support for personalized medicine across the
organization demonstrates consensus around the value of IO therapies and
other future approaches
Low = 0
Medium = 1
High = 2

A screenshot of an exemplary scoring algorithm 574 for the clinical capabilities score x is also shown in FIG. 26.

The centralized operations and decision-making score y can be determined based on account centralized operations and restrictiveness for the x-axis and having a maximum score of 20 when the summed score is multiplied by two as follows:

External Pathways/Internal Protocols Use: Max score: 6, Normalize to 8
Existence and Structure: Whether or not accounts have formally-developed
pathways beyond aligning to national guidelines (e.g. NCCN)
None = 0
In development = 0.5
Pathways = 1
Adherence Level: Compliance rate explains the degree of freedom that
providers have to deviate from pathways; if the adherence rate is too low
the autonomy will remain with the physicians
Actual Adherence <80% = 0
Actual Adherence ≥80% = 1
EMR-Pathways Integration: Pathways/protocols that are integrated within
the EMR are easier enforce given their connection with order sets,
whereas it is challenging to monitor adherence for pathways housed in an
external portal
Not Linked = 0
Pathways Linked to EMR = 1
Preferences/Order Set Update Communications:
Weak (single modality) = 0
Strong (multiple modalities) = 1
Incentive and/or Penalty Structure: Accounts that are enforcing pathways
adherence through financial means demonstrate a higher level of top-down
control
No Incentives or Penalties = 0
Incentives and/or Penalties in Development = 1
Incentives Only = 2
Penalties Only = 2
Contracting/Product Preferences Pull-Thru: Max score: 1, Normalize to 2
Contracting Partnerships Lead to Preferencing: Communication of
contracting preferences to physicians (formally and informally) & market
share shifts due to contracting
No = 0
≥10% Increased MS Preference = 1

A screenshot of an exemplary scoring algorithm 576 for the centralized operations and decision-making score y is also shown in FIG. 27.

Figure 28:
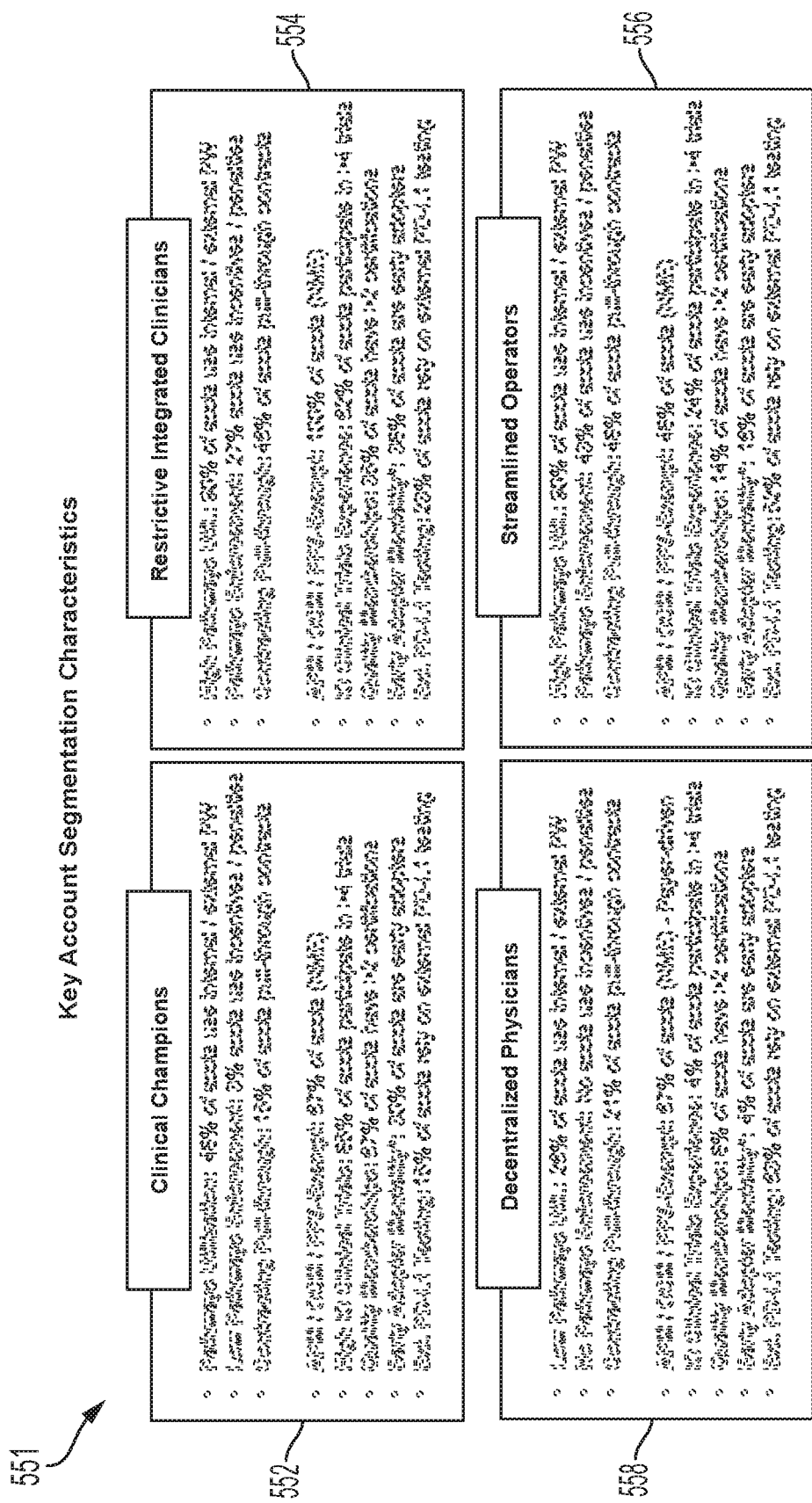
FIG. 28 is a graphical representation of a screenshot including a table of key account segmentation characteristics for the categories of FIG. 23, according to at least one aspect of the present disclosure.

By evaluating centralized account operations and restrictiveness, as well as clinical capabilities and progressiveness, the unique behaviors of the providers in each quadrant 552, 554, 556, 558 demonstrate various characteristics of the corresponding account segment. Exemplary characteristics for a set of providers selected by the user and filtered by a filtering scheme are shown in a screenshot 551 in FIG. 28 that can be provided to the user via the display 116 (FIG. 1). The screenshot 551 can highlight the pathway utilization, pathway enforcement, contracting pull-through-AMP/OCM/PPS-Exempt status, IO clinical trial experience, quality memberships, early adopter mentality, and external PD-L1 testing for each quadrant 552, 554, 556, 558. By determining the averages in each quadrant 552, 554, 556, 558, the account segments can be compared to each other and to an average that includes all key providers across all segments. Additionally or alternatively, a select key provider can be compared to the average metrics of the selected key provider's segment to identify outlying characteristics, for example.

Figure 29:
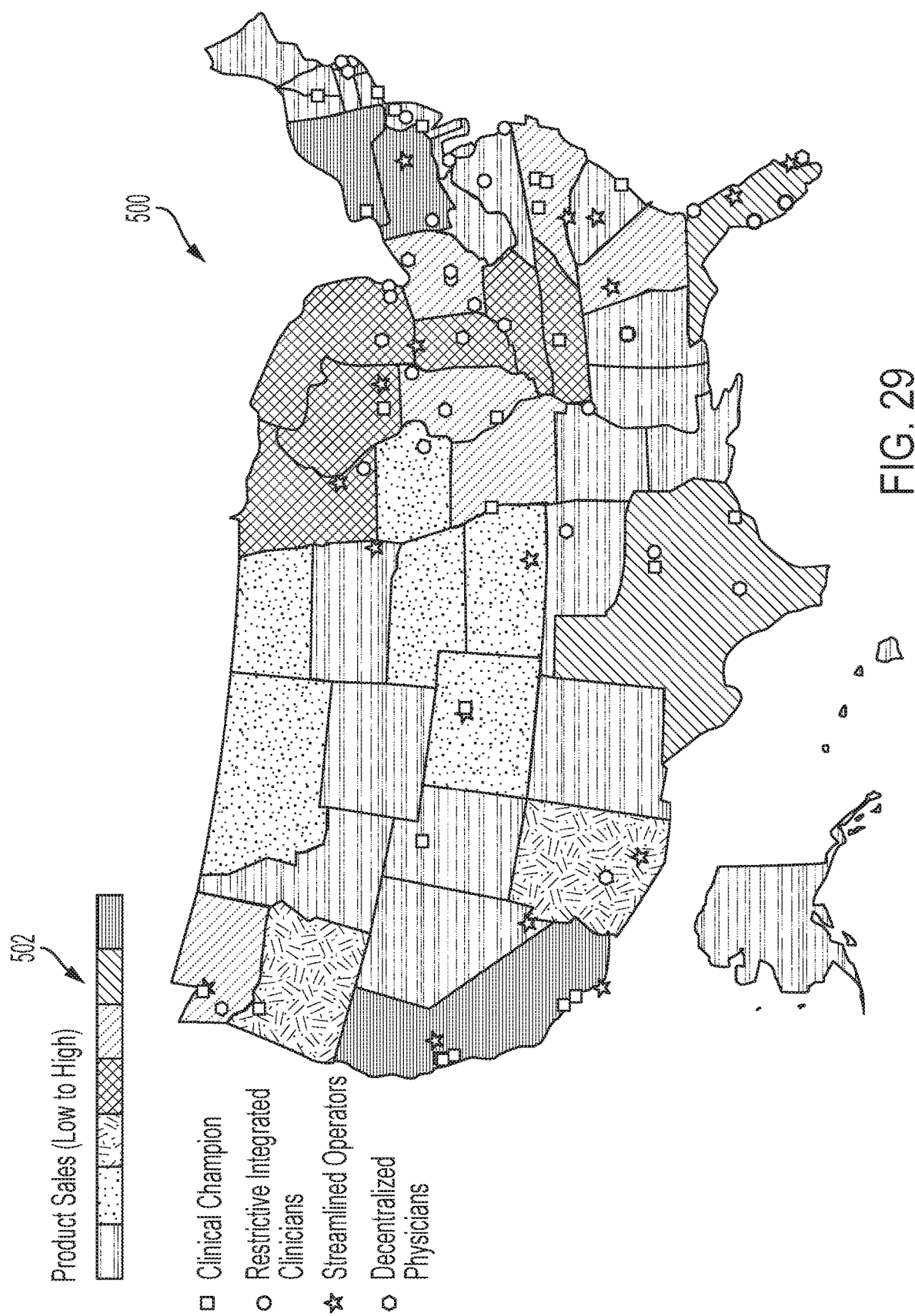
FIG. 29 is a graphical representation of a map showing sales data and primary account locations for the key provider accounts of FIG. 24, according to at least one aspect of the present disclosure.

In one instance, the geographic locations of all key providers can be overlaid on a map indicating the market share (e.g. sales) of a product or treatment across all the providers. Moreover, the providers in each segment can be overlaid on the map indicating the market share (e.g. sales) of the product or treatment across the providers in the segment. In this way, a decision-maker can determine if the location of a provider corresponds to its market share in the adjacent region, for example. Referring to FIG. 29, the top providers for a product are overlaid on a map 500. Regions of the map 500 are coded (e.g. color-coded or shaded) to correspond to different market shares according to a product sales spectrum 502. Furthermore, the segment for each provider is indicated in order to show the relative position of providers of different segments relative to their overall market share of the product.

Figure 30:
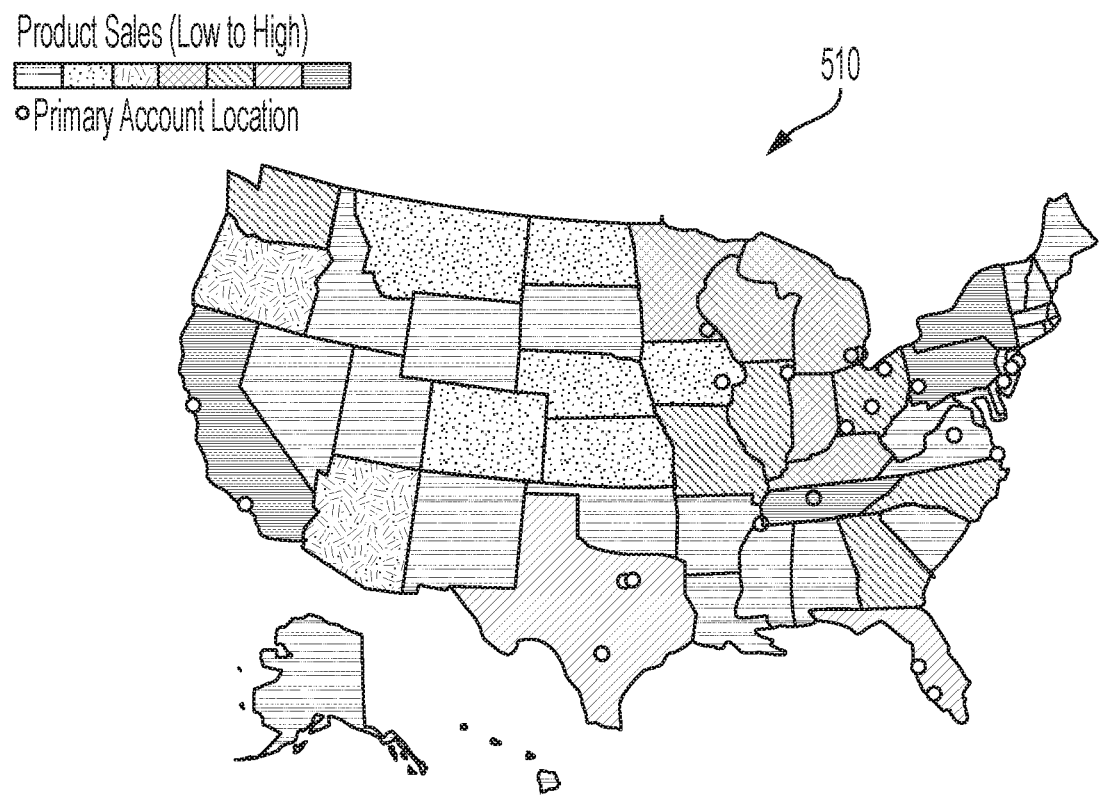
FIG. 30 is a graphical representation depicting a map showing sales data and primary account locations for the key provider accounts of FIG. 29 for one segmentation category—Restrictive Integrated Clinicians—according to at least one aspect of the present disclosure.

Referring now to FIG. 30, the analysis can be filtered to depict market share and providers geographically within each segment. For example, the segment designated "Restrictive Integrated Physicians" can be selected and the content can be filtered such that only the providers within the designated segment are depicted on the map 510. Such an analysis can depict states having higher or lower sales and the relative position of the different key accounts to facilitate an understanding of the regional dynamics of a product.

In various instances, the segments can be color-coded. For example, a first segment can be blue, a second segment can be green, a third segment can be yellow, and a fourth segment can be red. Upon selection of a segment corresponding to a particular color, the content can be filtered such that the display of the map can change to depict only the providers within the selected segment using the particular color and the market share (e.g. sales) can be portrayed with different degrees of shading in the same color. For example, when a "green" segment is selected, the provider locations can be indicated with green markers or icons and the regions can be shaded from white or light green to dark green depending on the amount of sales in the region.

Figure 31:
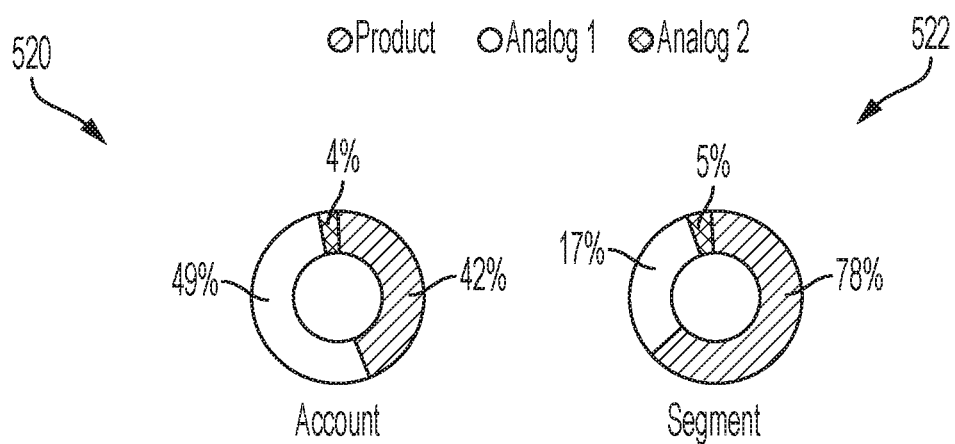
FIG. 31 is a graphical representation of sales data for a product and analog products for, one, a key provider account in the Restrictive Integrated Clinicians segment of FIG. 30 and, two, all key provider accounts in the Restrictive Integrated Clinicians segment, according to at least one aspect of the present disclosure.

In various instances, a provider account can be selected from the maps 500, 510 and/or from a listing of provider accounts adjacent to the maps 500, 510. Referring to a graph 520 in FIG. 31, for a selected provider account in the Restrictive Integrated Clinicians segment of FIG. 30, sales data for a product and the analogs are shown. Moreover, referring to a graph 522, the sales data for all provider accounts in the segment, i.e. a subset of the providers, is shown. Upon comparing the two graphs 520 and 522, a decision-maker can ascertain how a given account compares to the segment a whole. For example, in the graphs 520 and 522, the selected provider account is under index compared to other accounts in the same segment. In various instances, the sales data for the selected provider account can also be compared to the national market across all segments, for example.

Figure 32:
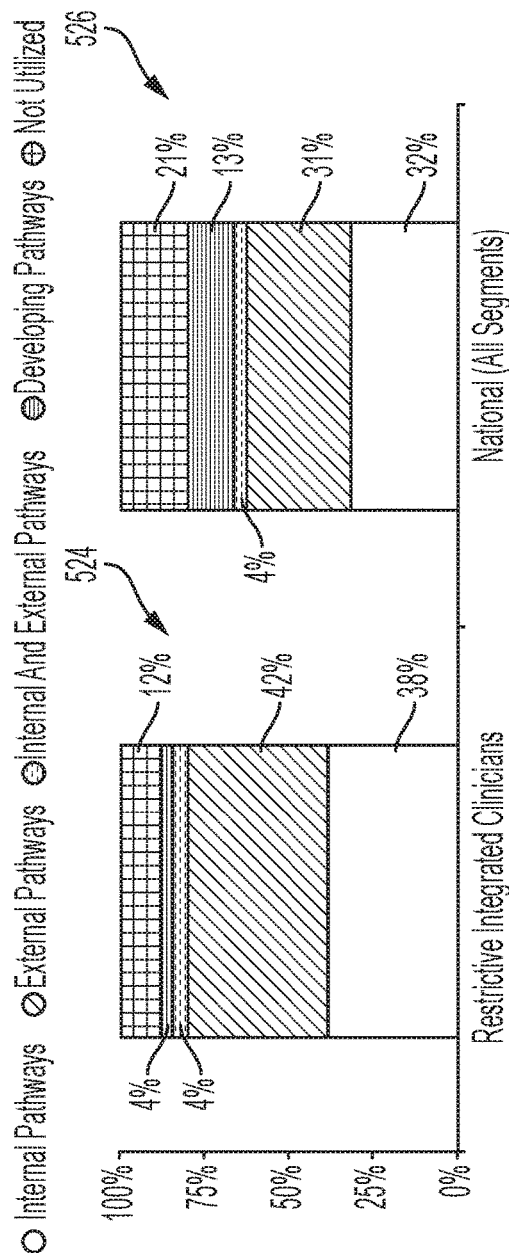
FIG. 32 is a graphical representation depicting pathway utilization for, one, a particular segment and, two, nationally across all segments, for the key provider accounts of FIG. 24, according to at least one aspect of the present disclosure.

The PKA Tool 232 (FIG. 5) can also compare the site of care mix (e.g. academic centers, community practices, hospital systems, and integrated delivery network [IDN]), total sales, and percent grown between and/or across segments. In certain instances, the PKA Tool 232 can also provide a listing of Key Decision Makers and Key Influencers (e.g. lead oncologist, mid-level oncologist, pharmacy director, quality director, CEO/Practice Manager, billing department, nursing director, and so on) within each segment. With respect to value-based care, the PKA Tool 232 can depict pathway utilization for a particular segment and nationally across all segments, as shown in FIG. 32. For example, referring to a graph 524, with the segment Restrictive Integrated Physicians, 38% of accounts have formally adopted internal pathways, 42% of accounts have formally adopted external pathways, 4% of accounts of formally adopted both internal and external pathways, 4% are in the process of developing pathways, and 12% do not utilize pathways. Comparatively, referring to a graph 526, across all segments nationally, 32% of accounts have formally adopted internal pathways, 31% of accounts have formally adopted external pathways, 4% of accounts of formally adopted both internal and external pathways, 13% are in the process of developing pathways, and 21% do not utilize pathways.

Figure 33:
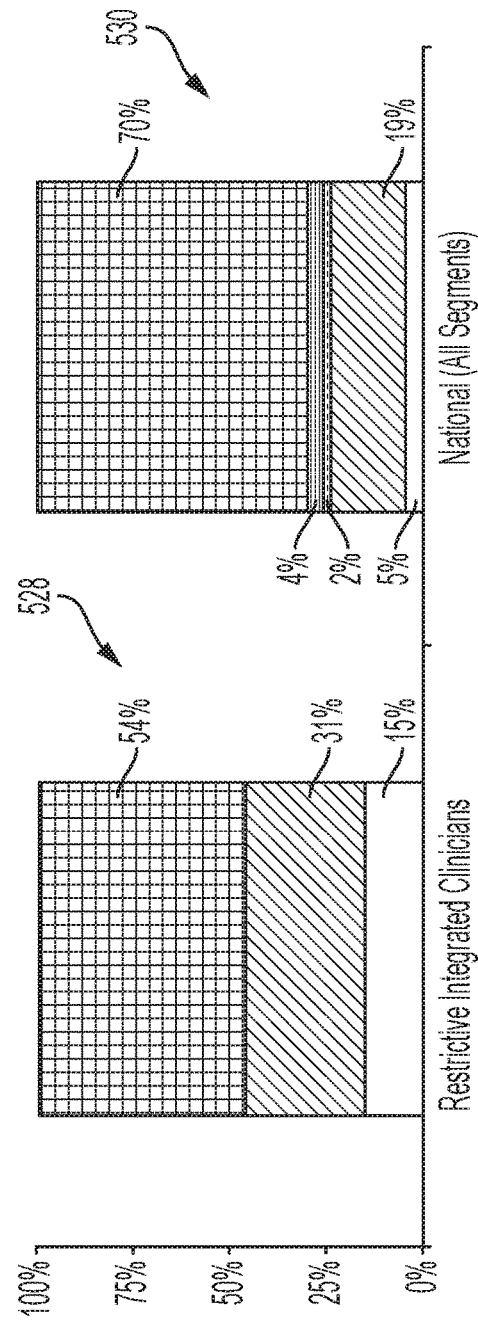
FIG. 33 is a graphical representation depicting pathway enforcement mechanisms for, one, a particular segment and, two, nationally across all segments for the key provider accounts of FIG. 24, according to at least one aspect of the present disclosure.

The PKA Tool 232 can also depict pathway enforcement mechanisms for a particular segment and nationally across all segments, as shown in FIG. 33. For example, referring to a graph 528, with the segment Restrictive Integrated Clinicians, 15% of accounts utilize incentives to enforce provider adherence to pathway therapy preferences, 31% of accounts utilize penalties to enforce provider adherence to pathway therapy preferences, and 54% do not enforce adherence. Comparatively, referring to a graph 530, across all segments nationally, 5% of accounts utilize incentives to enforce provider adherence to pathway therapy preferences, 19% of accounts utilize penalties to enforce provider adherence to pathway therapy preferences, 2% utilize incentives and penalties to enforce provider adherence to pathway therapy preferences, 4% are in the process of adopting incentives and/or penalties, and 70% do not enforce adherence. The Restrictive Integrated Clinicians segment, in this particular instance, utilizes and enforces pathways more aggressively than the average of all key accounts nationally. The foregoing analyses can facilitate decision-making with respect to the targeting of resources around pathways, sub-types thereof, and/or implementation strategies to address restrictions to a product within a specific segment.

In various instances, the PKA Tool 232 can also include a Provider Account Dashboard that provides account information for specific accounts covered by the tool 232. For example, whereas various analyses described herein generally provide a top-down management perspective of provider accounts across the various segments, for example, the Provider Account Dashboard can provide a focused profile for each provider account.

To access a provider account profile from the nationwide and/or segment-specific database, a user can select a particular account for detailed information and analyses regarding the selected account. Alternatively, a user can search for a particular account via a search bar/lookup tool, for example. Each account in the database can include a physician autonomy score, immunotherapy strength score, and/or listing of key decision-makers and influencers thereof, for example.

Figure 34:
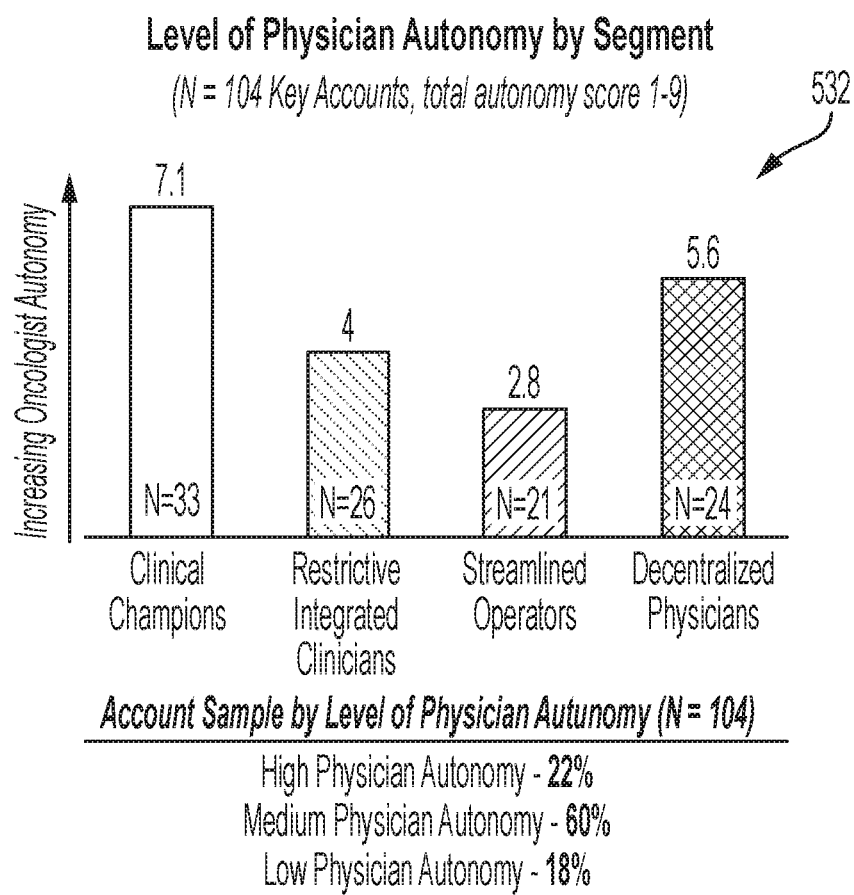
FIG. 34 is a graphical representation depicting a graph depicting level of physician autonomy by segment, according to at least one aspect of the present disclosure.

The physician autonomy score relates to the level of physician decision-making freedom, based on pathways, access challenges (e.g. the communication of payer coverage restrictions, patient out of pocket burden/cost, and level of payer reimbursement to physicians) and account pressures (e.g. the degree to which pharmacy is involved in formulary decisions), for example. For example, the existence of pathways and/or protocols to standardize care and incentives and/or penalties for pathway compliance can lower a physician autonomy score. However, an off-pathways exception process can limit the effect. A high physician autonomy score denotes increased autonomy due to decreased pathways enforcement mechanisms, lower sensitivity to therapy access challenges, and a lower degree of organizational pressure on physician decisions, for example. The physician autonomy score can be compared to the national average across all segments and/or a segment-specific average, for example. A graph 532 depicting average physician autonomy scores by segment is depicted in FIG. 34. For example, Clinical Champion can demonstrate the highest score, followed by Decentralized Physicians, then Restrictive Integrated Physicians, and, finally, Streamlined Operators.

The immunotherapy strength score relates to the degree to which each account is focused on innovative immunotherapy treatments and/or partnerships (e.g. Chimeric Antigen Receptor T-cell (CAR-T) Therapy, IOs, and so on). The immunotherapy strength score can also be compared to the national average across all segments and/or a segment-specific average, for example.

With respect key decision-makers and influencers for each key provider account, the PKA Tool 232 can provide a listing of individuals, departments, groups, and/or boards and sort the decision-makers/influencers into influence categories ranging from highly influential to moderately influential to minimally influential, for example. In various instances, the decision-makers and influencers can be ranked and/or assigned a score, such as along a scale from zero to five, for example.

The PKA Tool 232 can also include a summary of partnerships (e.g. active partnerships between the account and other institutions or pharmaceutical companies) and operational infrastructure information, such as internal operations (340B designation, EMR type, external data vendor, distributor, and Group Purchasing Organizations [GPOs], for example), accreditations (NCCN member, NCI designation, Quality Oncology Practice Initiative [QOPI], and MAGNET, for example), and Center of Excellence recognition for particular tumor types.

Additionally, the clinical sophistication of an account can be analyzed with the PKA Tool 232 by determining the provider's clinical progressiveness based on clinical trial volume and willingness to adopt new therapies, the biomarker testing capabilities or degree to which the account is capable of implementing precision medicine infrastructure, focus areas, clinical drivers, and a personalized medicine initiatives or degree to which the account is pursuing novel precision medicine partnerships and opportunities. In various instances, the personalized medicine initiative can refer to a strength score based on PD-L1 capabilities and other partnerships and/or collaborations, for example. The personalized medicine strength score can be compared to a national average across all segments and/or a segment-specific average for example.

The protocols of an account can be analyzed with the PKA Tool 232 by determining internal/third party pathways and whether such pathways go beyond national guidelines and directly impact prescribing patterns and account preferences. With respect to the pathways, the PKA Tool 232 can provide the exceptions process required for a physician to prescribe an off-pathways therapy and the use of adherence incentives and/or penalties to enforce provider adherence to pathway therapy preferences.

The PKA Tool 232 and account information therein can also provide payer mix, or the breakdown of insurance utilization by book of business across the accounts total patient population (e.g. commercial insurance, Medicare, Medicaid, and uninsured), APM participation information which is indicative of accounts that are more organizationally progressive and conscious of patient outcome, cost evaluation focus highlighting economic factors considered for therapy incorporation, and contracting overviews reporting whether the account is currently participating in any contracts (e.g. GPOs). Furthermore, account information in the PKA Tool 232 can list internal committees of influence (e.g. teams that participate in the decision making process) and their relative influence (high, moderate, or low), and the key influencers (e.g. stakeholders who provide input for decision making) and their relative influence (high, moderate, or low).

The PKA Tool 232 and account information therein can inform the decision-maker regarding where to focus and what is going to work strategically to influence and impact their value perception of the product. For example, for a given provider, if the physician autonomy score is low and access is controlled centrally by policy in which incentives and disincentives are in place to financial motivate the providers, a first tactical approach may be required to enhance access to a product. A similar approach can be implemented across the provider accounts within the same segment. For example, if a first approach yields favorable results for an account within a given segment, the approach can be disseminated throughout the segment for increased breadth and growth. Conversely, another approach can be utilized in a different segment.

Third Party Program Tool

In various instances, the TPP Tool 234 (FIG. 5) can improve transparency to third party intermediaries, or third party stakeholders, acting between the payers and the providers. The TPP Tool 234 can inform an understanding of trends and influences for pathways, alternative payment models, and oncology benefit managers, for example.

Though third party intermediaries often design programs (e.g. pathways and APM programs) to treat certain populations more efficiently and, thus, to save costs; such programs can simultaneously limit access to other out-of-program or off-pathway products for certain patients. In order to expand utilization of restricted products, the TPP Tool 234 can identify restrictive programs with respect to particular products for a population and/or can identify restrictiveness sources and/or trends towards restrictiveness or non-restrictiveness with respect to particular products for a population. For example, if an access restriction originates at a pathway organization, the TPP Tool 234 can identify the pathway organization and restriction therefrom, as well as the extent/type of the restriction(s) with respect to implementation, enforcement, and/or misalignment with FDA labeling and/or payer policy criteria, for example. Furthermore, the TPP Tool 234 can display the restrictiveness analysis in an interactive and intuitive format via a graphical user interface, which can further facilitate a decision-makers analysis. In other instances, an alternative regulatory authority can be utilized rather than the FDA label, for example.

In one instance, the TPP Tool 234 can be a strategic decision support tool for analyzing third party-based restrictions for at least one pharmaceutical product and can comprise a remote database storing content related to third party policies and comparative metrics for the at least one pharmaceutical product, a remote server configured to access content stored in the remote database, and a local device coupled to the remote server by a network, wherein the local device comprises an input tool and a display. In certain aspects of the TPP Tool 234, in response to a filter selected with the input tool and communicated to the remote server across the network, the remote server is configured to, extract policy criteria for a first pharmaceutical product from a third party policy based on the filter selected with the input tool, extract comparative metrics for the first pharmaceutical product based on the filter selected with the input tool, compare the extracted policy criteria to the extracted comparative metrics, assign, based on the comparison, a restrictiveness score, generate a graphical representation of the restrictiveness score, and display the graphical representation via a graphical user interface on the display to facilitate analysis of third-party based restrictions to the first pharmaceutical product for the third party policy.

To further facilitate the analysis of the at least one pharmaceutical product, the TPP Tool 234 can repeat the comparative analysis for multiple pharmaceutical products and multiple third party policies. Filtering of the products and/or policies can occur according to pharmaceutical product, indication, line of therapy, patient sub-type, type of payer, coverage, geographic territory, and various combinations thereof. Various features and functions of the TPP Tool 234 are further described herein.

In order to analyze the relevant pathways and APMs, the TPP Tool 234 can track each program with respect to the indication (e.g. diagnosis or tumor type) and the line of therapy (e.g. maintenance, first-line, second-line, third-line, and so on). Programs can vary between lines of therapy for different indications. For example, with respect to non-small cell lung cancer (NSCLC), which is an indication, the lines of therapy can include Maintenance, first-line (1L), second-line (2L), third-line (3L), and Stage III consolidation therapy, for example. A program can be directed at one or more lines of therapy for an indication and can recommend one or more products for each covered line of therapy. Additionally, the FDA labels for each product can be approved for one of more lines of therapy. With respect to certain products, the FDA labels can be aligned with the program recommendations; however, with respect to other products, the program recommendations can be more stringent than the FDA labels, for example.

Figure 35:
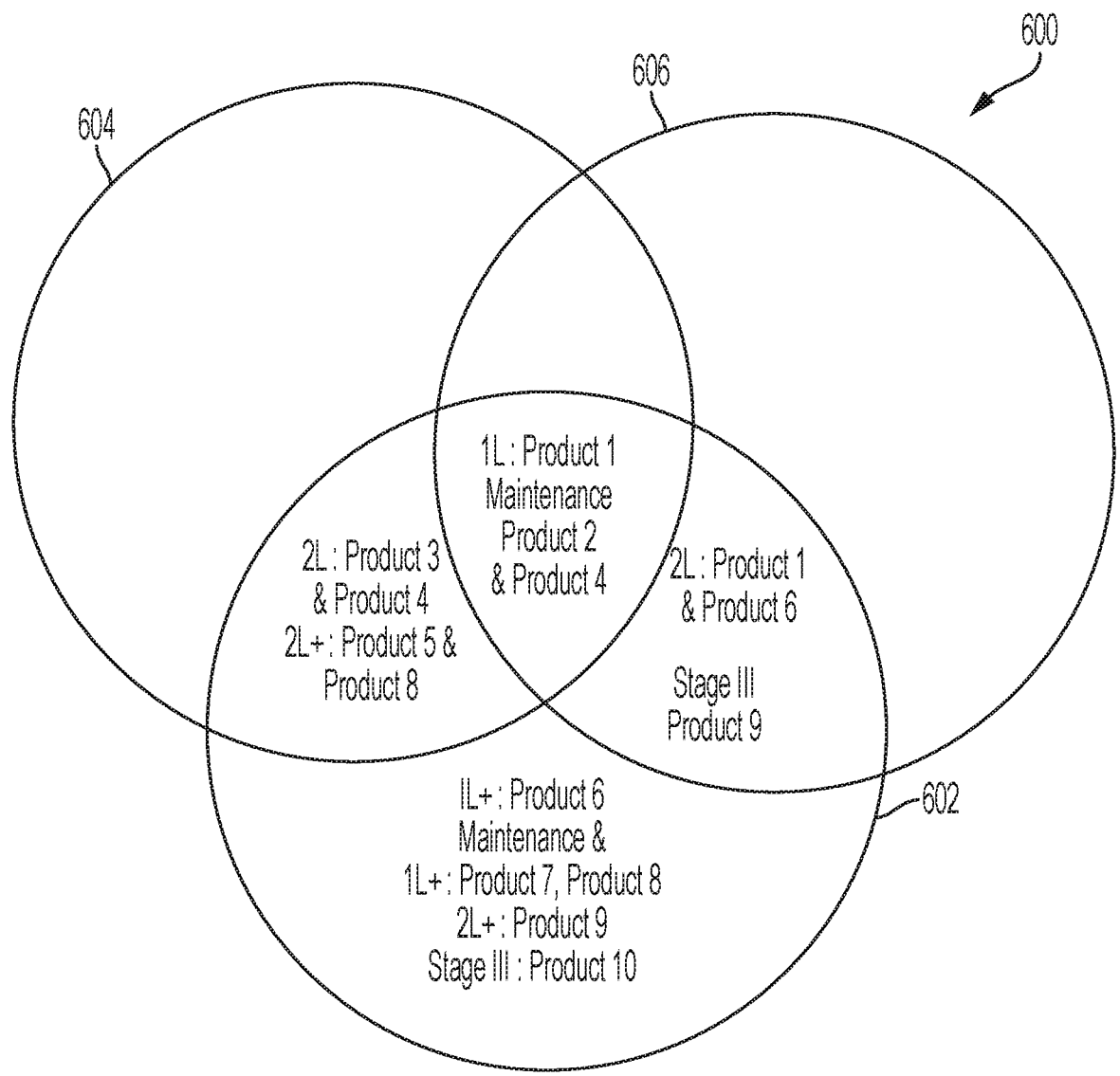
FIG. 35 is a Venn diagram depicting overlapping lines of therapy for an FDA label and different third party programs (e.g. pathway programs), according to at least one aspect of the present disclosure.

Referring now to FIG. 35, a Venn diagram 600 is depicted. The Venn diagram 600 includes the FDA label 602 and two exemplary programs (e.g. pathways)—a first program 604 and a second program 606. The Venn diagram 600 also depicts various products—Product 1, Product 2, Product 3, Product 4, Product 5, Product 6, Product 7, Product 8, Product 9, and Product 10—positioned throughout the Venn diagram 600 based on the alignment and/or misalignment among approved uses on the FDA label 602 (e.g. a comparative metric), suggested uses by the first program 604, and suggested uses by the second program 606. The FDA label 602 for each product lists one or more lines of therapy, which are summarized in the table below:

| Product Name | FDA Label: Line of Therapy |
|---|---|
| Product 1 | 1L & 2L |
| Product 2 | Maintenance |
| Product 3 | 2L |
| Product 4 | Maintenance & 2L |
| Product 5 | 2L+ |
| Product 6 | 1L+ |
| Product 7 | Maintenance & 1L+ |
| Product 8 | Maintenance & 1L+ |
| Product 9 | 2L+ & Stage III |
| Product 10 | Stage III |

-continued

| Product Name | FDA Label: Line of Therapy |
| --- | --- |

In certain instances, the FDA label 602 line of therapy for a product can correspond to the suggestions of the first program 604 and/or the second program 606. For example, Product 2 is approved by the FDA label 602 for maintenance therapy, which corresponds to the program suggestions for the first program 604 and the second program 606. In other instances, the first program 604 and/or the second program 606 can be more restrictive for one or more products. For example, Product 1 is approved by the FDA for first- and second-lines of therapy. However, referring again to the Venn diagram 600, the first program 604 only suggests Product 1 for a first-line therapy and the second program 606 only suggest Product 1 for a second-line therapy. In effect, Product 1 is restricted for both programs 604, 606. More specifically, Product 1 is restricted with respect to second-line therapy use with the first program 604 and is restricted with respect to first-line therapy use with the second program 606.

With respect to Product 3, the FDA label 602 approves use for second-line therapy; however, the second program 606 does not suggest Product 3 for any lines of therapy. The suggestions of the first program 604 with respect to Product 3 are aligned with the FDA label 602. In other words, with respect to Product 3, the second program 606 is more restrictive than the FDA label and comparatively more restrictive than the first program 604. In this example, Product 3 is at parity with the FDA label in the first program 604 and disadvantaged by the second program 606. With respect to other products, the first program 604 can be more restrictive than the second program 606. For example, with respect to Product 9, which is approved by the FDA label 602 for use with second-line therapy and Stage III consolidation therapy, the first program 604 does not suggest Product 9 for any lines of therapy. However, the second program 606 suggests Product 9 for Stage III consolidation therapy. In such instances, the first program 604 and the second program 606 are restrictive of Product 9; however, the first program 604 is more restrictive than the second program 606. In sum, a product may be suggested by one of the programs 604, 606 for fewer lines of therapy than approved uses by the FDA and/or may not be included in the program 604, 606 though it is approved for one or more lines of therapy by the FDA. Additional relationships are depicted in the Venn diagram 600. In still other instances, a program's suggested use of a product can extend beyond the FDA label's indications and/or lines of therapy. For example, a program can suggest an off-label use of a product, which can support an advantaged relationship for the product by that program.

Figure 36:
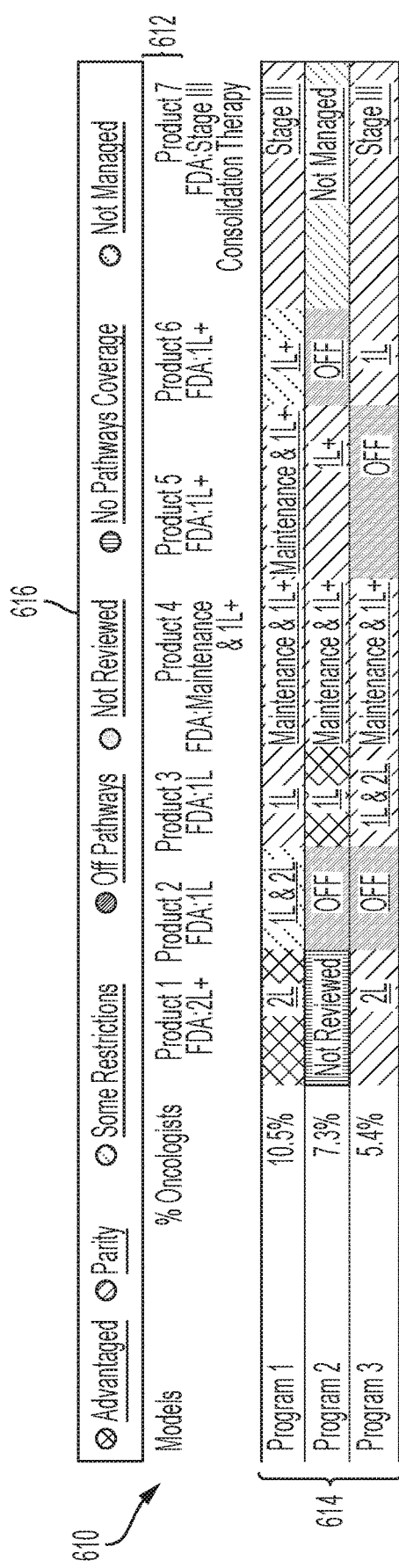
FIG. 36 is a graphical representation depicting brand positioning for various products relative to FDA label uses/lines of therapy for a selected indication across pathway programs for the Pathways & APM Tool of FIG. 5, according to at least one aspect of the present disclosure.

Beyond classifying relationships between a product's FDA label and suggested uses as part of a program, the TPP Tool 234 (FIG. 5) can be configured to reflect a brand or product's relative positioning with respect to other products/brands across programs, e.g. for multiple pathways. Referring now to FIG. 36, a table 610 is shown depicting relative access to multiple products 612 (e.g. seven products are depicted in FIG. 36) across multiple programs 614 (e.g. three programs are depicted in FIG. 36). In other words, the table 610 defines an m-by-n two-dimensional matrix in which m=7 and n=3 because seven products and three programs are included; however, the reader will readily appreciate the fewer and more products and/or programs can be displayed in the table 610. Each cell in the table lists the line(s) of therapy suggested for a product by the program. For example, Program 1 suggests Product 1 for second-line (2L) therapy.

Though the table 610 defines a two-dimensional m-by-n array, additional information can be embedded in the table 610 and readily apparent and analyzable by a decision-maker. For example, colors/shading within cells in the table 610 can be used to layer additional information regarding relative access of each product for each suggested line of therapy to the FDA label. Relative access can be classified as set forth in a key 616.

As provided in the key 616, product positioning relationships can be categorized as "advantaged", "parity", "some restrictions", "off pathways", "not reviewed", "no pathways coverage" or "not managed", for example. In various instances, (1) a first color or type of shading (e.g. green) represents an advantaged relationship in which a product/regimen is recommended on the pathway and is more advantaged than the product/regimen's FDA label, which is considered the preferred option in relationship to competing therapies; (2) a second color or type of shading (e.g. blue) represents a parity relationship in which a product/regimen is recommended on the pathway according to its FDA label; (3) a third color or type of shading (e.g. yellow) represents a relatively disadvantaged relationship in which a product/regimen is recommended on the pathway as more restrictive that the approved indication(s); (4) a fourth color or type of shading (e.g. red) represents an off-pathway relationship in which a product/regimen is not listed as an option on the pathway and its selection would be considered going "off-pathway"; and (5) a fifth color or type of shading (e.g. grey) represents that the relationship between the pathway and the FDA label has not been reviewed by the pathways committee, the pathway does not cover the tumor type/indication, and/or the pathway does not cover the line of therapy/setting. Definitions for each category in the key 616 can be displayed by hovering the cursor over the category in the key 616.

As an example, Product 1 in the table 610 is approved by the FDA label for 2L+ lines of therapy. However, Product 1 is only suggested by Program 1 and Program 3 for use as a second-line therapy. Moreover, Product 1 is not added as an option for Program 2 because it has not yet been reviewed by the pathways committee. Though Program 1 and Program 3 suggest Product 1 for use as a second-line therapy only, Product 1 is advantaged with respect to other products suggested by Program 1 and Product 1 is at parity with respect to other products suggested by Program 3. The advantaged/parity/disadvantaged classification is conveyed by the shading in the table. Moreover, the criteria for determining the advantaged, parity, or some restrictions categorization can be displayed by hovering the cursor over the coded indication within each cell. In one instances, a program can specify that a product is preferred and/or preferred given certain conditions, such as age, health, existing conditions, and/or contemporaneous treatments of the patient, for example. Such relative positioning of the products across programs is reflected in the table 610. In such instances, the two-dimensional array of information regarding overlapping lines of therapy for the FDA label and a program is overlaid or embedded with additional relative restrictiveness quantifications and information for the product.

Furthermore, additional information can be displayed by hovering a cursor over the icon/information within each color-coded cell (i.e. over the line(s) of therapy noted in each cell). For example, particular program criteria, such as preferences and/or restrictions, for example, can be displayed. In other instances, clicking or otherwise selecting the line(s) of therapy in a cell can open a pop-up and/or new window with additional information regarding the comparative preferences and/or restrictions.

The TPP Tool 234 is also configured to summarize the total restrictiveness across programs for a selected product relative to the FDA approved line(s) of therapy for the relevant indication. Referring to FIG. 37, a chart 620 depicts the number of programs in each category for a selected product. A key 622 summarizes the relevant categories. In various instances, definitions for each category in the key 622 can displayed by hovering the cursor over the category in the key 622. Upon comparing Product 1 to other products across the relative programs (e.g. pathways and/or APM programs), Product 1 is advantaged with respect to two programs, at parity with respect to three programs, disadvantaged with respect to one program, and not reviewed with respect to one program. The various programs summarized in the chart 620 are further listed by category adjacent to the chart 620. In such instances, a decision-maker can quickly identify target programs based on the categorization data in the chart 620.

The brand positioning analyses facilitated by the table 610 and the chart 620 are configured to facilitate comparisons between products across relevant programs. For example, a decision-maker can quickly evaluate the table 610 to determine if access to a product is restricted by one or more programs. The table 610 further highlights the types of restrictions and the extent of restrictions with respect to the percentage of oncologists affected by the program and, thus, the restrictions rooted therein. Determining the percentage of oncologists utilizing each program is further described herein. Although the table 610 refers to oncologists, the reader will readily appreciate that other types of physicians and/or providers can be listed in the table 610 depending on the indication. For example, the relevant medical specialist for the disease can be listed. To summarize, the table 610 can highlight the relative restrictiveness of products across different programs. Upon reviewing the table 610, a decision-maker can target appropriate programs (e.g. pathway(s) and/or APM program(s)) to improve access to products that are overly restricted and, thus, inaccessible to patients who may benefit from the products.

As an example, referring still to the table 610, Product 2 is approved by the FDA for first-line therapies; however, Product 2 is off-pathways for Programs 2 and 3, which impacts a combined total of 12.7% of oncologists in the United States. In other words, Product 2 is entirely restricted by Programs 2 and 3 and these restrictions effect a large percentage of oncologists and, thus, the corresponding patients under the care of these oncologists. Additionally, there are various restrictions to the use of Product 2 under Program 1 further effecting 10.5% of oncologists and a correspondingly large percentage of patients. Thus, a decision-maker can identify Programs 1, 2 and 3 as targets to expand utilization of Product 2 for the FDA-approved use as a first-line therapy for the selected indication.

Referring primarily now to FIG. 37A, a logic flowchart 630 for displaying restrictiveness of a product relative to an FDA label across multiple programs is shown. In various instances, the logic flowchart 630 can be utilized by the computing environment 100 (FIG. 1). At block 632, an indication can be selected and, at block 634, a product can be selected. For the selected indication/product, the content can be filtered such that the FDA-approved line(s) of therapy can be determined at block 636. For example, the line(s) of therapy can be extracted from the FDA-approved label for the product. A program (e.g. a pathway program and/or APM program) can be selected at block 638. At block 640, the selected program's suggested uses of the product with respect to lines of therapy can be compared to the FDA-approved line(s) of therapy. Upon comparing the FDA-approved uses to the program's suggested uses, a restrictiveness category can be assigned at block 642. For example, the restrictiveness category can be selected from the following categories, which are further described herein: advantaged, parity, some restrictions, and off pathways. The foregoing analysis can be repeated for additional programs related to the tumor type/indication. For example, blocks 638, 640 and 642 can be repeated n times to generate n rows, as shown in the table 610 (FIG. 36). Across all of the programs selected at block 638, the comparative restrictiveness can be displayed at block 644. For example, at block 644 a table and/or chart can be displayed depicting a 1-by-n array of programs and the restrictiveness of those programs for a product relative to the product's FDA-approved lines of therapy. Exemplary graphical displays are further described herein. In various instances, other products can be selected at block 634 and blocks 636, 638, 640, 642, and 644 can be repeated for the other products. For example, m products can be analyzed to generate an m-by-n array of restrictiveness for multiple products across multiple programs.

In certain instances, the scope or effective reach of a restriction to a product based on third party programs can depend on the number of physicians (e.g. medical specialists or oncologists) participating in the third party programs. For example, if very few oncologists are subjected to a particular third party program (e.g. pathway and/or APM program), the reach of the restrictions rooted in that third party program can have a limited effect on oncologists and, thus, to patients served by those oncologists. Quantifying the number of oncologists participating in third party programs can be challenging. For example, a provider's participation in a pathway may not extend to all of the provider's sites. Furthermore, certain pathways can be payer-driven and, thus, regional exposure to third party programs can depend on a payer's dominance in a region.

Referring now to FIG. 38, a map 650 is shown. The map 650 conveys regional coverage based on the number of oncologists participating in third party programs across and/or within each state. A key 652 depicts the range, scale, or spectrum of exposure from high to low and the regions or jurisdictions (e.g. states) on the map 650 are coded (e.g. color-coded and/or shaded) to reflect the scale on the key 652. In various instances, a sortable table adjacent to the map 650 can list the top regions by oncologist exposure (e.g. the ten states with the largest number of participating providers) and the number of oncologists for each listed region, for example.

In various instances, the map 650 and the key 652 can be interactive. For example, the selection of a region of the map 650 can be configured to move an icon 654 along the key 652 to a location corresponding to the regional coverage in the selected region. For example, if Missouri were selected on the map 650, as illustrated in FIG. 38, the icon 654 can be positioned along a lower portion of the key 654 reflecting the low program coverage in Missouri. Conversely, if North Carolina were selected on the map 650, the icon 656 can move along the scale to the high end of the key 652 reflecting the high program coverage in North Carolina. In various instances, a region (e.g. a state) can be selected by hovering over the region. Additionally or alternatively, a region can be selected by clicking on the region and/or selecting the region using a search bar 656 and/or drop-down list. The selection of a region can adjust a zoom feature to zoom-in on the selected region, for example.

In various instances, the TPP Tool 234 (FIG. 5) is also configured to display the number of participating oncologists in third party programs by region. For example, the TPP Tool 234 can list the total participating oncologists in each region. In various instances, a region can be selected from the map 650 and additional information regarding the selected region can be displayed. For example, upon selecting North Carolina by interacting with the map 650, a list of states adjacent to the map 650 and/or a search bar 656, the providers utilizing third party programs within North Carolina can be displayed in a table 660 along with the third party programs to which they subscribe and/or the number of participating oncologists, as shown in FIG. 39. For example, in the table 660, Pathway 1 is utilized by Providers 1, 2, and 3 accounting for a total of 441 participating oncologists. Provider 3 also subscribes to Pathway 2 and, thus, 99 participating oncologists may be covered by Pathways 1 and 2.

The number of participating oncologists for each region can be computed based on the number of provider sites within a region that participate in a third party program. For example, Provider 1 in the table 660 may employ 400 oncologists; however, only certain provider sites may subscribe to a third-party program and, thus, the participating oncologists can be extrapolated from the number and/or size or participating sites in comparison to a provider's total number of sites and/or size. In such instances, though a provider may utilize a third-party program, all of the oncologists employed by the provider may not be subjected to the third-party program.

In various instances, the TPP Tool 234 is also configured to analyze regional exposure based on payer lives exposed to third-party programs across and/or within regions. Referring now to FIG. 40, a map 670 is shown. The map 670 conveys regional coverage based on the number of payer medical lives exposed to third party programs within each region or jurisdiction (e.g. state). A key 672 depicts the range, scale, or spectrum of exposure from high to low and the states on the map 670 are coded (e.g. color-coded and/or shaded) to reflect the scale on the key 672. In various instances, a sortable table adjacent to the map 670 can list the top regions by associated medical lives exposure (e.g. the ten states with the largest number of associated medical or pharmacy lives) and the number of lives for each listed region, for example.

In various instances, the map 670 and the key 672 can be interactive. For example, the selection of a region of the map 670 can be configured to move an icon 674 along the key 672 to a location corresponding to the regional coverage. For example, if Montana were selected on the map 670, the icon 674 can be positioned at the lowest end of the key 674 reflecting the low number of medical lives exposed to third party programs in Montana. Conversely, if North Carolina were selected on the map 670, the icon 674 can move along the scale to an upper portion of the key 672 reflecting the higher number of medical lives exposed to third party programs in North Carolina. In various instances, a region (e.g. a state) can be selected by hovering over the region. Additionally or alternatively, a region can be selected by clicking on the region and/or selecting the region using a search bar 676 and/or drop-down list. The selection of a region can adjust a zoom feature to zoom-in on the selected region, for example.

In various instances, the TPP Tool 234 (FIG. 5) is also configured to display the number of associated lives (medical lives or pharmacy lives) in third party programs by region. For example, the TPP Tool 234 can list the total associated lives in each state. In various instances, a region can be selected from the map 670 and additional information regarding the selected region can be displayed. For example, upon selecting North Carolina by interacting with the map 670, a list of states adjacent to the map 670 and/or a search bar 676, the participating payers utilizing third party programs within North Carolina can be displayed in a table 680 along with the third party programs to which they subscribe and/or the number of associated lives (medical lives or pharmacy lives), as shown in FIG. 41. For example, in the table 680, Pathway 1 is utilized by Payers 1 and 2 accounting for a total of 2,775,119 associated medical lives in North Carolina. Pathway 2, which is driven by Payer 3, accounts for 185,110 medical lives and Pathway 3, which is driven by Payer 4, accounts for 734 medical lives.

In various instances, the number of associated medical lives in each region can be computed based on payer dominance in a particular region having sites where third party programs are utilized. For example, the number of medical lives exposed to third-party programs across a region can be computed by determining which payers in the region utilize one or more third party programs. For each payer in the region utilizing one or more third-party programs, the number of medical lives in the region associated with the payer can be determined, i.e., the number of beneficiaries in the state for that payer. The total medical lives in the region can then be computed by summing the number of medical lives in the region from each payer that utilizes one or more third party programs.

Certain third party programs can drive industry-wide trends. For example, if third party programs markedly increase at a particular time, a decision-maker may want to identify which third party program(s) drove the increase. By identifying trending-setting third party programs, a decision-maker can be better informed to determine which third party programs to target in an effort to increase access to a product. Trend-setting can be analyzed based on the number of medical lives and/or pharmacy lives covered by pathways over time. Additionally or alternatively, trend-setting can be analyzed based on the number of physicians (e.g. oncologists) utilizing pathways over time.

Referring to FIGS. 42 and 43, an exemplary timeline 700 and a timeline key 702 display payer adoption based on covered medical lives over time for each pathway 706, 708, 710, 712, 714, 716, 718, 720, and 722 and for total pathways 704. The covered medical lives (or pharmacy lives) can be computed as further described herein with respect to regional coverage analyses, for example. In various instances, the adoption percentage in relationship to all medical lives (e.g. percentage of the U.S. population) is depicted along the top axis of the timeline 700, which indicates, for example, that 21% of the U.S. population adopted pathways in the first quarter of the third year, whereas only 12% of the U.S. population adopted pathways in the first quarter of the fifth year.

At the first quarter of the third year, the total pathways 704 lives increased from 50 million covered lives to 66 million covered lives and, by inspecting the covered lives for each pathway 706, 708, 710, 712, 714, 716, 718, 720, and 722. Pathway Five 714 appears to drive the trend upwards by increasing from 7 million lives to 23 million lives in that same time period. Similarly, the decrease in total covered lives at the third quarter of the fifth year can be largely attributed to a decrease in covered lives for Pathway Five 714 in that same time period, for example. In such instances, the changes with respect to Pathway Five 714 appear to be driving the trends for total pathways 704. In other instances, an increase in one of the pathway 706, 708, 710, 712, 714, 716, 718, 720, and 722 can drive a corresponding decrease in one or more other pathways indicating that utilization of the pathway(s) has shifted (e.g. increased utilization of one pathway lessens the utilization of another pathway). In various instances, a decision-maker may want to target the trend-setting pathways by number of covered lives to generate the greatest expansion of a product for a limited set of resources.

Referring to FIGS. 44 and 45, an exemplary timeline 730 and a timeline key 732 display provider utilization based on number of oncologists over time for each pathway 736, 738, 740, 742, 744, 746, 748, 750, and 752 and for total pathways 734. The number of oncologists can be computed as further described herein with respect to regional coverage analyses, for example. In various instances, the exposure percentage in relationship to all oncologists (e.g. all oncologists practicing in the U.S.) is depicted along the top axis of the timeline 730, which indicates, for example, that 33% of oncologists were exposed to pathways in the first quarter of the second year, whereas only 28% of oncologists were exposed to pathways in the first quarter of the fourth year.

At the third quarter of the second year, the number of oncologists for total pathways 734 decreased from 6,300 oncologists to 5,200 oncologists and, by inspecting the covered lives for each pathway 736, 738, 740, 742, 744, 746, 748, 750, and 752, Pathway Seven 748 appears to drive the trend downwards by decreasing from 1,200 oncologists to zero oncologists in that same time period. In other instances, an increase in number of oncologists for one pathway 736, 738, 740, 742, 744, 746, 748, 750, and 752 can drive a corresponding decrease in the number of oncologists for one or more other pathways indicating that utilization of the pathway(s) has shifted (e.g. increased utilization of one pathway lessens the utilization of another pathway). In various instances, a decision-maker may want to target the trend-setting pathways by number of oncologists to generate the greatest expansion of a product for a given set of resources.

In various instances, the TPP Tool 234 (FIG. 5) can also display pathway program coverage for a selected indication and list the number of medical lives, pharmacy lives, and/or oncologists for the pathway(s) by category—covered and not covered, for example. Referring to FIG. 46, a screenshot of a graphical representation that can be selectively displayed by the TPP Tool 234 is shown. In FIG. 46, for a selected indication, 29% (or two out of seven) third party programs cover the indication, as shown in a pie chart 760. The two pathways that cover the indication are provided in a first table 762 and the five pathways that do not cover the indication are provided in a second table 764. The tables 762, 764 include the number of medical lives and oncologists for each pathway as well.

In various instances, the TPP Tool 234 can also prioritize influencers, the key decision makers across each third-party organization, and provide information regarding the influencer's role, title, indication specialties and primary affiliation. For example, the influencers can be sorted by third party organization and include information such as whether they are a steering committee member or in a leadership role.

In various instances, the TPP Tool 234 can also include a Third Party Account Dashboard that provides account information for specific accounts covered by the tool 234. For example, whereas various analyses described herein generally provide a top-down management perspective of third party programs with respect to relative brand positioning, regional coverage, influencers, payer adoption, provider utilization, and tumor coverage across the relevant third party platforms, for example, the Third Party Account Dashboard can provide a focused profile for each third party account (e.g. each pathway and/or APM program).

For example, with respect to each third party account, the TPP Tool 234 can display a program overview highlighting exposure by medical lives, pharmacy lives, and oncologists, computed as further described herein, as well as strategic relationships with payers, providers, and/or other third parties. The third party account profile can also present adoption and reach both in terms of provider adoption and exposure geographic footprint (e.g. by state). For example, the TPP Tool 234 can determine the number of oncologists participating with a third party account and, thus, is configured to integrate providers with the pathways to project the number of oncologist, as well as the payers that have adopted the pathways and the corresponding number of pharmacy and/or medical lives.

Referring now to FIG. 47, a map 770 is shown. The map 770 conveys regional coverage based on the number of oncologists participating in a selected program (e.g. pathway or APM program) across and within each state. A key 772 depicts the range, scale, or spectrum of exposure from high to low and the regions or jurisdictions (e.g. states) on the map 770 are coded (e.g. color-coded and/or shaded) to reflect the scale on the key 772. In various instances, a sortable table adjacent to the map 770 can list the relevant providers, their location (e.g. state), and the number of oncologists for each listed provider, for example. The number of participating oncologists for each region and each program can be computed as further described herein.

In various instances, the map 770 and the key 770 can be interactive. For example, the selection of a region of the map 770 can be configured to move an icon 774 along the key 772 to a location corresponding to the regional coverage in the selected region. For example, if Florida were selected on the map 770, as illustrated in FIG. 47, the icon 774 can be positioned at the low end of the key 772 reflecting the absence of coverage by the selected program in Florida. Conversely, if North Carolina were selected on the map 770, the icon 774 can move along the scale to the high end of the key 772 reflecting the high coverage by the selected program in North Carolina. In various instances, a region (e.g. a state) can be selected by hovering over the region. Additionally or alternatively, a region can be selected by clicking on the region and/or selecting the region using a search bar 776 and/or drop-down list. The selection of a region can adjust a zoom feature to zoom-in on the selected region, for example. Additionally or alternatively, the selection of a state can propagate or display a sortable table adjacent to the zoomed-in map 770 that lists the relevant providers in the selected state and the number of oncologists for each listed provider, for example.

In certain instances, the Third Party Account Dashboard for the TPP Tool 234 can be configured to convey regional coverage based on the number of lives exposed to third party programs across and within each state. Referring now to FIG. 48, a map 780 is shown. The map 780 conveys regional coverage based on the number of payer medical lives exposed to third party programs within each region or jurisdiction (e.g. state). A key 782 depicts the range, scale, or spectrum of exposure from high to low and the states on the map 780 are coded (e.g. color-coded and/or shaded) to reflect the scale on the key 782. In various instances, a sortable table adjacent to the map 780 can list the relevant payers, their location (e.g. state), and the number of lives (medical or pharmacy) for each listed payer, for example. The number of lives covered by each program can be computed as further described herein.

In various instances, the map 780 and the key 782 can be interactive. For example, the selection of a region of the map 780 can be configured to move an icon 784 along the key 782 to a location corresponding to the regional coverage in the selected region. For example, if Kansas were selected on the map 780, the icon 774 can be positioned near the lower end of the key 782 reflecting the limited coverage by the selected program in Kansas. Conversely, if California were selected on the map 780, the icon 784 can move along the scale to the high end of the key 782 reflecting the high coverage by the selected program in California. In various instances, a region (e.g. a state) can be selected by hovering over the region. Additionally or alternatively, a region can be selected by clicking on the region and/or selecting the region using a search bar 786 and/or drop-down list. The selection of a region can adjust a zoom feature to zoom-in on the selected region, for example. Additionally or alternatively, the selection of a state can propagate or display a sortable table adjacent to the zoomed-in map 770 that lists the relevant payers in the selected state and the number of lives (medical or pharmacy) for each listed payer, for example.

As further described herein, for each indication or tumor-type, the TPP Tool 234 is configured to analyze the relative positioning of a product by a program (e.g. pathway and/or APM program) compared to the FDA-approved line of therapy for the product. With respect to the Third Party Account Dashboard, for each program, the TPP Tool 234 can present brand/product positioning for a selected indication across the products approved by the FDA-label and/or suggested by the program. An exemplary interface 790 is shown in FIG. 49. The interface 790 can be a screenshot of a graphical representation, which can be selectively displayed by the TPP Tool 234 based on inputs by the user. For example, the user can select an indication from the list 792 to propagate/display a table 794 listing the line(s) of therapy approved by the FDA-label and the line(s) of therapy suggested by the program for the selected indication. As described with respect to table 610 (FIG. 36), the two-dimensional matrix defined by the table 794 can be embedded and/or overlaid with additional information, regarding the relative positioning—advantaged, parity, some restrictions, off pathways, not reviewed, no pathways coverage, or not managed—utilizing coding, such as color-coding and/or shading within each cell and a corresponding key 796. For example, Product 6 is advantaged under the selected program with respect to the FDA-approved line of therapy; however, Product 9 is more restricted because the program recommends Product 9 but not as broadly as the FDA-label allows. Additionally, Product 3, Product 7, and Product 9 are entirely off-pathways and would generally require a PA for a patient to utilize. Finally, under the selected program, Product 1, Product 2, Product 4, and Product 5 are at parity with the FDA-label. In view of this analysis, a decision-maker can identify restricted products (e.g. Product 3, Product 7, Product 8 and Product 9) with respect to each program and the type of restrictions, as further described herein.

In various aspects, the Third Party Account Dashboard for the TPP Tool 234 can also display a timeline of covered lives for the selected program over time similar to the timeline 700 (FIG. 42), for example. Each account profile can also highlight EMR compatibility of the program, adherence rates, off-pathway selection processes, and/or program influencers, for example.

Various graphical representations and filtering schemes related to geographic regions are described herein. Although the various maps depict the United States of America and states thereof, the reader will readily appreciate that alternative geographic regions and/or sub-regions (e.g. collection of countries, states, regions, and/or zip codes, sales regions) be utilized. In various instances, the geographic region and sub-regions can be user-defined.

EXAMPLES

Example 1

A strategic decision support system for analyzing payer quality of access for at least one pharmaceutical product. The strategic decision support system comprises a remote database storing content related to payer policies and comparative metrics for the at least one pharmaceutical product, a remote server configured to access content stored in the remote database, and a local device coupled to the remote server by a network. The local device comprises an input tool and a display. In response to a filter selected with the input tool and communicated to the remote server across the network, the remote server is configured to extract policy criteria from a first payer policy based on the filter selected with the input tool, extract comparative metrics based on the filter selected with the input tool, and compare the extracted policy criteria to the extracted comparative metrics. In response to a filter selected with the input tool, the remote server is further configured to assign, based on the comparison, a restrictiveness score. In response to a filter selected with the input tool, the remote server is further configured to generate a graphical representation of the restrictiveness score and display the graphical representation via a graphical user interface on the display to facilitate payer quality of access analysis of the at least one pharmaceutical product.

Example 2

The strategic decision support system of Example 1, wherein the filter comprises at least one of a pharmaceutical product filter, an indication filter, a line of therapy filter, a patient sub-type filter, a type of payer filter, a coverage filter, a geographic filter, and any combination thereof.

Example 3

The strategic decision support system of Examples 1 or 2, wherein the comparative metrics comprise Food and Drug Administration label data to determine the relative restrictiveness of a pharmaceutical product by a payer in comparison to the Food and Drug Administration label.

Example 4

The strategic decision support system of Examples 1, 2, or 3, wherein the remote server is further configured to extract policy criteria from a second payer policy based on the filter selected with the input tool, and compare the extracted policy criteria from the first payer policy and the second payer policy to determine a value for each comparative criteria of the first payer policy relative to the second payer policy.

Example 5

The strategic decision support system of Example 4, wherein the remote server is further configured to calculate a relative quality of access score by weighing the values for each comparable criteria of the first payer policy and the second payer policy, and display the quality of access score on the graphical user interface of the display.

Example 6

The strategic decision support system of Examples 1, 2, 3, 4, or 5, wherein the remote server is further configured to extract policy criteria from a set of payer policies based on the filter selected with the input tool, compare, for each payer policy, the extracted policy criteria to the extracted comparative metrics, assign, based on the comparisons, a restrictiveness score to each payer policy based on the filter selected with the input tool, generate a graphical representation of the restrictiveness scores, and display the graphical representation via the graphical user interface on the display.

Example 7

The strategic decision support system of Examples 1, 2, 3, 4, 5, or 6, wherein the filter comprises at least one pharmaceutical product and at least one indication.

Example 8

The strategic decision support system of Example 7, further comprising aggregating the restrictiveness scores for the set of payer policies based on pharmacy lives affected by the payers per the filter selected with the input tool to determine the aggregate restrictiveness for each pharmaceutical product and indication therefor in comparison to the Food and Drug Administration label.

Example 9

The strategic decision support system of Examples 1, 2, 3, 4, 5, 6, 7, or 8, wherein the comparative metrics comprise policy criteria for an analog product to determine the comparative restrictiveness across pharmaceutical products.

Example 10

The strategic decision support system of Example 9, wherein the policy criteria comprise at least one of prior authorization requirements, patient exclusion criteria, specialty pharmacy mandates, quantity limits, reauthorization requirements, and counseling requirements.

Example 11

The strategic decision support system of Examples 1, 2, 3, 4, 5, 6, 7, 8, 9, or 10, wherein the graphical representation comprise a graph and an interactive key.

Example 12

The strategic decision support system of Examples 1, 2, 3, 4, 5, 6, 7, 8, 9, 10, or 11, wherein the graphical representation comprises a map depicting the comparative restrictiveness of the pharmaceutical product across regions.

Example 13

The strategic decision support system of Examples 1, 2, 3, 4, 5, 6, 7, 8, 9, 10, 11, or 12, wherein the filter comprises a geographic filter corresponding to customized sales force regions.

Example 14

A strategic decision support system for analyzing payer quality of access for at least one pharmaceutical product. The strategic decision support system comprises a remote database storing content related to payer policies and comparative metrics for the at least one pharmaceutical product, and a remote server configured to access content stored in the remote database. In response to a filter selected by a user and communicated to the remote server across the network, the remote server is configured to extract policy criteria from a first payer policy based on the filter, extract comparative metrics based on the filter, and compare the extracted policy criteria to the extracted comparative metrics. In response to a filter selected by a user, the remote server is further configured to assign, based on the comparison, a restrictiveness score. In response to a filter selected by a user, the remote server is further configured to generate a graphical representation of the restrictiveness score and provide the graphical representation via a graphical user interface to facilitate payer quality of access analysis of the at least one pharmaceutical product.

Example 15

The strategic decision support system of Example 14, wherein the filter comprises at least one of a pharmaceutical product filter, an indication filter, a line of therapy filter, a patient sub-type filter, a type of payer filter, a coverage filter, a geographic filter, and any combination thereof.

Example 16

A strategic decision support system for filtering content received from a remote database coupled to a network to provide a graphical user interface to enable strategic decision making to expand utilization of a pharmaceutical product. The strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network. The remote server is coupled to the local client computer via the network to analyze access restrictions to the pharmaceutical product based on a selected filter and the at least one filtering scheme to generate a graphical user interface displayed on the local client computer. The remote server is configured to analyze payer restrictions to the pharmaceutical product. A payer restriction is a restriction that originates at a payer level.

Example 17

The strategic decision support system of Example 16, wherein the set of selectable filters comprise at least one of an indication filter, a line filter, a patient sub-type filter, a product filter, a coverage filter, or any combination thereof.

Example 18

The strategic decision support system of Examples 16 or 17, wherein the remote server is configured to select payers and compare quality of access of the pharmaceutical product for each of the selected payers for the selected filters.

Example 19

The strategic decision support system of Example 16, 17, or 18, wherein the remote server is further configured to extract policy criteria from a first payer policy, extract policy criteria from a second payer policy, and compare the extracted policy criteria to determine a value for each comparable criteria of the first payer policy relative to the second payer policy.

Example 20

The strategic decision support system of Example 19, wherein the remote server is further configured to calculate a relative quality of access score by weighing the values for each comparable criteria of the first and second payer policies, and display the quality of access score on the graphical user interface of the local client computer.

Example 21

A strategic decision support system for analyzing provider restrictions for at least one pharmaceutical product. The strategic decision support system comprises a remote database storing content related to a set of providers and sales data for the at least one pharmaceutical product, a remote server configured to access content stored in the remote database, and a local device coupled to the remote server by a network. The local device comprises an input tool and a display. In response to a filter selected with the input tool and communicated to the remote server across the network, the remote server is configured to determine a first score for each of the providers. The first score is indicative of clinical capabilities. In response to a filter selected with the input tool, the remote server is further configured to determine a second score for each of the providers. The second score is indicative of centralization of operations and decision-making. In response to the filter selected with the input tool, the remote server is further configured to plot the first score and the second score for each of the providers in a two-dimensional plot. The two-dimensional plot comprises segmentation quadrants. Each segmentation quadrant corresponds to a segmentation category. In response to the filter selected with the input tool, the remote server is further configured to identify the segmentation category of each provider from the plot, generate a graphical representation of the segmentation categories, and display the graphical representation via a graphical user interface on the display to facilitate analysis of provider restrictions to a first pharmaceutical product.

Example 22

The strategic decision support system of Example 21, wherein the graphical representation comprises a map depicting a geographical location of each provider and the segmentation category of each provider at the geographical location.

Example 23

The strategic decision support system of Example 22, wherein the graphical representation further comprises sales data for the first pharmaceutical product overlaid on the map.

Example 24

The strategic decision support system of Examples 21, 22, or 23, wherein, in response to the filter selected with the input tool, the remote server is further configured to filter the graphical representation to a subset of providers categorized in one of the segmentation categories.

Example 25

The strategic decision support system of Examples 21, 22, 23, or 24, wherein, in response to the filter selected with the input tool, the remote server is further configured to compare sales data of the first pharmaceutical product across segmentation categories.

Example 26

The strategic decision support system of Examples 21, 22, 23, 24, or 25, wherein, in response to the filter selected with the input tool, the remote server is further configured to compare sales data of the first pharmaceutical product to at least one analog pharmaceutical product within a segmentation category.

Example 27

The strategic decision support system of Examples 21, 22, 23, 24, 25, or 26, wherein the first score is based on a plurality first factors comprising payment model sophistication data, standard of care development and adoption data, and personalized medicine investment data.

Example 28

The strategic decision support system of Examples 21, 22, 23, 24, 25, 26, or 27, wherein the second score is based on a plurality of second factors comprising pathway and protocol use data and product preferences data.

Example 29

The strategic decision support system of Examples 21, 22, 23, 24, 25, 26, 27, or 28, wherein at least one of the first factors is weighted to determine the first score, and wherein at least one of the second factors is weighted to determine the second score.

Example 30

The strategic decision support system of Example 28, wherein the pathway and protocol use data comprises usage rates, adherence rates, electronic medical record integration, and the existence of enforcement incentives and penalties.

Example 31

The strategic decision support system of Examples 21, 22, 23, 24, 25, 26, 27, 28, 29, or 30, wherein, in response to the filter selected with the input tool, the remote server is further configured to compare the usage rates across segmentation categories, generate a graphical representation of the comparison, and display the graphical representation of the comparison via the graphical user interface on the display to facilitate analysis of provider restrictions across the segmentation categories.

Example 32

The strategic decision support system of Examples 21, 22, 23, 24, 25, 26, 27, 28, 29, 30, or 31, wherein, in response to the filter selected with the input tool, the remote server is further configured to compare the existence of incentives and penalties across segmentation categories, generate a graphical representation of the comparison, and display the graphical representation of the comparison via the graphical user interface on the display to facilitate analysis of provider restrictions across the segmentation categories.

Example 33

The strategic decision support system of Examples 21, 22, 23, 24, 25, 26, 27, 28, 29, 30, 31 or 32, wherein the filter comprises at least one of a pharmaceutical product filter, an indication filter, a line of therapy filter, a patient sub-type filter, a type of payer filter, a coverage filter, a geographic filter, and any combination thereof.

Example 34

A strategic decision support system for analyzing provider restrictions for a set of analog pharmaceutical products. The strategic decision support system comprises a remote database storing content related to a set of providers and sales data for the set of analog pharmaceutical products, and a remote server configured to access content stored in the remote database. In response to a filter selected by a user and communicated to the remote server across a network, the remote server is configured to determine a first score for each of the providers, determine a second score for each of the providers, plot the first score and the second score for each of the providers in a two-dimensional plot. The two-dimensional plot comprises segmentation quadrants. Each segmentation quadrant corresponds to a segmentation category. In response to the filter selected by a user, the remote server is further configured to identify the segmentation category of each provider from the plot, determine a market distribution for the set of analog pharmaceutical products with each segmentation category, compare the market distribution across segmentation categories, generate a graphical representation of the comparison, and display the graphical representation via a graphical user interface to facilitate analysis of provider restrictions to the set of analog pharmaceutical products.

Example 35

The strategic decision support system of Example 34, wherein, in response to the filter selected by a user, the remote server is further configured to compare the market distribution for a single provider with a first segmentation category to the first segmentation category as a whole, generate a graphical representation of the comparison, and display the graphical representation via the graphical user interface to facilitate analysis of provider restrictions to the set of analog pharmaceutical products.

Example 36

The strategic decision support system of Examples 34 or 35, wherein the filter comprises at least one of a pharmaceutical product filter, an indication filter, a line of therapy filter, a patient sub-type filter, a type of payer filter, a coverage filter, a geographic filter, and any combination thereof.

Example 37

A strategic decision support system for filtering content received from a remote database coupled to a network to provide a graphical user interface to enable strategic decision making to expand utilization of a pharmaceutical product. The strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network. The remote server is coupled to the local client computer to analyze access restrictions to the pharmaceutical product based on a selected filter and the at least one filtering scheme to generate a graphical user interface displayed on the local client computer. The remote server is configured to analyze provider restrictions to the pharmaceutical product. A provider restriction is a restriction that originates at a provider level.

Example 38

The strategic decision support system of Example 37, wherein the set of selectable filters comprise at least one of an indication filter, a line filter, a patient sub-type filter, a product filter, a coverage filter, or any combination thereof.

Example 39

The strategic decision support system of Examples 37 or 38, wherein the remote server is configured to select providers and compare quality of access of the pharmaceutical product for each of the selected providers for the selected filters.

Example 40

The strategic decision support system of Example 39, wherein the remote server is configured to determine a centralized operations and restrictiveness score and a clinical capabilities and progressiveness score for each of the selected providers, segment the selected providers into segmentation categories based on the centralized operations and restrictiveness score and the clinical capabilities and progressiveness score, and display the segmentation categories for each of the selected providers on the graphical user interface of the local client computer.

Example 41

A strategic decision support system for analyzing third party-based restrictions for at least one pharmaceutical product. The strategic decision support system comprises a remote database storing content related to third party policies and comparative metrics for the at least one pharmaceutical product, a remote server configured to access content stored in the remote database, and a local device coupled to the remote server by a network. The local device comprises an input tool and a display. In response to a filter selected with the input tool and communicated to the remote server across the network, the remote server is configured to extract policy criteria for a first pharmaceutical product from a third party policy based on the filter selected with the input tool, extract comparative metrics for the first pharmaceutical product based on the filter selected with the input tool, compare the extracted policy criteria to the extracted comparative metrics. In response to a filter selected with the input tool and communicated to the remote server across the network, the remote server is further configured to assign, based on the comparison, a restrictiveness score. In response to a filter selected with the input tool and communicated to the remote server across the network, the remote server is further configured to generate a graphical representation of the restrictiveness score, and display the graphical representation via a graphical user interface on the display to facilitate analysis of third-party based restrictions to the first pharmaceutical product for the third party policy.

Example 42

The strategic decision support system of Example 41, wherein the filter comprises at least one of a pharmaceutical product filter, an indication filter, a line of therapy filter, a patient sub-type filter, a type of payer filter, a coverage filter, a geographic filter, and any combination thereof.

Example 43

The strategic decision support system of Examples 41 or 42, wherein the third party policy comprises a pathway.

Example 44

The strategic decision support system of Examples 41, 42, or 43, wherein the comparative metrics comprise approved uses of the first pharmaceutical products according to the Food and Drug Administration label, and wherein comparing the extracted policy criteria to the extracted comparative metrics comprises identifying non-overlapping approved uses of the first pharmaceutical product.

Example 45

The strategic decision support system of Examples 41, 42, 43, or 44, wherein the restrictiveness score comprises one of advantaged, parity, restricted, no pathways coverage, off-pathways, and not managed.

Example 46

The strategic decision support system of Examples 41, 42, 43, 44, or 45, wherein the restrictiveness score is defined as advantaged when approved uses under the third party policy are broader than the approved uses under the Food and Drug Administration label.

Example 47

The strategic decision support system of Examples 41, 42, 43, 44, or 45, wherein the restrictiveness score is defined as restricted when approved uses under the third party policy are narrower than the approved uses under the Food and Drug Administration label.

Example 48

The strategic decision support system of Example 41, 42, 43, 44, 45, 46, or 47, wherein, in response to the filter selected with the input tool, the remote server is further configured to extract policy criteria for a set of pharmaceutical products from the third party policy based on the filter selected with the input tool, extract comparative metrics for the set of pharmaceutical products based on the filter selected with the input tool, and compare the extracted policy criteria for each pharmaceutical product to the extracted comparative metrics. In response to the filter selected with the input tool, the remote server is further configured to assign to each pharmaceutical product, based on the comparison, a product restrictiveness score. In response to the filter selected with the input tool, the remote server is further configured to generate a graphical representation of the product restrictiveness scores. The graphical representation is displayed via the graphical user interface on the display to facilitate comparative analysis of third-party based restrictions in the third party policy across the set of pharmaceutical products.

Example 49

The strategic decision support system of Example 41, 42, 43, 44, 45, 46, or 47, wherein, in response to the filter selected with the input tool, the remote server is further configured to extract policy criteria for a first pharmaceutical product from a set of third party policies based on the filter selected with the input tool, extract comparative metrics for the first pharmaceutical product based on the filter selected with the input tool, and compare the extracted policy criteria for each third party policy to the extracted comparative metrics. In response to the filter selected with the input tool, the remote server is further configured to assign, based on the comparison, a restrictiveness score to the first pharmaceutical product for each third party policy. In response to the filter selected with the input tool, the remote server is further configured to generate a graphical representation of the restrictiveness scores. The graphical representation is displayed via the graphical user interface on the display to facilitate analysis of third-party based restrictions for the first pharmaceutical product across the set of third party policies.

Example 50

The strategic decision support system of Examples 41, 42, 43, 44, 45, 46, 47, 48, or 49, wherein the graphical representation comprise a graph and an interactive key.

Example 51

The strategic decision support system of Examples 41, 42, 43, 44, 45, 46, 47, 48, 49, or 50, wherein the graphical representation comprises a map depicting exposure to the pharmaceutical product across regions.

Example 52

The strategic decision support system of Example 51, wherein the exposure comprises payer lives exposed to the pharmaceutical product via the third party policy.

Example 53

The strategic decision support system of Example 51, wherein the exposure comprises providers exposed to the pharmaceutical product via the third party policy.

Example 54

The strategic decision support system of Examples 41, 42, 43, 44, 45, 46, 47, 48, 49, 50, 51, or 52, wherein the graphical representation comprises a graph depicting exposure to the pharmaceutical product via the third party policy over time.

Example 55

A strategic decision support system for analyzing third party-based restrictions for a set of pharmaceutical products. The strategic decision support system comprises a remote database storing content related to third party policies and comparative metrics for the set of pharmaceutical products, and a remote server configured to access content stored in the remote database. In response to a filter selected by a user and communicated to the remote server across a network, the remote server is configured to extract policy criteria for the set of pharmaceutical products from a set of third party polices based on the filter selected by a user. In response to the filter selected by the user, the remote server is configured to, extract, for each pharmaceutical product, comparative regulatory metrics based on the filter selected by the user, and compare the extracted policy criteria for each pharmaceutical product and each third party policy to the extracted comparative regulatory metrics. In response to a filter selected by a user, the remote server is configured to assign, based on the comparison, a restrictiveness score to each pharmaceutical product in each third party policy, generate a graphical representation of the restrictiveness scores, and provide the graphical representation via a graphical user interface to facilitate analysis of third-party based restrictions across the set of third party policies for the set of pharmaceutical products.

Example 56

A strategic decision support system for filtering content received from a remote database coupled to a network to provide a graphical user interface to enable strategic decision making to expand utilization of a pharmaceutical product. The strategic decision support system comprises a local client computer to generate access to content stored in the remote database, at least one filtering scheme, a set of selectable filters configured to filter the content stored in the remote database according to the at least one filtering scheme, and a remote server coupled to the local client computer via the network. The remote server is coupled to the local client computer via the network to analyze access restrictions to the pharmaceutical product based on a selected filter and the at least one filtering scheme to generate a graphical user interface displayed on the local client computer. The remote server is configured to analyze third party restrictions to the pharmaceutical product. A third party restriction is a restriction that originates at a third party level. A third party is intermediate to the payer and the provider.

Example 57

The strategic decision support system of Example 56, wherein the set of selectable filters comprise at least one of an indication filter, a line filter, a patient sub-type filter, a product filter, a coverage filter, or any combination thereof.

Example 58

The strategic decision support system of Examples 56 or 57, wherein the remote server is configured to select third parties and compare quality of access of the pharmaceutical product for each of the selected third parties for the selected filters.

Example 59

The strategic decision support system of Examples 56, 57, or 58, wherein the remote server is configured to determine regulatory approved use of the pharmaceutical product, and compare the regulatory approved use to a third party recommended use of the pharmaceutical product. The remote server is further configured to categorize a restrictiveness of the regulatory approved use relative to the third party recommended use of the pharmaceutical product, and display the restrictiveness on the graphical user interface of the local client computer.

Example 60

The strategic decision support system of Example 59, wherein the remote server is configured to compare the regulatory approved use to another third party recommended use of the pharmaceutical product, and categorize another restrictiveness of the regulatory approved use relative to the other third party recommended use of the pharmaceutical product. The other restrictiveness is displayed on the graphical user interface of the local client computer.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, and acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, processed and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A graphical user interface system for analyzing payer quality of access data for at least one pharmaceutical product, the system comprising:
    a remote database storing content related to payer policies and comparative metrics for the at least one pharmaceutical product;
    a remote server configured to access content stored in the remote database; and
    a local device coupled to the remote server by a network, wherein the local device comprises an input tool and a display;
    wherein, in response to a filter selected with the input tool and communicated to the remote server across the network, the remote server is configured to:
        extract policy criteria from a first payer policy based on the filter selected with the input tool;

extract comparative metrics based on the filter selected with the input tool;

compare the extracted policy criteria to the extracted comparative metrics;

assign, based on the comparison, a restrictiveness score based on the filter;

display a graphical representation comprising the restrictiveness score via an interactive user interface (interactive UI) on the display, wherein the graphical representation comprises at least one of a filter tool, an interactive key, or a search tool, wherein interaction with elements of the interactive UI causes at least one of a display of additional information, opening of a new window, moving a graphical element to a new position, adjusting a zoom, highlighting a graphical element, filtering content from the graphical representation, or displaying a new graphical element, wherein, upon hovering a cursor over a graph in the interactive UI provides at least one of additional details regarding accessibility data for the at least one pharmaceutical product, additional data comprising an interactive key, or additional data related to data already displayed on the interactive UI.

2. The system of claim 1, wherein the filter comprises at least one of a pharmaceutical product filter, an indication filter, a line of therapy filter, a patient sub-type filter, a type of payer filter, a coverage filter, a geographic filter, and any combination thereof.

3. The system of claim 1, wherein the comparative metrics comprise Food and Drug Administration label data to determine the relative restrictiveness of a pharmaceutical product by a payer in comparison to the Food and Drug Administration label.

4. The system of claim 1, wherein the remote server is further configured to:

extract policy criteria from a second payer policy based on the filter selected with the input tool; and compare the extracted policy criteria from the first payer policy and the second payer policy to determine a value for each comparative criteria of the first payer policy relative to the second payer policy.

5. The system of claim 4, wherein the remote server is further configured to:

calculate a relative quality of access score by weighing the values for each comparable criteria of the first payer policy and the second payer policy; and display the quality of access score on the graphical user interface of the display.

6. The system of claim 1, wherein the remote server is further configured to:

extract policy criteria from a set of payer policies based on the filter selected with the input tool;

compare, for each payer policy, the extracted policy criteria to the extracted comparative metrics;

assign, based on the comparisons, a restrictiveness score to each payer policy based on the filter selected with the input tool;

generate a graphical representation of the restrictiveness scores, wherein the graphical representation comprises a visual characterization of the percentage of medical lives subjected to each restrictiveness score along the restrictiveness scale; and display the graphical representation via the graphical user interface on the display.

7. The system of claim 6, wherein the filter comprises at least one pharmaceutical product and at least one indication.

8. The system of claim 7, further comprising aggregating the restrictiveness scores for the set of payer policies based on pharmacy lives affected by the payers per the filter selected with the input tool to determine the aggregate restrictiveness for each pharmaceutical product and indication therefor in comparison to the Food and Drug Administration label.

9. The system of claim 1, wherein the comparative metrics comprise policy criteria for an analog product to determine the comparative restrictiveness across pharmaceutical products.

10. The system of claim 9, wherein the policy criteria comprise at least one of prior authorization requirements, patient exclusion criteria, specialty pharmacy mandates, quantity limits, reauthorization requirements, and counseling requirements.

11. The system of claim 1, wherein the graphical representation comprise a graph and an interactive key.

12. The system of claim 1, wherein the graphical representation comprises a map depicting the comparative restrictiveness of the pharmaceutical product across regions.

13. The system of claim 12, wherein the filter comprises a geographic filter corresponding to customized sales force regions.

14. A system for displaying payer quality of access for at least one pharmaceutical product, the system comprising:

a remote database storing content related to payer policies and comparative metrics for the at least one pharmaceutical product; and a remote server configured to access content stored in the remote database;

wherein, in response to a filter selected by a user and communicated to the remote server across the network, the remote server is configured to:

extract policy criteria from a first payer policy based on the filter;

extract comparative metrics based on the filter;

compare the extracted policy criteria to the extracted comparative metrics;

assign, based on the comparison, a restrictiveness score based on the filter; and display a graphical representation comprising an interactive key via an interactive graphical user interface (interactive UI) on the display, wherein hovering a cursor over an icon on the graphical representation causes display of additional data related to comparative restrictiveness metrics for the at least one pharmaceutical product.

15. The system of claim 14, wherein the filter comprises at least one of a pharmaceutical product filter, an indication filter, a line of therapy filter, a patient sub-type filter, a type of payer filter, a coverage filter, a geographic filter, and any combination thereof.

* * * * *